(12) United States Patent
Kuersten et al.

(10) Patent No.: US 11,976,271 B2
(45) Date of Patent: *May 7, 2024

(54) NUCLEASE-BASED RNA DEPLETION

(71) Applicant: ILLUMINA, INC., San Diego, CA (US)

(72) Inventors: Scott Kuersten, Madison, WI (US); Frederick Hyde, Madison, WI (US); Asako Tetsubayashi, Madison, WI (US)

(73) Assignee: Illumina, Inc., San Diego, CA (US)

(*) Notice: Subject to any disclaimer, the term of this patent is extended or adjusted under 35 U.S.C. 154(b) by 146 days.

This patent is subject to a terminal disclaimer.

(21) Appl. No.: 17/812,683

(22) Filed: Jul. 14, 2022

(65) Prior Publication Data

US 2022/0403370 A1    Dec. 22, 2022

Related U.S. Application Data

(63) Continuation of application No. 16/721,468, filed on Dec. 19, 2019, now Pat. No. 11,421,216.

(60) Provisional application No. 62/847,797, filed on May 14, 2019, provisional application No. 62/783,869, filed on Dec. 21, 2018.

(51) Int. Cl.
 *C12Q 1/68* (2018.01)
 *C12N 15/10* (2006.01)
 *C12Q 1/6806* (2018.01)
 *C12Q 1/6848* (2018.01)
 *C12Q 1/6876* (2018.01)

(52) U.S. Cl.
 CPC ..... *C12N 15/1003* (2013.01); *C12N 15/1024* (2013.01); *C12Q 1/6806* (2013.01); *C12Q 1/6848* (2013.01); *C12Q 1/6876* (2013.01)

(58) Field of Classification Search
 None
 See application file for complete search history.

(56) References Cited

U.S. PATENT DOCUMENTS

| | | | |
|---|---|---|---|
| 6,040,138 | A | 3/2000 | Lockhart et al. |
| 6,900,013 | B1 | 5/2005 | Wang et al. |
| 9,005,891 | B2 | 4/2015 | Sinicropi et al. |
| 9,428,794 | B2 | 8/2016 | Farmer et al. |

(Continued)

FOREIGN PATENT DOCUMENTS

| | | |
|---|---|---|
| AU | 738261 B2 | 1/1999 |
| CA | 2037673 A1 | 9/1991 |

(Continued)

OTHER PUBLICATIONS

Bostick et al., "Strand-Specific Transcriptome Sequencing Using SMART Technology," Curr. Protoc. Mol. Biol., 116: 4.27.1-4.27.18.

(Continued)

*Primary Examiner* — Aaron A Priest
(74) *Attorney, Agent, or Firm* — McNeill Baur PLLC

(57) ABSTRACT

The present disclosure is related to methods and materials for depleting unwanted RNA species from a nucleic acid sample. In particular, the present disclosure describes how to remove unwanted rRNA, tRNA, mRNA or other RNA species that could interfere with the analysis, manipulation and study of target RNA molecules in a sample.

22 Claims, 11 Drawing Sheets
Specification includes a Sequence Listing.

(56) References Cited

U.S. PATENT DOCUMENTS

| | | |
|---|---|---|
| 9,745,570 B2 | 8/2017 | Sooknanan |
| 9,902,991 B2 | 2/2018 | Sinicropi et al. |
| 2003/0059789 A1 | 3/2003 | Efimov et al. |
| 2005/0003369 A1 | 1/2005 | Christians et al. |
| 2006/0188927 A1 | 8/2006 | Slattum et al. |
| 2008/0102454 A1 | 5/2008 | Wang |
| 2011/0111409 A1 | 5/2011 | Sinicropi et al. |
| 2014/0093882 A1* | 4/2014 | Farmer ............... C12Q 1/6848 435/6.12 |
| 2016/0040218 A1 | 2/2016 | Guttman et al. |
| 2017/0103796 A1 | 4/2017 | Hanson et al. |
| 2018/0002743 A1 | 1/2018 | Huie et al. |

FOREIGN PATENT DOCUMENTS

| | | | |
|---|---|---|---|
| CN | 1176663 A | 3/1998 | |
| CN | 1333465 A | 1/2002 | |
| CN | 1405325 A | 3/2003 | |
| CN | 101103122 A | 1/2008 | |
| CN | 101935697 A | 1/2011 | |
| CN | 104685071 A | 6/2015 | |
| CN | 106399533 A | 2/2017 | |
| CN | 107119043 A | 9/2017 | |
| CN | 108367291 A | 8/2018 | |
| EP | 1162278 A2 | 12/2001 | |
| RU | 2558292 C1 | 7/2015 | |
| WO | 9409156 A1 | 4/1994 | |
| WO | 0216647 A1 | 2/2002 | |
| WO | 2010115160 A2 | 10/2010 | |
| WO | 2012104261 A1 | 8/2012 | |
| WO | 2012140224 A1 | 10/2012 | |
| WO | 2013079649 A1 | 6/2013 | |
| WO | 2013113699 A2 | 8/2013 | |
| WO | 2014043133 A1 | 3/2014 | |
| WO | 2014044724 A1 | 3/2014 | |
| WO | WO-2014044724 A1 * | 3/2014 | ......... C12N 15/1093 |
| WO | 2014152397 A2 | 9/2014 | |
| WO | 2015002813 A1 | 1/2015 | |
| WO | 2015095226 A2 | 6/2015 | |
| WO | 2016057832 A2 | 4/2016 | |
| WO | 2017040306 A1 | 3/2017 | |
| WO | 2017140659 A1 | 8/2017 | |

OTHER PUBLICATIONS

Morlan et al., "Selective depletion of rRNA enables whole transcriptome profiling of archival fixed tissue," PLOS One, 2012, 7(8): e42882, 13 pages.

Office Action (English translation), issued in corresponding Chinese Application No. 201980064287.5, dated May 6, 2023.

Official Decision of Grant (English translation), issued in corresponding Russian Application No. 2021107892, dated Oct. 26, 2022.

"New England Biolabs® Introduces New Ribosomal RNA Depletion Technology from Genomic Health," Press Release, Aug. 19, 2014, available at https://www.neb.com/about-neb/news-and-press-releases/2014/08/19/new-ribosomal-rna-depletion-technology, 2 pages.

Champoux et al., "Ribonuclease H: properties, substrate specificity and roles in retroviral reverse transcription," FEBS J., 2009, 276: 1506-1516.

International Search Report and Written Opinion, International Application No. PCT/US2019/067582, dated Apr. 27, 2020, 11 pages.

Angmead et al., "Fast gapped-read alignment with Bowtie 2," Nature Methods, 2012, 9: 357-359.

Li et al., "Organism-Specific rRNA Capture System for Application in Next-Generation Sequencing", PLOS ONE, 2013, 8(9): e74286, pp. 1-7.

Mauro et al., "rRNA-like sequences occur in diverse primary transcripts: Implications for the control of gene expression," Proc. Natl. Acad. Sci. USA, 1997, 94: 422-427.

Mignone and Pesole, "rRNA-like sequences in human mRNAs," Appl. Bioinformatics, 2002, 1(3): 145-154.

Morian et al., "Selective depletion of rRNA enables whole transcriptome profiling of archival fixed tissue," PLOS One, 2012, 7(8): e42882, pp. 1-8.

NCBI Reference Sequence AC_000021.2, "*Homo Sapiens* Mitochondrion, Complete Genome," Nucleotide—NCBI, 2008, 20 pages.

Schultz et al., "Sequence, distance, and accessibility are determinants of 5'-end-directed cleavages by retroviral RNases H*," J. Biol. Chem., 2006, 281(4): 1943-1955.

Notice of Allowance (English translation) issued in corresponding Chinese application No. 201980064287.5, dated Jan. 29, 2024, 8 pages.

\* cited by examiner

| Sample | Read length | Reads | % total alignment | % abundant | % unaligned | Median CV coverage uniformity | % stranded |
|---|---|---|---|---|---|---|---|
| 2181-144-HBR_100_1 | 76/76 | 21,123,299 | 95.99% | 3.83% | 4.01% | 0.59 | 98.29% |
| 2181-144-HBR_100_2 | 76/76 | 16,836,087 | 94.45% | 4.14% | 5.55% | 0.64 | 98.04% |
| 2181-144-HBR_100_3 | 76/76 | 20,318,497 | 95.41% | 3.68% | 4.59% | 0.6 | 98.30% |
| 2181-144-HBR_100_4 | 76/76 | 18,415,870 | 93.57% | 6.19% | 6.43% | 0.71 | 98.34% |
| 2181-144-HBR_10_1 | 76/76 | 16,541,450 | 93.55% | 2.85% | 6.45% | 0.68 | 98.60% |
| 2181-144-HBR_10_2 | 76/76 | 14,948,830 | 83.17% | 3.19% | 16.83% | 0.76 | 98.60% |
| 2181-144-HBR_10_3 | 76/76 | 15,362,719 | 85.59% | 2.66% | 14.41% | 0.82 | 98.43% |
| 2181-144-HBR_10_4 | 76/76 | 15,973,964 | 53.28% | 3.18% | 46.72% | 0.83 | 98.64% |
| 2181-144-HBR_1_1 | 76/76 | 18,165,860 | 76.35% | 3.13% | 23.65% | 0.82 | 98.48% |
| 2181-144-HBR_1_2 | 76/76 | 18,608,239 | 79.14% | 4.46% | 20.86% | 0.74 | 98.66% |
| 2181-144-HBR_1_3 | 76/76 | 17,071,720 | 71.65% | 4.04% | 28.35% | 0.76 | 98.65% |
| 2181-144-HBR_1_4 | 76/76 | 18,655,903 | 75.76% | 4.13% | 24.24% | 0.79 | 98.61% |
| 2181_144_UHR_100_1 | 76/76 | 17,901,012 | 95.70% | 5.54% | 4.30% | 0.65 | 98.95% |
| 2181_144_UHR_100_2 | 76/76 | 19,275,813 | 96.09% | 5.74% | 3.91% | 0.63 | 98.95% |
| 2181_144_UHR_100_3 | 76/76 | 18,020,705 | 96.05% | 5.35% | 3.95% | 0.63 | 98.98% |
| 2181_144_UHR_100_4 | 76/76 | 20,194,510 | 96.34% | 5.15% | 3.66% | 0.62 | 99.01% |
| 2181-144_UHR_10_1 | 76/76 | 18,156,567 | 95.69% | 4.21% | 4.31% | 0.67 | 99.06% |
| 2181-144_UHR_10_2 | 76/76 | 17,589,818 | 95.47% | 2.93% | 4.53% | 0.68 | 99.04% |
| 2181-144_UHR_10_3 | 76/76 | 11,663,050 | 80.16% | 3.95% | 19.84% | 0.88 | 99.11% |
| 2181-144_UHR_10_4 | 76/76 | 14,233,408 | 62.15% | 37.92% | 37.85% | 1.32 | 97.95% |
| 2181-144_UHR_1_1 | 76/76 | 15,352,007 | 70.16% | 3.77% | 29.84% | 0.9 | 98.94% |
| 2181-144_UHR_1_2 | 76/76 | 12,984,189 | 56.02% | 4.14% | 43.98% | 1.06 | 98.98% |
| 2181-144_UHR_1_3 | 76/76 | 15,925,824 | 69.17% | 4.25% | 30.83% | 0.94 | 98.95% |
| 2181-144_UHR_1_4 | 76/76 | 18,471,152 | 74.59% | 3.09% | 25.41% | 0.87 | 98.03% |

Groupings (left label):
- 100 ng: rows 1–4
- 10 ng: rows 5–8
- 1 ng: rows 9–12
- 100 ng: rows 13–16
- 10 ng: rows 17–20
- 1 ng: rows 21–24

Figure 3

| Sample species | % Formamide | Read Length | Number of Reads | % Total Aligned | % Abundant | % Unaligned | Median CV Coverage Uniformity | % Stranded |
|---|---|---|---|---|---|---|---|---|
| Mouse | 0 | 76/76 | 20,906,236 | 95.89% | 6.77% | 4.11% | 0.7 | 98.81% |
| Mouse | 0 | 76/76 | 21,519,072 | 95.41% | 5.99% | 4.59% | 0.7 | 98.75% |
| Mouse | 0 | 76/76 | 16,278,898 | 95.81% | 4.95% | 4.19% | 0.69 | 98.78% |
| Mouse | 25 | 76/76 | 17,899,655 | 95.53% | 7.87% | 4.47% | 0.57 | 98.93% |
| Mouse | 25 | 76/76 | 14,429,705 | 95.90% | 5.77% | 4.10% | 0.59 | 98.92% |
| Mouse | 25 | 76/76 | 13,912,920 | 95.49% | 6.01% | 4.51% | 0.59 | 98.89% |
| Mouse | 25 | 76/76 | 29,429,014 | 95.97% | 6.44% | 4.03% | 0.58 | 98.91% |
| Mouse | 45 | 76/76 | 12,574,052 | 95.34% | 9.55% | 4.66% | 0.57 | 98.95% |
| Mouse | 45 | 76/76 | 25,749,347 | 95.40% | 8.10% | 4.60% | 0.59 | 98.91% |
| Mouse | 45 | 76/76 | 26,674,283 | 95.57% | 7.92% | 4.43% | 0.6 | 98.98% |
| Rat | 0 | 76/76 | 24,887,831 | 95.23% | 2.36% | 4.77% | 0.64 | 98.85% |
| Rat | 0 | 76/76 | 24,044,473 | 95.60% | 1.77% | 4.40% | 0.65 | 98.77% |
| Rat | 0 | 76/76 | 24,074,413 | 95.78% | 1.71% | 4.22% | 0.67 | 98.85% |
| Rat | 0 | 76/76 | 18,888,445 | 95.53% | 2.08% | 4.47% | 0.66 | 98.81% |
| Rat | 25 | 76/76 | 19,992,000 | 95.23% | 3.40% | 4.77% | 0.52 | 99.02% |
| Rat | 25 | 76/76 | 22,550,033 | 95.65% | 3.71% | 4.35% | 0.52 | 99.01% |
| Rat | 25 | 76/76 | 19,815,333 | 95.70% | 3.55% | 4.30% | 0.52 | 98.98% |
| Rat | 25 | 76/76 | 23,590,623 | 94.86% | 4.18% | 5.14% | 0.62 | 99.03% |
| Rat | 45 | 76/76 | 14,029,563 | 95.59% | 8.87% | 4.41% | 0.51 | 99.06% |
| Rat | 45 | 76/76 | 13,833,972 | 95.55% | 7.81% | 4.45% | 0.5 | 99.04% |
| Rat | 45 | 76/76 | 12,156,542 | 95.50% | 7.89% | 4.50% | 0.51 | 99.04% |
| Rat | 45 | 76/76 | 14,414,597 | 95.47% | 8.21% | 4.53% | 0.5 | 99.04% |

Figure 4

```
SEQUENCE LISTING

Sequence total quantity: 428
SEQ ID NO: 1              moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 1
gttcgtccaa gtgcactttc cagtacactt accatgttac gacttgtctc          50

SEQ ID NO: 2              moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 2
tagggtttt agttaaatgt cctttgaagt atacttgagg agggtgacgg            50

SEQ ID NO: 3              moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 3
ttcagggccc tgttcaacta agcactctac tctcagttta ctgctaaatc           50

SEQ ID NO: 4              moltype = DNA  length = 50
FEATURE                   Location/Qualifiers
misc_feature              1..50
                          note = DNA Probe
source                    1..50
                          mol_type = other DNA
```

```
                        organism = synthetic construct
SEQUENCE: 4
agtttcataa gggctatcgt agttttctgg ggtagaaaat gtagcccatt          50

SEQ ID NO: 5           moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 5
ggctacacct tgacctaacg tctttacgtg ggtacttgcg cttactttgt          50

SEQ ID NO: 6           moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 6
ttgctgaaga tggcggtata taggctgagc aagaggtggt gaggttgatc          50

SEQ ID NO: 7           moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 7
cagaacaggc tcctctagag ggatatgaag caccgccagg tcctttgagt          50

SEQ ID NO: 8           moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 8
gtagtgttct ggcgagcagt tttgttgatt taactgttga ggtttagggc          50

SEQ ID NO: 9           moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 9
atctaatccc agtttgggtc ttagctattg tgtgttcaga tatgttaaag          50

SEQ ID NO: 10          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 10
attttgtgtc aactggagtt ttttacaact caggtgagtt ttagctttat          50

SEQ ID NO: 11          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 11
ctaaaacact ctttacgccg gcttctattg acttgggtta atcgtgtgac          50

SEQ ID NO: 12          moltype = DNA   length = 50
FEATURE                Location/Qualifiers
misc_feature           1..50
                       note = DNA Probe
source                 1..50
```

```
                        mol_type = other DNA
                        organism = synthetic construct
SEQUENCE: 12
gaaattgacc aaccctgggg ttagtatagc ttagttaaac tttcgtttat          50

SEQ ID NO: 13           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 13
actgctgttt cccgtggggg tgtggctagg ctaagcgttt tgagctgcat          50

SEQ ID NO: 14           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 14
gcttgtccct tttgatcgtg gtgatttaga gggtgaactc actggaacgg          50

SEQ ID NO: 15           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 15
taatcttact aagagctaat agaaaggcta ggaccaaacc tatttgttta          50

SEQ ID NO: 16           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 16
aaaccctgtt cttgggtggg tgtgggtata atactaagtt gagatgatat          50

SEQ ID NO: 17           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 17
gcgctttgtg aagtaggcct tatttctctt gtcctttcgt acagggagga          50

SEQ ID NO: 18           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 18
aaaccgacct ggattactcc ggtctgaact cagatcacgt aggactttaa          50

SEQ ID NO: 19           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 19
acctttaata gcggctgcac catcgggatg tcctgatcca acatcgaggt          50

SEQ ID NO: 20           moltype = DNA  length = 50
FEATURE                 Location/Qualifiers
misc_feature            1..50
                        note = DNA Probe
```

```
source                      1..50
                            mol_type = other DNA
                            organism = synthetic construct
SEQUENCE: 20
tgatatggac tctagaatag gattgcgctg ttatccctag ggtaacttgt          50

SEQ ID NO: 21               moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 21
attggatcaa ttgagtatag tagttcgctt tgactggtga agtcttagca          50

SEQ ID NO: 22               moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 22
ttgggttctg ctccgaggtc gccccaaccg aaatttttaa tgcaggtttg          50

SEQ ID NO: 23               moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 23
tgggtttgtt aggtactgtt tgcattaata aattaaagct ccatagggtc          50

SEQ ID NO: 24               moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 24
gtcatgcccg cctcttcacg ggcaggtcaa tttcactggt taaaagtaag          50

SEQ ID NO: 25               moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 25
cgtggagcca ttcatacagg tccctattta aggaacaagt gattatgcta          50

SEQ ID NO: 26               moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 26
ggtaccgcgg ccgttaaaca tgtgtcactg ggcaggcggt gcctctaata          50

SEQ ID NO: 27               moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 27
gtgatgtttt tggtaaacag gcggggtaag gtttgccgag ttccttttac          50

SEQ ID NO: 28               moltype = DNA   length = 50
FEATURE                     Location/Qualifiers
misc_feature                1..50
```

```
                         note = DNA Probe
source                   1..50
                         mol_type = other DNA
                         organism = synthetic construct
SEQUENCE: 28
cttatgagca tgcctgtgtt gggttgacag tgagggtaat aatgacttgt              50

SEQ ID NO: 29            moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 29
attgggctgt taattgtcag ttcagtgttt tgatctgacg caggcttatg              50

SEQ ID NO: 30            moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 30
tcatgttact tatactaaca ttagttcttc tatagggtga tagattggtc              50

SEQ ID NO: 31            moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 31
agttcagtta tatgtttggg attttttagg tagtgggtgt tgagcttgaa              50

SEQ ID NO: 32            moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 32
tggctgcttt taggcctact atgggtgtta aattttttac tctctctaca              50

SEQ ID NO: 33            moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 33
gtccaaagag ctgttcctct ttggactaac agttaaattt acaaggggat              50

SEQ ID NO: 34            moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 34
ggcaaattta aagttgaact aagattctat cttggacaac cagctatcac              50

SEQ ID NO: 35            moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 35
tgtcgcctct acctataaat cttcccacta ttttgctaca tagacgggtg              50

SEQ ID NO: 36            moltype = DNA  length = 50
FEATURE                  Location/Qualifiers
```

```
misc_feature            1..50
                        note = DNA Probe
source                  1..50
                        mol_type = other DNA
                        organism = synthetic construct
SEQUENCE: 36
tcttaggtag ctcgtctggt ttcggggggtc ttagctttgg ctctccttgc                50

SEQ ID NO: 37           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 37
taattcatta tgcagaaggt atagggggtta gtccttgcta tattatgctt                50

SEQ ID NO: 38           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 38
tctttcccctt gcggtactat atctattgcg ccaggtttca atttctatcg                50

SEQ ID NO: 39           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 39
ggtaaatggt ttggctaagg ttgtctggta gtaaggtgga gtgggtttgg                50

SEQ ID NO: 40           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 40
taatgatcct tccgcaggtt cacctacgga aaccttgtta cgacttttac                50

SEQ ID NO: 41           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 41
aagttcgacc gtcttctcag cgctccgcca gggccgtggg ccgacccgg                 50

SEQ ID NO: 42           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 42
ggcctcacta aaccatccaa tcggtagtag cgacgggcgg tgtgtacaaa                 50

SEQ ID NO: 43           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 43
caacgcaagc ttatgacccg cacttactcg ggaattccct cgttcatggg                 50

SEQ ID NO: 44           moltype = DNA  length = 50
```

```
FEATURE                 Location/Qualifiers
misc_feature            1..50
                        note = DNA Probe
source                  1..50
                        mol_type = other DNA
                        organism = synthetic construct
SEQUENCE: 44
ccgatcccca tcacgaatgg ggttcaacgg gttacccgcg cctgccggcg                 50

SEQ ID NO: 45           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 45
ctgagccagt cagtgtagcg cgcgtgcagc cccggacatc taagggcatc                 50

SEQ ID NO: 46           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 46
ctcaatctcg ggtggctgaa cgccacttgt ccctctaaga agttggggga                 50

SEQ ID NO: 47           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 47
ggtcgcgtaa ctagttagca tgccagagtc tcgttcgtta tcggaattaa                 50

SEQ ID NO: 48           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 48
caccaactaa gaacggccat gcaccaccac ccacggaatc gagaaagagc                 50

SEQ ID NO: 49           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 49
cctgtccgtg tccgggccgg gtgaggtttc ccgtgttgag tcaaattaag                 50

SEQ ID NO: 50           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 50
ctggtggtgc ccttccgtca attcctttaa gtttcagctt tgcaaccata                 50

SEQ ID NO: 51           moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 51
aaagactttg gtttcccgga agctgcccgg cgggtcatgg gaataacgcc                 50
```

```
SEQ ID NO: 52             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 52
ggcatcgttt atggtcggaa ctacgacggt atctgatcgt cttcgaacct              50

SEQ ID NO: 53             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 53
gattaatgaa acattcttg gcaaatgctt tcgctctggt ccgtcttgcg               50

SEQ ID NO: 54             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 54
cacctctagc ggcgcaatac gaatgccccc ggccgtccct cttaatcatg              50

SEQ ID NO: 55             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 55
accaacaaaa tagaaccgcg gtcctattcc attattccta gctgcggtat              50

SEQ ID NO: 56             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 56
ctgctttgaa cactctaatt ttttcaaagt aaacgcttcg ggccccgcgg              50

SEQ ID NO: 57             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 57
gcatcgaggg ggcgccgaga ggcaaggggc ggggacgggc ggtggctcgc              50

SEQ ID NO: 58             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 58
ccgcccgctc ccaagatcca actacgagct ttttaactgc agcaacttta              50

SEQ ID NO: 59             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 59
gctggaatta ccgcggctgc tggcaccaga cttgccctcc aatggatcct              50
```

-continued

```
SEQ ID NO: 60          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 60
agtggactca ttccaattac agggcctcga aagagtcctg tattgttatt                50

SEQ ID NO: 61          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 61
cccgggtcgg gagtgggtaa tttgcgcgcc tgctgccttc cttggatgtg                50

SEQ ID NO: 62          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 62
gctccctctc cggaatcgaa ccctgattcc ccgtcacccg tggtcaccat                50

SEQ ID NO: 63          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 63
taccatcgaa agttgatagg gcagacgttc gaatgggtcg tcgccgccac                50

SEQ ID NO: 64          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 64
ggcccgaggt tatctagagt caccaaagcc gccggcgccc gccccccggc                50

SEQ ID NO: 65          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 65
gctgaccggg ttggttttga tctgataaat gcacgcatcc cccccgcgaa                50

SEQ ID NO: 66          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 66
tcggcatgta ttagctctag aattaccaca gttatccaag taggagagga                50

SEQ ID NO: 67          moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 67
```

```
aaccataact gatttaatga gccattcgca gtttcactgt accggccgtg        50

SEQ ID NO: 68           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 68
atggcttaat ctttgagaca agcatatgct actggcagga tcaaccaggt        50

SEQ ID NO: 69           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 69
gacaaaccct tgtgtcgagg gctgactttc aatagatcgc agcgagggag        50

SEQ ID NO: 70           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 70
cgaaaccccg acccagaagc aggtcgtcta cgaatggttt agcgccaggt        50

SEQ ID NO: 71           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 71
ggtgcgtgac gggcgagggg gcggccgcct ttccggccgc gccccgtttc        50

SEQ ID NO: 72           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 72
ctccgcaccg gaccccggtc ccggcgcgcg gcggggcacg cgccctcccg        50

SEQ ID NO: 73           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 73
aggggggggc ggcccgccgg cggggacagg cggggaccg gctatccgag         50

SEQ ID NO: 74           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 74
gcggcgctgc cgtatcgttc gcctgggcgg gattctgact tagaggcgtt        50

SEQ ID NO: 75           moltype = DNA   length = 50
FEATURE                 Location/Qualifiers
misc_feature            1..50
                        note = DNA Probe
source                  1..50
                        mol_type = other DNA
                        organism = synthetic construct
```

```
SEQUENCE: 75
agatggtagc ttcgccccat tggctcctca gccaagcaca tacaccaaat          50

SEQ ID NO: 76         moltype = DNA  length = 50
FEATURE               Location/Qualifiers
misc_feature          1..50
                      note = DNA Probe
source                1..50
                      mol_type = other DNA
                      organism = synthetic construct
SEQUENCE: 76
tcctctcgta ctgagcagga ttaccatggc aacaacacat catcagtagg          50

SEQ ID NO: 77         moltype = DNA  length = 50
FEATURE               Location/Qualifiers
misc_feature          1..50
                      note = DNA Probe
source                1..50
                      mol_type = other DNA
                      organism = synthetic construct
SEQUENCE: 77
ctcacgacgg tctaaaccca gctcacgttc cctattagtg ggtgaacaat          50

SEQ ID NO: 78         moltype = DNA  length = 50
FEATURE               Location/Qualifiers
misc_feature          1..50
                      note = DNA Probe
source                1..50
                      mol_type = other DNA
                      organism = synthetic construct
SEQUENCE: 78
ttctgcttca caatgatagg aagagccgac atcgaaggat caaaaagcga          50

SEQ ID NO: 79         moltype = DNA  length = 50
FEATURE               Location/Qualifiers
misc_feature          1..50
                      note = DNA Probe
source                1..50
                      mol_type = other DNA
                      organism = synthetic construct
SEQUENCE: 79
ttggccgcca caagccagtt atccctgtgg taactttct gacacctcct           50

SEQ ID NO: 80         moltype = DNA  length = 50
FEATURE               Location/Qualifiers
misc_feature          1..50
                      note = DNA Probe
source                1..50
                      mol_type = other DNA
                      organism = synthetic construct
SEQUENCE: 80
ggtcagaagg atcgtgaggc cccgctttca cggtctgtat tcgtactgaa          50

SEQ ID NO: 81         moltype = DNA  length = 50
FEATURE               Location/Qualifiers
misc_feature          1..50
                      note = DNA Probe
source                1..50
                      mol_type = other DNA
                      organism = synthetic construct
SEQUENCE: 81
agcttttgcc cttctgctcc acgggaggtt tctgtcctcc ctgagctcgc          50

SEQ ID NO: 82         moltype = DNA  length = 50
FEATURE               Location/Qualifiers
misc_feature          1..50
                      note = DNA Probe
source                1..50
                      mol_type = other DNA
                      organism = synthetic construct
SEQUENCE: 82
ttaccgtttg acaggtgtac cgccccagtc aaactcccca cctggcactg          50

SEQ ID NO: 83         moltype = DNA  length = 50
FEATURE               Location/Qualifiers
misc_feature          1..50
                      note = DNA Probe
source                1..50
                      mol_type = other DNA
```

```
                        organism = synthetic construct
SEQUENCE: 83
gcgcccggcc gggcgggcgc ttggcgccag aagcgagagc ccctcgggct        50

SEQ ID NO: 84           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 84
ccgggtcagt gaaaaaacga tcagagtagt ggtatttcac cggcggcccg        50

SEQ ID NO: 85           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 85
cgccccgggc ccctcgcggg gacaccgggg gggcgccggg ggcctcccac        50

SEQ ID NO: 86           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 86
catgtctctt caccgtgcca gactagagtc aagctcaaca gggtcttctt        50

SEQ ID NO: 87           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 87
ccaagcccgt tcccttggct gtggtttcgc tggatagtag gtagggacag        50

SEQ ID NO: 88           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 88
tccattcatg cgcgtcacta attagatgac gaggcatttg gctaccttaa        50

SEQ ID NO: 89           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 89
tcccgccgtt tacccgcgct tcattgaatt tcttcacttt gacattcaga        50

SEQ ID NO: 90           moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 90
cacatcgcgt caacacccgc cgcgggcctt cgcgatgctt tgttttaatt        50

SEQ ID NO: 91           moltype = DNA   length = 50
FEATURE                 Location/Qualifiers
misc_feature            1..50
                        note = DNA Probe
source                  1..50
```

```
                                  mol_type = other DNA
                                  organism = synthetic construct
SEQUENCE: 91
cctggtccgc accagttcta agtcggctgc taggcgccgg ccgaggcgag                50

SEQ ID NO: 92             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 92
cggccccggg ggcggacccg gcgggggggga ccggcccgcg gcccctccgc               50

SEQ ID NO: 93             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 93
ccgccgcgcg ccgaggagga gggggaacg ggggcggac ggggccgggg                  50

SEQ ID NO: 94             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 94
acgaaccgcc ccgccccgcc gcccgccgac cgccgccgcc cgaccgctcc                50

SEQ ID NO: 95             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 95
cgcgcgcgac cgagacgtgg ggtggggtg gggggcgcgc cgcgccgccg                 50

SEQ ID NO: 96             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 96
gcggccgcga cgcccgccgc agctggggcg atccacggga agggcccggc                50

SEQ ID NO: 97             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 97
gcgccgccgc cggcccccccg ggtcccgggg gccccctcg cggggacctg                50

SEQ ID NO: 98             moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 98
ccggcggccg ccgcgcggcc cctgccgccc cgacccttct cccccgccg                 50

SEQ ID NO: 99             moltype = DNA  length = 50
FEATURE                   Location/Qualifiers
misc_feature              1..50
                          note = DNA Probe
```

```
source                      1..50
                            mol_type = other DNA
                            organism = synthetic construct
SEQUENCE: 99
ctcccccggg gagggggag gacggggagc ggggagaga gagagagaga          50

SEQ ID NO: 100              moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 100
agggagcgag cggcgcgcgc gggtggggcg ggggagggcc gcgaggggg          50

SEQ ID NO: 101              moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 101
ggggggcgcgc gcctcgtcca gccgcggcgc gcgcccagcc ccgcttcgcg          50

SEQ ID NO: 102              moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 102
cccagccctt agagccaatc cttatcccga agttacggat ccggcttgcc          50

SEQ ID NO: 103              moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 103
cattgttcca acatgccaga ggctgttcac cttggagacc tgctgcggat          50

SEQ ID NO: 104              moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 104
cgcgagattt acaccctctc ccccggattt tcaagggcca gcgagagctc          50

SEQ ID NO: 105              moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 105
aaccgcgacg ctttccaagg cacgggcccc tctctcgggg cgaacccatt          50

SEQ ID NO: 106              moltype = DNA   length = 50
FEATURE                     Location/Qualifiers
misc_feature                1..50
                            note = DNA Probe
source                      1..50
                            mol_type = other DNA
                            organism = synthetic construct
SEQUENCE: 106
cttcacaaag aaaagagaac tctccccggg gctcccgccg gcttctccgg          50

SEQ ID NO: 107              moltype = DNA   length = 50
FEATURE                     Location/Qualifiers
misc_feature                1..50
```

```
                        note = DNA Probe
source                  1..50
                        mol_type = other DNA
                        organism = synthetic construct
SEQUENCE: 107
cgcactggac gcctcgcggc gcccatctcc gccactccgg attcggggat              50

SEQ ID NO: 108          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 108
tttcgatcgg ccgagggcaa cggaggccat cgcccgtccc ttcggaacgg              50

SEQ ID NO: 109          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 109
caggaccgac tgacccatgt tcaactgctg ttcacatgga acccttctcc              50

SEQ ID NO: 110          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 110
gttctcgttt gaatatttgc tactaccacc aagatctgca cctgcggcgg              50

SEQ ID NO: 111          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 111
cgccctaggc ttcaaggctc accgcagcgg ccctcctact cgtcgcggcg              50

SEQ ID NO: 112          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 112
tccgggggcg gggagcgggg cgtgggcggg aggaggggag gaggcgtggg              50

SEQ ID NO: 113          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 113
aggaccccac accccgccg ccgccgccgc cgccgccctc cgacgcacac               50

SEQ ID NO: 114          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 114
gcgcgccgcc cccgccgctc ccgtccactc tcgactgccg gcgacggccg              50

SEQ ID NO: 115          moltype = DNA  length = 50
FEATURE                 Location/Qualifiers
```

```
misc_feature              1..50
                          note = DNA Probe
source                    1..50
                          mol_type = other DNA
                          organism = synthetic construct
SEQUENCE: 115
ctccagcgcc atccattttc agggctagtt gattcggcag gtgagttgtt              50

SEQ ID NO: 116            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 116
gattccgact tccatggcca ccgtcctgct gtctatatca accaacacct              50

SEQ ID NO: 117            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 117
gagcgtcggc atcgggcgcc ttaacccggc gttcggttca tcccgcagcg              50

SEQ ID NO: 118            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 118
aaaagtggcc cactaggcac tcgcattcca cgcccggctc cacgccagcg              50

SEQ ID NO: 119            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 119
ccatttaaag tttgagaata ggttgagatc gtttcggccc caagacctct              50

SEQ ID NO: 120            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 120
cggataaaac tgcgtggcgg gggtgcgtcg ggtctgcgag agcgccagct              50

SEQ ID NO: 121            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 121
tcggagggaa ccagctacta gatggttcga ttagtctttc gcccctatac              50

SEQ ID NO: 122            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 122
gatttgcacg tcaggaccgc tacggacctc caccagagtt tcctctggct              50

SEQ ID NO: 123            moltype = DNA   length = 50
```

```
FEATURE                 Location/Qualifiers
misc_feature            1..50
                        note = DNA Probe
source                  1..50
                        mol_type = other DNA
                        organism = synthetic construct
SEQUENCE: 123
atagttcacc atctttcggg tcctaacacg tgcgctcgtg ctccacctcc              50

SEQ ID NO: 124          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 124
agacgggccg gtggtgcgcc ctcggcggac tggagaggcc tcgggatccc              50

SEQ ID NO: 125          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 125
cgcgccggcc ttcaccttca ttgcgccacg gcggctttcg tgcgagcccc              50

SEQ ID NO: 126          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 126
ttagactcct tggtccgtgt ttcaagacgg gtcgggtggg tagccgacgt              50

SEQ ID NO: 127          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 127
gcgctcgctc cgccgtcccc ctcttcgggg gacgcgcgcg tggccccgag              50

SEQ ID NO: 128          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 128
cccgacggcg cgaccgcccc ggggcgcact gggacagtc cgccccgccc               50

SEQ ID NO: 129          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 129
gcaccccccc cgtcgccggg gcgggggcgc ggggaggagg ggtgggagag              50

SEQ ID NO: 130          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 130
aggggtggcc cggccccccc acgaggagac gccggcgcgc ccccgcgggg              50
```

| | | |
|---|---|---|
| SEQ ID NO: 131<br>FEATURE<br>misc_feature<br><br>source | moltype = DNA   length = 50<br>Location/Qualifiers<br>1..50<br>note = DNA Probe<br>1..50<br>mol_type = other DNA<br>organism = synthetic construct | |
| SEQUENCE: 131<br>ggggattccc cgcggggtg gcgccggga gggggagag cgcggcgacg | | 50 |
| SEQ ID NO: 132<br>FEATURE<br>misc_feature<br><br>source | moltype = DNA   length = 50<br>Location/Qualifiers<br>1..50<br>note = DNA Probe<br>1..50<br>mol_type = other DNA<br>organism = synthetic construct | |
| SEQUENCE: 132<br>gccccgggat tcggcgagtg ctgctgccgg gggggctgta acactcgggg | | 50 |
| SEQ ID NO: 133<br>FEATURE<br>misc_feature<br><br>source | moltype = DNA   length = 50<br>Location/Qualifiers<br>1..50<br>note = DNA Probe<br>1..50<br>mol_type = other DNA<br>organism = synthetic construct | |
| SEQUENCE: 133<br>ccgcccccgc cgccgccgcc accgccgccg ccgccgccgc cccgacccgc | | 50 |
| SEQ ID NO: 134<br>FEATURE<br>misc_feature<br><br>source | moltype = DNA   length = 50<br>Location/Qualifiers<br>1..50<br>note = DNA Probe<br>1..50<br>mol_type = other DNA<br>organism = synthetic construct | |
| SEQUENCE: 134<br>aggacgcggg gccggggggc ggagacgggg gaggaggagg acggacggac | | 50 |
| SEQ ID NO: 135<br>FEATURE<br>misc_feature<br><br>source | moltype = DNA   length = 50<br>Location/Qualifiers<br>1..50<br>note = DNA Probe<br>1..50<br>mol_type = other DNA<br>organism = synthetic construct | |
| SEQUENCE: 135<br>agccaccttc cccgccgggc cttcccagcc gtcccggagc cggtcgcggc | | 50 |
| SEQ ID NO: 136<br>FEATURE<br>misc_feature<br><br>source | moltype = DNA   length = 50<br>Location/Qualifiers<br>1..50<br>note = DNA Probe<br>1..50<br>mol_type = other DNA<br>organism = synthetic construct | |
| SEQUENCE: 136<br>aaatgcgccc ggcggcggcc ggtcgccggt cgggggacgg tccccgccg | | 50 |
| SEQ ID NO: 137<br>FEATURE<br>misc_feature<br><br>source | moltype = DNA   length = 50<br>Location/Qualifiers<br>1..50<br>note = DNA Probe<br>1..50<br>mol_type = other DNA<br>organism = synthetic construct | |
| SEQUENCE: 137<br>ccgcccgccc accccgcac ccgccggagc ccgccccctc cggggaggag | | 50 |
| SEQ ID NO: 138<br>FEATURE<br>misc_feature<br><br>source | moltype = DNA   length = 50<br>Location/Qualifiers<br>1..50<br>note = DNA Probe<br>1..50<br>mol_type = other DNA<br>organism = synthetic construct | |
| SEQUENCE: 138<br>gggaagggag ggcgggtgga ggggtcggga ggaacggggg gcgggaaaga | | 50 |

```
SEQ ID NO: 139          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 139
acacggccgg acccgccgcc gggttgaatc ctccgggcgg actgcgcgga              50

SEQ ID NO: 140          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 140
tcttaacggt ttcacgccct cttgaactct ctcttcaaag ttcttttcaa              50

SEQ ID NO: 141          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 141
cttgttgact atcggtctcg tgccggtatt tagccttaga tggagtttac              50

SEQ ID NO: 142          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 142
gcattcccaa gcaacccgac tccgggaaga cccgggcgcg cgccggccgc              50

SEQ ID NO: 143          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 143
gtccacgggc tgggcctcga tcagaaggac ttgggccccc cacgagcggc              50

SEQ ID NO: 144          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 144
ttccgtacgc cacatgtccc gcgccccgcg gggcggggat tcggcgctgg              50

SEQ ID NO: 145          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 145
ctcgccgtta ctgagggaat cctggttagt ttcttttcct ccgctgacta              50

SEQ ID NO: 146          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 146
```

```
gcgggtcgcc acgtctgatc tgaggtcgcg tctcggaggg ggacgggccg          50

SEQ ID NO: 147          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 147
aagcgacgct cagacaggcg tagccccggg aggaacccgg ggccgcaagt          50

SEQ ID NO: 148          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 148
gcagctagct gcgttcttca tcgacgcacg agccgagtga tccaccgcta          50

SEQ ID NO: 149          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 149
aaagcctaca gcacccggta ttcccaggcg gtctcccatc caagtactaa          50

SEQ ID NO: 150          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 150
ttccgagatc agacgagatc gggcgcgttc aggGtggtat ggccgtagac          50

SEQ ID NO: 151          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 151
gccgcccact cagactttat tcaaagacca cggGGgtacg ggtgcaggaa          50

SEQ ID NO: 152          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 152
gggggaggcc aaggggcaa gaagcatggc caccgaggct ccagcttaac           50

SEQ ID NO: 153          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 153
gcacggtgct cacagaagcc aggaacttgt ccagggaggc gtgcaccgca          50

SEQ ID NO: 154          moltype = DNA  length = 50
FEATURE                 Location/Qualifiers
misc_feature            1..50
                        note = DNA Probe
source                  1..50
                        mol_type = other DNA
                        organism = synthetic construct
```

SEQUENCE: 154
gggaggtggg cggccagggt caccagcagg cagtggctta ggagcttgaa                50

SEQ ID NO: 155           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 155
ccgaagcttg tgcgcgtgca ggtcgctcag ggcggacagc gcgttgggca                50

SEQ ID NO: 156           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 156
ccacggcgtt ggtcagcgcg tcggccacct tcttgccgtg gcccttaacc                50

SEQ ID NO: 157           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 157
ctcaggtcga agtgcgggaa gtaggtcttg gtggtgggga aggacaggaa                50

SEQ ID NO: 158           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 158
ctccgcacca tactcgccag cgtgcgcgcc gaccttaccc caggcggcct                50

SEQ ID NO: 159           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 159
cggcaggaga cagcaccatg gtgggttctc tctgagtctg tggggaccag                50

SEQ ID NO: 160           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 160
gaggggagga gggcccgttg ggaggcccag cggcaggag gaacggctac                 50

SEQ ID NO: 161           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 161
acggtatttg gaggtcagca cggtgctcac agaagccagg aacttgtcca                50

SEQ ID NO: 162           moltype = DNA   length = 50
FEATURE                  Location/Qualifiers
misc_feature             1..50
                         note = DNA Probe
source                   1..50
                         mol_type = other DNA

```
                        organism = synthetic construct
SEQUENCE: 162
cagggggtgaa ctcggcgggg aggtgggcgg ccagggtcac cagcaggcag              50

SEQ ID NO: 163          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 163
aagttgaccg ggtccacccg aagcttgtgc gcgtgcaggt cgctcagggc              50

SEQ ID NO: 164          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 164
catgtcgtcc acgtgcgcca cggcgttggt cagcgcgtcg gccaccttct              50

SEQ ID NO: 165          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 165
cctgggcaga gccgtggctc aggtcgaagt gcgggaagta ggtcttggtg              50

SEQ ID NO: 166          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 166
aacatcctct ccagggcctc cgcaccatac tcgccagcgt gcgcgccgac              50

SEQ ID NO: 167          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 167
cttgacgttg gtcttgtcgg caggagacag caccatggtg ggttctctct              50

SEQ ID NO: 168          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 168
gcaatgaaaa taaatgttttt ttattaggca gaatccagat gctcaaggcc             50

SEQ ID NO: 169          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 169
cagtttagta gttggactta gggaacaaag gaacctttaa tagaaattgg              50

SEQ ID NO: 170          moltype = DNA   length = 50
FEATURE                 Location/Qualifiers
misc_feature            1..50
                        note = DNA Probe
source                  1..50
```

```
                        mol_type = other DNA
                        organism = synthetic construct
SEQUENCE: 170
gcttagtgat acttgtgggc caggcatta gccacaccag ccaccacttt        50

SEQ ID NO: 171          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 171
cactggtggg gtgaattctt tgccaaagtg atgggccagc acacagacca        50

SEQ ID NO: 172          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 172
gcctgaagtt ctcaggatcc acgtgcagct tgtcacagtg cagctcactc        50

SEQ ID NO: 173          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 173
cccttgaggt tgtccaggtg agccaggcca tcactaaagg caccgagcac        50

SEQ ID NO: 174          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 174
cttcacctta gggttgccca taacagcatc aggagtggac agatccccaa        50

SEQ ID NO: 175          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 175
tctgggtcca agggtagacc accagcagcc tgcccagggc ctcaccacca        50

SEQ ID NO: 176          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 176
accttgcccc acagggcagt aacggcagac ttctcctcag gagtcagatg        50

SEQ ID NO: 177          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 177
gtgatctctc agcagaatag atttattatt tgtattgctt gcagaataaa        50

SEQ ID NO: 178          moltype = DNA   length = 50
FEATURE                 Location/Qualifiers
misc_feature            1..50
                        note = DNA Probe
```

```
                        source           1..50
                                         mol_type = other DNA
                                         organism = synthetic construct
SEQUENCE: 178
ctctgaatca tgggcagtga gctcagtggt atctggagga cagggcactg                    50

SEQ ID NO: 179          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 179
atcttctgcc aggaagcctg cacctcaggg gtgaattctt tgccgaaatg                    50

SEQ ID NO: 180          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 180
caccagcaca tttcccagga gcttgaagtt ctcaggatcc acatgcagct                    50

SEQ ID NO: 181          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 181
cactcagctg ggcaaaggtg cccttgagat catccaggtg ctttgtggca                    50

SEQ ID NO: 182          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 182
agcaccttct tgccatgtgc cttgactttg gggttgccca tgatggcaga                    50

SEQ ID NO: 183          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 183
gccaaagctg tcaaagaacc tctgggtcca tgggtagaca accaggagcc                    50

SEQ ID NO: 184          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 184
ctccagcatc ttccacattc accttgcccc acaggcttgt gatagtagcc                    50

SEQ ID NO: 185          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 185
aaatgaccca tggcgtctgg actaggagct tattgataac ctcagacgtt                    50

SEQ ID NO: 186          moltype = DNA   length = 50
FEATURE                 Location/Qualifiers
misc_feature            1..50
```

```
                          note = DNA Probe
source                    1..50
                          mol_type = other DNA
                          organism = synthetic construct
SEQUENCE: 186
gtgatctctt agcagaatag atttattatt tgattgcttg cagaataaag              50

SEQ ID NO: 187            moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 187
tctgcatcat gggcagtgag ctcagtggta tctggaggac agggcactgg              50

SEQ ID NO: 188            moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 188
tcttctgcca ggaagcctgc acctcagggg tgaattcttt gccgaaatgg              50

SEQ ID NO: 189            moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 189
accagcacat ttcccaggag cttgaagttc tcaggatcca catgcagctt              50

SEQ ID NO: 190            moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 190
actcagctgg gcaaaggtgc ccttgagatc atccaggtgc tttatggcat              50

SEQ ID NO: 191            moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 191
gcaccttctt gccatgtgcc ttgactttgg ggttgcccat gatggcagag              50

SEQ ID NO: 192            moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 192
ccaaagctgt caaagaacct ctgggtccat gggtagacaa ccaggagcct              50

SEQ ID NO: 193            moltype = DNA  length = 50
FEATURE                   Location/Qualifiers
misc_feature              1..50
                          note = DNA Probe
source                    1..50
                          mol_type = other DNA
                          organism = synthetic construct
SEQUENCE: 193
tccagcatct tccacattca ccttgcccca caggcttgtg atagtagcct              50

SEQ ID NO: 194            moltype = DNA  length = 50
FEATURE                   Location/Qualifiers
```

```
misc_feature            1..50
                        note = DNA Probe
source                  1..50
                        mol_type = other DNA
                        organism = synthetic construct
SEQUENCE: 194
aatgacccat ggcgtctgga ctaggagctt attgataacc tcagacgttc            50

SEQ ID NO: 195          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 195
atgcctggca gttccctact ctcgcatggg gagaccccac actaccatcg            50

SEQ ID NO: 196          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 196
acttctgagt tcggcatggg gtcaggtggg accaccgcgc tacggccgcc            50

SEQ ID NO: 197          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 197
ggttaccttg ttacgacttc accccagtca tgaatcacaa agtggtaagt            50

SEQ ID NO: 198          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 198
aagctaccta cttcttttgc aacccactcc catggtgtga cgggcggtgt            50

SEQ ID NO: 199          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 199
acgtattcac cgtggcattc tgatccacga ttactagcga ttccgacttc            50

SEQ ID NO: 200          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 200
agactccaat ccggactacg acgcacttta tgaggtccgc ttgctctcgc            50

SEQ ID NO: 201          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 201
tgtatgcgcc attgtagcac gtgtgtagcc ctggtcgtaa gggccatgat            50

SEQ ID NO: 202          moltype = DNA   length = 50
```

```
FEATURE                 Location/Qualifiers
misc_feature            1..50
                        note = DNA Probe
source                  1..50
                        mol_type = other DNA
                        organism = synthetic construct
SEQUENCE: 202
ccaccttcct ccagtttatc actggcagtc tcctttgagt tcccggccgg               50

SEQ ID NO: 203          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 203
ggataagggt tgcgctcgtt gcgggactta acccaacatt tcacaacacg               50

SEQ ID NO: 204          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 204
tgcagcacct gtctcacggt tcccgaaggc acattctcat ctctgaaaac               50

SEQ ID NO: 205          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 205
gaccaggtaa ggttcttcgc gttgcatcga attaaaccac atgctccacc               50

SEQ ID NO: 206          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 206
cgtcaattca tttgagtttt aaccttgcgg ccgtactccc caggcggtcg               50

SEQ ID NO: 207          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 207
tccggaagcc acgcctcaag ggcacaacct ccaagtcgac atcgtttacg               50

SEQ ID NO: 208          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 208
gtatctaatc ctgtttgctc cccacgcttt cgcactgagc gtcagtcttc               50

SEQ ID NO: 209          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 209
ttcgccaccg gtattcctcc agatctctac gcatttcacc gctacacctg               50
```

```
SEQ ID NO: 210            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 210
ctacgagact caagcttgcc agtatcagat gcagttccca ggttgagccc            50

SEQ ID NO: 211            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 211
gacttaacaa accgcctgcg tgcgctttac gcccagtaat tccgattaac            50

SEQ ID NO: 212            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 212
attaccgcgg ctgctggcac ggagttagcc ggtgcttctt ctgcgggtaa            50

SEQ ID NO: 213            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 213
gtattaactt tactcccttc ctccccgctg aaagtacttt acaacccgaa            50

SEQ ID NO: 214            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 214
cgcggcatgg ctgcatcagg cttgcgccca ttgtgcagta ttccccactg            50

SEQ ID NO: 215            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 215
gtctggaccg tgtctcagtt ccagtgtggc tggtcatcct ctcagaccag            50

SEQ ID NO: 216            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 216
taggtgagcc gttaccccac ctactagcta atcccatctg ggcacatccg            50

SEQ ID NO: 217            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 217
aaggtccccc tctttggtct tgcgacgtta tgcggtatta gctaccgttt            50
```

```
SEQ ID NO: 218            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 218
ctccatcagg cagtttccca gacattactc acccgtccgc cactcgtcag              50

SEQ ID NO: 219            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 219
aaggttaagc ctcacggttc attagtaccg gttagctcaa cgcatcgctg              50

SEQ ID NO: 220            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 220
cctatcaacg tcgtcgtctt caacgttcct tcaggaccct taaagggtca              50

SEQ ID NO: 221            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 221
ggggcaagtt tcgtgcttag atgctttcag cacttatctc ttccgcattt              50

SEQ ID NO: 222            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 222
ccattggcat gacaacccga acaccagtga tgcgtccact ccggtcctct              50

SEQ ID NO: 223            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 223
cccccctcagt tctccagcgc ccacggcaga tagggaccga actgtctcac             50

SEQ ID NO: 224            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 224
gctcgcgtac cactttaaat ggcgaacagc catacccttg ggacctactt              50

SEQ ID NO: 225            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 225
```
atgagccgac atcgaggtgc caaacaccgc cgtcgatatg aactcttggg    50

SEQ ID NO: 226         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 226
atccccggag tacctttat ccgttgagcg atggcccttc cattcagaac    50

SEQ ID NO: 227         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 227
acctgctttc gcacctgctc gcgccgtcac gctcgcagtc aagctggctt    50

SEQ ID NO: 228         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 228
cctcctgatg tccgaccagg attagccaac cttcgtgctc ctccgttact    50

SEQ ID NO: 229         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 229
gccccagtca aactacccac cagacactgt ccgcaacccg gattacgggt    50

SEQ ID NO: 230         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 230
aaacattaaa gggtggtatt tcaaggtcgg ctccatgcag actggcgtcc    50

SEQ ID NO: 231         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 231
ccacctatcc tacacatcaa ggctcaatgt tcagtgtcaa gctatagtaa    50

SEQ ID NO: 232         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 232
ttccgtcttg ccgcgggtac actgcatctt cacagcgagt tcaatttcac    50

SEQ ID NO: 233         moltype = DNA   length = 50
FEATURE                Location/Qualifiers
misc_feature           1..50
                       note = DNA Probe
source                 1..50
                       mol_type = other DNA
                       organism = synthetic construct

```
SEQUENCE: 233
gacagcctgg ccatcattac gccattcgtg caggtcggaa cttacccgac         50

SEQ ID NO: 234          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 234
cttaggaccg ttatagttac ggccgccgtt taccggggct tcgatcaaga         50

SEQ ID NO: 235          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 235
accccatcaa ttaaccttcc ggcaccgggc aggcgtcaca ccgtatacgt         50

SEQ ID NO: 236          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 236
cacagtgctg tgttttaat aaacagttgc agccagctgg tatcttcgac          50

SEQ ID NO: 237          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 237
ccgcgaggga cctcacctac atatcagcgt gccttctccc gaagttacgg         50

SEQ ID NO: 238          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 238
ttccttcacc cgagttctct caagcgcctt ggtattctct acctgaccac         50

SEQ ID NO: 239          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 239
gtacgatttg atgttacctg atgcttagag gcttttcctg gaagcagggc         50

SEQ ID NO: 240          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 240
accgtagtgc ctcgtcatca cgcctcagcc ttgattttcc ggatttgcct         50

SEQ ID NO: 241          moltype = DNA  length = 50
FEATURE                 Location/Qualifiers
misc_feature            1..50
                        note = DNA Probe
source                  1..50
                        mol_type = other DNA
```

```
                        organism = synthetic construct
SEQUENCE: 241
acgcttaaac cgggacaacc gtcgcccggc caacatagcc ttctccgtcc              50

SEQ ID NO: 242          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 242
accaagtaca ggaatattaa cctgtttccc atcgactacg cctttcggcc              50

SEQ ID NO: 243          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 243
actcaccctg ccccgattaa cgttggacag gaacccttgg tcttccggcg              50

SEQ ID NO: 244          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 244
cgctttatcg ttacttatgt cagcattcgc acttctgata cctccagcat              50

SEQ ID NO: 245          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 245
ttcgcaggct tacagaacgc tccoctaccc aacaacgcat aagcgtcgct              50

SEQ ID NO: 246          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 246
catggtttag ccccgttaca tcttccgcgc aggccgactc gaccagtgag              50

SEQ ID NO: 247          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 247
taaatgatgg ctgcttctaa gccaacatcc tggctgtctg ggccttccca              50

SEQ ID NO: 248          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 248
aaccatgact ttgggacctt agctggcggt ctgggttgtt tccctcttca              50

SEQ ID NO: 249          moltype = DNA  length = 50
FEATURE                 Location/Qualifiers
misc_feature            1..50
                        note = DNA Probe
source                  1..50
```

```
                        mol_type = other DNA
                        organism = synthetic construct
SEQUENCE: 249
cccgccgtgt gtctcccgtg ataacattct ccggtattcg cagtttgcat            50

SEQ ID NO: 250          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 250
ggatgacccc cttgccgaaa cagtgctcta cccccggaga tgaattcacg            50

SEQ ID NO: 251          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 251
agctttcggg gagaaccagc tatctcccgg tttgattggc ctttcacccc            50

SEQ ID NO: 252          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 252
cgctaatttt tcaacattag tcggttcggt cctccagtta gtgttaccca            50

SEQ ID NO: 253          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 253
atggctagat caccgggttt cgggtctata ccctgcaact taacgcccag            50

SEQ ID NO: 254          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 254
ccttcggctc ccctattcgg ttaaccttgc tacagaaatt aagtcgctga            50

SEQ ID NO: 255          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 255
gtacgcagtc acacgcctaa gcgtgctccc actgcttgta cgtacacggt            50

SEQ ID NO: 256          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 256
actccccctcg ccggggttct tttcgccttt ccctcacggt actggttcac           50

SEQ ID NO: 257          moltype = DNA   length = 50
FEATURE                 Location/Qualifiers
misc_feature            1..50
                        note = DNA Probe
```

```
source                    1..50
                          mol_type = other DNA
                          organism = synthetic construct
SEQUENCE: 257
agtatttagc cttggaggat ggtcccccca tattcagaca ggataccacg              50

SEQ ID NO: 258            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 258
atcgagctca cagcatgtgc attttttgtgt acggggctgt caccctgtat              50

SEQ ID NO: 259            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 259
acgcttccac taacacacac actgattcag gctctgggct gctccccgtt              50

SEQ ID NO: 260            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 260
ggggaatctc ggttgatttc ttttcctcgg ggtacttaga tgtttcagtt              50

SEQ ID NO: 261            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 261
attaacctat ggattcagtt aatgatagtg tgtcgaaaca cactgggttt              50

SEQ ID NO: 262            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 262
gccggttata acggttcata tcaccttacc gacgcttatc gcagattagc              50

SEQ ID NO: 263            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 263
gcttggcggc gtcctactct cacaggggga accccccgac taccatcggc              50

SEQ ID NO: 264            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 264
ttccgtgttc ggtatgggaa cgggtgtgac ctcttcgcta tcgccaccaa              50

SEQ ID NO: 265            moltype = DNA   length = 50
FEATURE                   Location/Qualifiers
misc_feature              1..50
```

```
                    note = DNA Probe
source              1..50
                    mol_type = other DNA
                    organism = synthetic construct
SEQUENCE: 265
tagaaaggag gtgatccagc cgcaccttcc gatacggcta ccttgttacg              50

SEQ ID NO: 266      moltype = DNA  length = 50
FEATURE             Location/Qualifiers
misc_feature        1..50
                    note = DNA Probe
source              1..50
                    mol_type = other DNA
                    organism = synthetic construct
SEQUENCE: 266
tctgtcccac cttcggcggc tggctcctaa aaggttacct caccgacttc              50

SEQ ID NO: 267      moltype = DNA  length = 50
FEATURE             Location/Qualifiers
misc_feature        1..50
                    note = DNA Probe
source              1..50
                    mol_type = other DNA
                    organism = synthetic construct
SEQUENCE: 267
tcgtggtgtg acgggcggtg tgtacaaggc ccgggaacgt attcaccgcg              50

SEQ ID NO: 268      moltype = DNA  length = 50
FEATURE             Location/Qualifiers
misc_feature        1..50
                    note = DNA Probe
source              1..50
                    mol_type = other DNA
                    organism = synthetic construct
SEQUENCE: 268
attactagcg attccagctt cacgcagtcg agttgcagac tgcgatccga              50

SEQ ID NO: 269      moltype = DNA  length = 50
FEATURE             Location/Qualifiers
misc_feature        1..50
                    note = DNA Probe
source              1..50
                    mol_type = other DNA
                    organism = synthetic construct
SEQUENCE: 269
gtgggattgg cttaacctcg cggtttcgct gccctttgtt ctgtccattg              50

SEQ ID NO: 270      moltype = DNA  length = 50
FEATURE             Location/Qualifiers
misc_feature        1..50
                    note = DNA Probe
source              1..50
                    mol_type = other DNA
                    organism = synthetic construct
SEQUENCE: 270
ccaggtcata aggggcatga tgatttgacg tcatccccac cttcctccgg              50

SEQ ID NO: 271      moltype = DNA  length = 50
FEATURE             Location/Qualifiers
misc_feature        1..50
                    note = DNA Probe
source              1..50
                    mol_type = other DNA
                    organism = synthetic construct
SEQUENCE: 271
caccttagag tgcccaactg aatgctggca actaagatca agggttgcgc              50

SEQ ID NO: 272      moltype = DNA  length = 50
FEATURE             Location/Qualifiers
misc_feature        1..50
                    note = DNA Probe
source              1..50
                    mol_type = other DNA
                    organism = synthetic construct
SEQUENCE: 272
acccaacatc tcacgacacg agctgacgac aaccatgcac cacctgtcac              50

SEQ ID NO: 273      moltype = DNA  length = 50
FEATURE             Location/Qualifiers
```

```
misc_feature            1..50
                        note = DNA Probe
source                  1..50
                        mol_type = other DNA
                        organism = synthetic construct
SEQUENCE: 273
gacgtcctat ctctaggatt gtcagaggat gtcaagacct ggtaaggttc          50

SEQ ID NO: 274          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 274
attaaaccac atgctccacc gcttgtgcgg gcccccgtca attcctttga          50

SEQ ID NO: 275          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 275
ccgtactccc caggcggagt gcttaatgcg ttagctgcag cactaagggg          50

SEQ ID NO: 276          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 276
acttagcact catcgtttac ggcgtggact accagggtat ctaatcctgt          50

SEQ ID NO: 277          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 277
tcgctcctca gcgtcagtta cagaccagag agtcgccttc gccactggtg          50

SEQ ID NO: 278          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 278
acgcatttca ccgctacacg tggaattcca ctctcctctt ctgcactcaa          50

SEQ ID NO: 279          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 279
atgaccctcc ccggttgagc cggggqcttt cacatcagac ttaagaaacc          50

SEQ ID NO: 280          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 280
acgcccaata attccggaca acgcttgcca cctacgtatt accgcggctg          50

SEQ ID NO: 281          moltype = DNA  length = 50
```

```
FEATURE                 Location/Qualifiers
misc_feature            1..50
                        note = DNA Probe
source                  1..50
                        mol_type = other DNA
                        organism = synthetic construct
SEQUENCE: 281
ccgtggcttt ctggttaggt accgtcaagg taccgcccta ttcgaacggt          50

SEQ ID NO: 282          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 282
acaacagagc tttacgatcc gaaaaccttc atcactcacg cggcgttgct          50

SEQ ID NO: 283          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 283
ccattgcgga agattcccta ctgctgcctc ccgtaggagt ctgggccgtg          50

SEQ ID NO: 284          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 284
ggccgatcac cctctcaggt cggctacgca tcgtcgcctt ggtgagccgt          50

SEQ ID NO: 285          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 285
ctaatgcgcc gcgggtccat ctgtaagtgg tagccgaagc cacctttat          50

SEQ ID NO: 286          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 286
ttcaaacaac catccggtat tagccccggt ttcccggagt tatcccagtc          50

SEQ ID NO: 287          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 287
ccacgtgtta ctcacccgtc cgccgctaac atcagggagc aagctcccat          50

SEQ ID NO: 288          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 288
gcatgtatta ggcacgccgc cagcgttcgt cctgagccag gatcaaactc          50
```

```
SEQ ID NO: 289          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 289
tggttaagtc ctcgatcgat tagtatctgt cagctccatg tgtcgccaca              50

SEQ ID NO: 290          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 290
tatcaacctg atcatctttc agggatctta cttccttgcg gaatgggaaa              50

SEQ ID NO: 291          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 291
ggcttcatgc ttagatgctt tcagcactta tcccgtccgc acatagctac              50

SEQ ID NO: 292          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 292
gcagaacaac tggtacacca gcggtgcgtc catcccggtc ctctcgtact              50

SEQ ID NO: 293          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 293
caaatttcct gcgcccgcga cggataggga ccgaactgtc tcacgacgtt              50

SEQ ID NO: 294          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 294
gtaccgcttt aatgggcgaa cagcccaacc cttgggactg actacagccc              50

SEQ ID NO: 295          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 295
cgacatcgag gtgccaaacc tccccgtcga tgtggactct tggggagat               50

SEQ ID NO: 296          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 296
ggggtagctt ttatccgttg agcgatggcc cttccatgcg gaaccaccgg              50
```

```
SEQ ID NO: 297          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 297
tttcgtccct gctcgacttg taggtctcgc agtcaagctc ccttgtgcct             50

SEQ ID NO: 298          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 298
gatttccaac cattctgagg gaacctttgg gcgcctccgt tacctttag              50

SEQ ID NO: 299          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 299
gtcaaactgc ccacctgaca ctgtctcccc gcccgataag ggcggcgggt             50

SEQ ID NO: 300          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 300
gccagggtag tatcccaccg atgcctccac cgaagctggc gctccggttt             50

SEQ ID NO: 301          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 301
atcctgtaca agctgtacca acattcaata tcaggctgca gtaaagctcc             50

SEQ ID NO: 302          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 302
cctgtcgcgg gtaacctgca tcttcacagg tactataatt tcaccgagtc             50

SEQ ID NO: 303          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 303
gcccagatcg ttgcgccttt cgtgcgggtc ggaacttacc cgacaaggaa             50

SEQ ID NO: 304          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 304
```
accgttatag ttacggccgc cgtttactgg ggcttcaatt cgcaccttcg            50

SEQ ID NO: 305         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 305
cctcttaacc ttccagcacc gggcaggcgt cagcccctat acttcgcctt            50

SEQ ID NO: 306         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 306
cctgtgtttt tgctaaacag tcgcctgggc ctattcactg cggctctctc            50

SEQ ID NO: 307         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 307
cagagcaccc cttctcccga agttacgggg tcattttgcc gagttcctta            50

SEQ ID NO: 308         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 308
atcaccttag gattctctcc tcgcctacct gtgtcggttt gcggtacggg            50

SEQ ID NO: 309         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 309
tagaggcttt tcttggcagt gtggaatcag gaacttcgct actatatttc            50

SEQ ID NO: 310         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 310
tcagccttat gggaaacgga tttgcctatt tcccagccta actgcttgga            50

SEQ ID NO: 311         moltype = DNA   length = 50
FEATURE                Location/Qualifiers
misc_feature           1..50
                       note = DNA Probe
source                 1..50
                       mol_type = other DNA
                       organism = synthetic construct
SEQUENCE: 311
ccgcgcttac cctatcctcc tgcgtccccc cattgctcaa atggtgagga            50

SEQ ID NO: 312         moltype = DNA   length = 50
FEATURE                Location/Qualifiers
misc_feature           1..50
                       note = DNA Probe
source                 1..50
                       mol_type = other DNA
                       organism = synthetic construct

```
SEQUENCE: 312
tcaacctgtt gtccatcgcc tacgcctttc ggcctcggct taggtcccga                50

SEQ ID NO: 313           moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 313
cgagccttcc tcaggaaacc ttaggcattc ggtggagggg attctcaccc                50

SEQ ID NO: 314           moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 314
taccggcatt ctcacttcta agcgctccac cagtccttcc ggtctggctt                50

SEQ ID NO: 315           moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 315
gctctcctac cactgttcga agaacagtcc gcagcttcgg tgatacgttt                50

SEQ ID NO: 316           moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 316
tcggcgcaga gtcactcgac cagtgagcta ttacgcactc tttaaatggt                50

SEQ ID NO: 317           moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 317
aacatcctgg ttgtctaagc aactccacat cctttccac ttaacgtata                 50

SEQ ID NO: 318           moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 318
tggcggtctg ggctgtttcc ctttcgacta cggatcttat cactcgcagt                50

SEQ ID NO: 319           moltype = DNA  length = 50
FEATURE                  Location/Qualifiers
misc_feature             1..50
                         note = DNA Probe
source                   1..50
                         mol_type = other DNA
                         organism = synthetic construct
SEQUENCE: 319
aagtcattgg cattcggagt ttgactgaat tcggtaaccc ggtaggggcc                50

SEQ ID NO: 320           moltype = DNA  length = 50
FEATURE                  Location/Qualifiers
misc_feature             1..50
                         note = DNA Probe
source                   1..50
                         mol_type = other DNA
```

```
                            organism = synthetic construct
SEQUENCE: 320
gctctacctc caagactctt accttgaggc tagccctaaa gctatttcgg              50

SEQ ID NO: 321          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 321
tccaggttcg attggcattt cacccctacc cacacctcat ccccgcactt              50

SEQ ID NO: 322          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 322
ttcgggcctc cattcagtgt tacctgaact tcaccctgga catgggtaga              50

SEQ ID NO: 323          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 323
tctacgacca cgtactcatg cgccctattc agactcgctt tcgctgcggc              50

SEQ ID NO: 324          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 324
taaccttgca cgggatcgta actcgccggt tcattctaca aaaggcacgc              50

SEQ ID NO: 325          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 325
ggctctgact acttgtaggc acacggtttc aggatctctt tcactcccct              50

SEQ ID NO: 326          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 326
acctttccct cacggtactg gttcactatc ggtcactagg gagtatttag              50

SEQ ID NO: 327          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 327
ctcccggatt ccgacggaat ttcacgtgtt ccgccgtact caggatccac              50

SEQ ID NO: 328          moltype = DNA   length = 50
FEATURE                 Location/Qualifiers
misc_feature            1..50
                        note = DNA Probe
source                  1..50
```

```
                        mol_type = other DNA
                        organism = synthetic construct
SEQUENCE: 328
gttttgacta cagggctgtt acctcctatg gcgggccttt ccagacctct                 50

SEQ ID NO: 329          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 329
ctttgtaact ccgtacagag tgtcctacaa ccccaagagg caagcctctt                 50

SEQ ID NO: 330          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 330
cgtttcgctc gccgctactc agggaatcgc atttgctttc tcttcctccg                 50

SEQ ID NO: 331          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 331
cagttccccg ggtctgcctt ctcatatcct atgaattcag atatggatac                 50

SEQ ID NO: 332          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 332
ggtgggtttc cccattcgga aatctccgga tcaaagcttg cttacagctc                 50

SEQ ID NO: 333          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 333
tgttcgtccc gtccttcatc ggctcctagt gccaaggcat ccaccgtgcg                 50

SEQ ID NO: 334          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 334
aaactagatt cgaatataac aaaacattac atcctcatcc aatccctttt                 50

SEQ ID NO: 335          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 335
gcggtgtgtg caaggagcag ggacgtattc accgcgcgat tgtgacacgc                 50

SEQ ID NO: 336          moltype = DNA   length = 50
FEATURE                 Location/Qualifiers
misc_feature            1..50
                        note = DNA Probe
```

```
                          source          1..50
                                          mol_type = other DNA
                                          organism = synthetic construct
SEQUENCE: 336
gcctttcggc gtcggaaccc attgtctcag ccattgtagc ccgcgtgttg          50

SEQ ID NO: 337            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 337
gcatacggac ctaccgtcgt ccactccttc ctcctattta tcataggcgg          50

SEQ ID NO: 338            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 338
cggcatccaa aaaaggatcc gctggtaact aagagcgtgg gtctcgctcg          50

SEQ ID NO: 339            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 339
caacctggct atcatacagc tgtcgcctct ggtgagatgt ccggcgttga          50

SEQ ID NO: 340            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 340
aggctccacg cgttgtggtg ctcccccgcc aattcccttta agtttcagtc          50

SEQ ID NO: 341            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 341
ccaggcggcg gacttaacag cttcccttcg gcactgggac agctcaaagc          50

SEQ ID NO: 342            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 342
tccgcatcgt ttacagctag gactacccgg gtatctaatc cggttcgcgc          50

SEQ ID NO: 343            moltype = DNA   length = 50
FEATURE                   Location/Qualifiers
misc_feature              1..50
                          note = DNA Probe
source                    1..50
                          mol_type = other DNA
                          organism = synthetic construct
SEQUENCE: 343
ttcccacagt taagctgcag gatttcacca gagacttatt aaaccggcta          50

SEQ ID NO: 344            moltype = DNA   length = 50
FEATURE                   Location/Qualifiers
misc_feature              1..50
```

```
                        note = DNA Probe
source                  1..50
                        mol_type = other DNA
                        organism = synthetic construct
SEQUENCE: 344
ctcttattcc aaaagctctt tacactaatg aaaagccatc ccgttaagaa              50

SEQ ID NO: 345          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 345
cccccgtcgc gatttctcac attgcggagg tttcgcgcct gctgcacccc              50

SEQ ID NO: 346          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 346
ttgtctcagg ttccatctcc gggctcttgc tctcacaacc cgtaccgatc              50

SEQ ID NO: 347          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 347
cattacctaa ccaactacct aatcggccgc agacccatcc ttaggcgaaa              50

SEQ ID NO: 348          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 348
aaaccattac aggaataatt gcctatccag tattatcccc agtttcccag              50

SEQ ID NO: 349          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 349
aagggtaggt tatccacgtg ttactgagcc gtacgccacg agcctaaact              50

SEQ ID NO: 350          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 350
acctagcgcg tagctgcccg gcactgcctt atcagacaac cggtcgacca              50

SEQ ID NO: 351          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 351
cgttcctctc gtactggagc caccttcccc tcagactact aacacatcca              50

SEQ ID NO: 352          moltype = DNA  length = 50
FEATURE                 Location/Qualifiers
```

```
misc_feature            1..50
                        note = DNA Probe
source                  1..50
                        mol_type = other DNA
                        organism = synthetic construct
SEQUENCE: 352
cctgtctcac gacggtctaa acccagctca cgttcccctt taatgggcga         50

SEQ ID NO: 353          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 353
ggtgctgctg cacacccagg atggaaagaa ccgacatcga agtagcaagc         50

SEQ ID NO: 354          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 354
ggctcttgcc tgcgaccacc cagttatccc cgaggtagtt tttctgtcat         50

SEQ ID NO: 355          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 355
aggaggactc tgaggttcgc taggcccggc tttcgcctct ggatttcttg         50

SEQ ID NO: 356          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 356
caaagtaagt tagaaacaca gtcataagaa agtggtgtct caagaacgaa         50

SEQ ID NO: 357          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 357
gacttataat cgaattctcc cacttacact gcatacctat aaccaagctt         50

SEQ ID NO: 358          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 358
gtaaaactct acgggtctt cgcttcccaa tggaagactc tggcttgtgc          50

SEQ ID NO: 359          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 359
tcactaagtt ctagctaggg acagtgggga cctcgttcta ccattcatgc         50

SEQ ID NO: 360          moltype = DNA  length = 50
```

```
FEATURE                 Location/Qualifiers
misc_feature            1..50
                        note = DNA Probe
source                  1..50
                        mol_type = other DNA
                        organism = synthetic construct
SEQUENCE: 360
cgacaaggca tttcgctacc ttaagagggt tatagttacc cccgccgttt            50

SEQ ID NO: 361          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 361
aactgaactc cagcttcacg tgccagcact gggcaggtgt cgccctctgt            50

SEQ ID NO: 362          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 362
ctagcagaga gctatgtttt tattaaacag tcgggccccc ctagtcactg            50

SEQ ID NO: 363          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 363
ttaaacgcc ttagcctact cagctagggg cacctgtgac ggatctcggt             50

SEQ ID NO: 364          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 364
acaaaactaa ctccctttc aaggactcca tgaatcagtt aaaccagtac             50

SEQ ID NO: 365          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 365
ataatgccta cacctggttc tcgctattac acctctcccc aggcttaaac            50

SEQ ID NO: 366          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 366
caatcctaca aaacatatct cgaagtgtca gaaattagcc ctcaacgtca            50

SEQ ID NO: 367          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 367
ctttgctgct actactacca ggatccacat acctgcaagg tccaaaggaa            50
```

```
SEQ ID NO: 368           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 368
caacccacac aggtcgccac tctacacaat caccaaaaaa aaggtgttcc           50

SEQ ID NO: 369           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 369
ggattaattc ccgtccattt taggtgcctc tgacctcgat gggtgatctg           50

SEQ ID NO: 370           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 370
agggtggctg cttctaagcc caccttccca ttgtcttggg ccaaagactc           50

SEQ ID NO: 371           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 371
gtatttaggg gccttaacca tagtctgagt tgtttctctt tcgggacaca           50

SEQ ID NO: 372           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 372
cctcactcca accttctacg acggtgacga gttcggagtt ttacagtacg           50

SEQ ID NO: 373           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 373
ccctaaacgt ccaattagtg ctctaccccg ccaccaacct ccagtcaggc           50

SEQ ID NO: 374           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 374
aatagatcga ccggcttcgg gtttcaatgc tgtgattcca ggccctatta           50

SEQ ID NO: 375           moltype = DNA   length = 50
FEATURE                  Location/Qualifiers
misc_feature             1..50
                         note = DNA Probe
source                   1..50
                         mol_type = other DNA
                         organism = synthetic construct
SEQUENCE: 375
acaacgctgc gggcatatcg gtttccctac gactacaagg ataaaaacct           50
```

```
SEQ ID NO: 376          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 376
acaaagaact ccctggcccg tgtttcaaga cggacgatgc aacactagtc           50

SEQ ID NO: 377          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 377
acaatgttac cactgattct ttcggaagaa ttcattcctt acgcgccaca           50

SEQ ID NO: 378          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 378
ctggtttcag gtactttca cccccctata ggggtacttt tcagcattcc            50

SEQ ID NO: 379          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 379
ctctatcggt cttgagacgt atttagaatt ggaagttgat gcctcccaca           50

SEQ ID NO: 380          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 380
atcaccctct acggttctaa aattccaaat aaaattcgat ttatcccacg           50

SEQ ID NO: 381          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 381
tctatacacc acatctccct aatattacta aaagggattc agtttgttct           50

SEQ ID NO: 382          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 382
gccgttacta acgacatcgc atattgcttt cttttcctcc gcctactaag           50

SEQ ID NO: 383          moltype = DNA  length = 50
FEATURE                 Location/Qualifiers
misc_feature            1..50
                        note = DNA Probe
source                  1..50
                        mol_type = other DNA
                        organism = synthetic construct
SEQUENCE: 383
```
gggttcccaa tcctacacgg atcaacacaa aaaaaatgtg ctaggaagtc    50

SEQ ID NO: 384          moltype = DNA   length = 50
FEATURE                 Location/Qualifiers
misc_feature            1..50
                        note = DNA Probe
source                  1..50
                        mol_type = other DNA
                        organism = synthetic construct
SEQUENCE: 384
actactggga tcgaaacgag accaggtata acccccatgc tatgaccgca    50

SEQ ID NO: 385          moltype = AA   length = 50
FEATURE                 Location/Qualifiers
source                  1..50
                        mol_type = protein
                        organism = Mus musculus
SEQUENCE: 385
GCGTATGCCT GGAGAATTGG AATTCTTGTT ACTCATACTA ACAGTGTTGC    50

SEQ ID NO: 386          moltype = AA   length = 50
FEATURE                 Location/Qualifiers
source                  1..50
                        mol_type = protein
                        organism = Mus musculus
SEQUENCE: 386
GATTAACCCA ATTTTAAGTT TAGGAAGTTG GTGTAAATTA TGGAATTAAT    50

SEQ ID NO: 387          moltype = AA   length = 50
FEATURE                 Location/Qualifiers
source                  1..50
                        mol_type = protein
                        organism = Mus musculus
SEQUENCE: 387
AGCTTGAACG CTTTCTTTAT TGGTGGCTGC TTTTAGGCCT ACAATGGTTA    50

SEQ ID NO: 388          moltype = AA   length = 50
FEATURE                 Location/Qualifiers
source                  1..50
                        mol_type = protein
                        organism = Mus musculus
SEQUENCE: 388
ATTATTCACT ATTAAAGGTT TTTTCCGTTC CAGAAGAGCT GTCCCTCTTT    50

SEQ ID NO: 389          moltype = AA   length = 50
FEATURE                 Location/Qualifiers
source                  1..50
                        mol_type = protein
                        organism = Mus musculus
SEQUENCE: 389
CTTACTTTTT GATTTTGTTG TTTTTTTAGC AAGTTTAAAA TTGAACTTAA    50

SEQ ID NO: 390          moltype = AA   length = 50
FEATURE                 Location/Qualifiers
source                  1..50
                        mol_type = protein
                        organism = Mus musculus
SEQUENCE: 390
AACCAGCTAT CACCAAGCTC GTTAGGCTTT TCACCTCTAC CTAAAAATCT    50

SEQ ID NO: 391          moltype = AA   length = 50
FEATURE                 Location/Qualifiers
source                  1..50
                        mol_type = protein
                        organism = Mus musculus
SEQUENCE: 391
AATACTTGTA ATGCTAGAGG TGATGTTTTT GGTAAACAGG CGGGGTTCTT    50

SEQ ID NO: 392          moltype = AA   length = 50
FEATURE                 Location/Qualifiers
source                  1..50
                        mol_type = protein
                        organism = Mus musculus
SEQUENCE: 392
TTTATCTTTT TGGATCTTTC CTTTAGGCAT TCCGGTGTTG GGTTAACAGA    50

SEQ ID NO: 393          moltype = AA   length = 50
FEATURE                 Location/Qualifiers
source                  1..50

-continued

| | | |
|---|---|---|
| | mol_type = protein<br>organism = Mus musculus | |
| SEQUENCE: 393<br>TTATTTATAG TGTGATTATT GCCTATAGTC TGATTAACTA ACAATGGTTA | | 50 |
| SEQ ID NO: 394<br>FEATURE<br>source | moltype = AA length = 50<br>Location/Qualifiers<br>1..50<br>mol_type = protein<br>organism = Rattus norvegicus | |
| SEQUENCE: 394<br>AGTGATTGTA GTTGTTTATT CACTATTTAA GGTTTTTTCC TTTTCCTAAA | | 50 |
| SEQ ID NO: 395<br>FEATURE<br>source | moltype = AA length = 50<br>Location/Qualifiers<br>1..50<br>mol_type = protein<br>organism = Rattus norvegicus | |
| SEQUENCE: 395<br>TGGCTATATT TTAAGTTTAC ATTTTGATTT GTTGTTCTGA TGGTAAGCTT | | 50 |
| SEQ ID NO: 396<br>FEATURE<br>source | moltype = AA length = 50<br>Location/Qualifiers<br>1..50<br>mol_type = protein<br>organism = Rattus norvegicus | |
| SEQUENCE: 396<br>TTTTTTTAAT CTTTCCTTAA AGCACGCCTG TGTTGGGCTA ACGAGTTAGG | | 50 |
| SEQ ID NO: 397<br>FEATURE<br>source | moltype = AA length = 50<br>Location/Qualifiers<br>1..50<br>mol_type = protein<br>organism = Rattus norvegicus | |
| SEQUENCE: 397<br>TGTTGGGTTA GTACCTATGA TTCGATAATT GACAATGGTT ATCCGGGTTG | | 50 |
| SEQ ID NO: 398<br>FEATURE<br>source | moltype = AA length = 50<br>Location/Qualifiers<br>1..50<br>mol_type = protein<br>organism = Rattus norvegicus | |
| SEQUENCE: 398<br>AGGAGAATTG GTTCTTGTTA CTCATATTAA CAGTATTTCA TCTATGGATC | | 50 |
| SEQ ID NO: 399<br>FEATURE<br>source | moltype = AA length = 50<br>Location/Qualifiers<br>1..50<br>mol_type = protein<br>organism = Rattus norvegicus | |
| SEQUENCE: 399<br>TTTGTGATAT AGGAATTTAT TGAGGTTTGT GGAATTAGTG TGTGTAAGTA | | 50 |
| SEQ ID NO: 400<br>FEATURE<br>source | moltype = AA length = 50<br>Location/Qualifiers<br>1..50<br>mol_type = protein<br>organism = Mus musculus | |
| SEQUENCE: 400<br>GCCGGGGAGT GGGTCTTCCG TACGCCACAT TTCCCACGCC GCGACGCGCG | | 50 |
| SEQ ID NO: 401<br>FEATURE<br>source | moltype = AA length = 50<br>Location/Qualifiers<br>1..50<br>mol_type = protein<br>organism = Mus musculus | |
| SEQUENCE: 401<br>ACCTCGGGCC CCCGGGCGGG GCCCTTCACC TTCATTGCGC CACGGCGGCT | | 50 |
| SEQ ID NO: 402<br>FEATURE<br>source | moltype = AA length = 50<br>Location/Qualifiers<br>1..50<br>mol_type = protein<br>organism = Mus musculus | |
| SEQUENCE: 402<br>TCGCGTCCAG AGTCGCCGCC GCCGCCGGCC CCCCGAGTGT CCGGGCCCCC | | 50 |
| SEQ ID NO: 403<br>FEATURE | moltype = AA length = 50<br>Location/Qualifiers | |

```
source                  1..50
                        mol_type = protein
                        organism = Mus musculus
SEQUENCE: 403
CGCTGGTTCC TCCCGCTCCG GAACCCCCGC GGGGTTGGAC CCGCCGCCCC          50

SEQ ID NO: 404          moltype = AA  length = 50
FEATURE                 Location/Qualifiers
source                  1..50
                        mol_type = protein
                        organism = Mus musculus
SEQUENCE: 404
CGCCGACCCC CGACCCGCCC CCCGACGGGA AGAAGGAGGG GGGAAGAGAG          50

SEQ ID NO: 405          moltype = AA  length = 50
FEATURE                 Location/Qualifiers
source                  1..50
                        mol_type = protein
                        organism = Mus musculus
SEQUENCE: 405
GGGACGACGG GGCCCCGCGG GGAAGAGGGG AGGGCGGGCC CGGGCGGAAA          50

SEQ ID NO: 406          moltype = AA  length = 50
FEATURE                 Location/Qualifiers
source                  1..50
                        mol_type = protein
                        organism = Mus musculus
SEQUENCE: 406
GGCGCCGCGC GGAAAACCGC GGCCCGGGGG GCGGACCCGG CGGGGGAACA          50

SEQ ID NO: 407          moltype = AA  length = 50
FEATURE                 Location/Qualifiers
source                  1..50
                        mol_type = protein
                        organism = Mus musculus
SEQUENCE: 407
CCCCCACACG CGCGGGACAC GCCCGCCCGC CCCCGCCACG CACCTCGGGA          50

SEQ ID NO: 408          moltype = AA  length = 50
FEATURE                 Location/Qualifiers
source                  1..50
                        mol_type = protein
                        organism = Mus musculus
SEQUENCE: 408
CACCCGCTTT GGGCTGCATT CCCAAGCAAC CCGACTCCGG GAAGACCCGA          50

SEQ ID NO: 409          moltype = AA  length = 50
FEATURE                 Location/Qualifiers
source                  1..50
                        mol_type = protein
                        organism = Mus musculus
SEQUENCE: 409
TGGAGCGAGG CCCCGCGGGG AGGGGACCCG CGCCGGCACC CGCCGGGCTC          50

SEQ ID NO: 410          moltype = AA  length = 50
FEATURE                 Location/Qualifiers
source                  1..50
                        mol_type = protein
                        organism = Mus musculus
SEQUENCE: 410
CGAGGCCGGC GTGCCCCGAC CCCGACGCGA GGACGGGGCC GGGCGCCGGG          50

SEQ ID NO: 411          moltype = AA  length = 50
FEATURE                 Location/Qualifiers
source                  1..50
                        mol_type = protein
                        organism = Mus musculus
SEQUENCE: 411
TCCCCGGAGC GGGTCGCGCC CGCCCGCACG CGCGGGACGG ACGCTTGGCG          50

SEQ ID NO: 412          moltype = AA  length = 50
FEATURE                 Location/Qualifiers
source                  1..50
                        mol_type = protein
                        organism = Mus musculus
SEQUENCE: 412
TCCACACGAA CGTGCGTTCA ACGTGACGGG CGAGAGGGCG GCCCCCTTTC          50

SEQ ID NO: 413          moltype = AA  length = 50
```

| | | |
|---|---|---|
| FEATURE | Location/Qualifiers | |
| source | 1..50 | |
| | mol_type = protein | |
| | organism = Mus musculus | |aa
SEQUENCE: 413
TCCCAAGACG AACGGCTCTC CGCACCGGAC CCCGGTCCCG ACGCCCGGCG    50

SEQ ID NO: 414    moltype = AA   length = 50
FEATURE           Location/Qualifiers
source            1..50
                  mol_type = protein
                  organism = Mus musculus
SEQUENCE: 414
CCGCCGCGGG GACGACGCGG GGACCCCGCC GAGCGGGGAC GGACGGGGAC    50

SEQ ID NO: 415    moltype = AA   length = 50
FEATURE           Location/Qualifiers
source            1..50
                  mol_type = protein
                  organism = Mus musculus
SEQUENCE: 415
GCACCGCCAC GGTGGAAGTG CGCCCGGCGG CGGCCGGTCG CCGGCCGGGG    50

SEQ ID NO: 416    moltype = AA   length = 50
FEATURE           Location/Qualifiers
source            1..50
                  mol_type = protein
                  organism = Mus musculus
SEQUENCE: 416
CCCACCGGGC CCCGAGAGAG GCGACGGAGG GGGGTGGGAG AGCGGTCGCG    50

SEQ ID NO: 417    moltype = AA   length = 50
FEATURE           Location/Qualifiers
source            1..50
                  mol_type = protein
                  organism = Mus musculus
SEQUENCE: 417
CCCGGCCCCC ACCCCCACGC CCGCCCGGGA GGCGGACGGG GGGAGAGGGA    50

SEQ ID NO: 418    moltype = AA   length = 50
FEATURE           Location/Qualifiers
source            1..50
                  mol_type = protein
                  organism = Mus musculus
SEQUENCE: 418
TATCTGGCTT CCTCGGCCCC GGGATTCGGC GAAAGCGCGG CCGGAGGGCT    50

SEQ ID NO: 419    moltype = AA   length = 50
FEATURE           Location/Qualifiers
source            1..50
                  mol_type = protein
                  organism = Mus musculus
SEQUENCE: 419
CGCCGCCGAC CCCGTGCGCT CGGCTTCGTC GGGAGACGCG TGACCGACGG    50

SEQ ID NO: 420    moltype = AA   length = 50
FEATURE           Location/Qualifiers
source            1..50
                  mol_type = protein
                  organism = Mus musculus
SEQUENCE: 420
GCGCCCCCCC GCACCCGCCC CGTCCCCCCC GCGGACGGGG AAGAAGGGAG    50

SEQ ID NO: 421    moltype = AA   length = 50
FEATURE           Location/Qualifiers
source            1..50
                  mol_type = protein
                  organism = Mus musculus
SEQUENCE: 421
CGAACCCCGG GAACCCCCGA CCCCGCGGAG GGGGAAGGGG GAGGACGAGG    50

SEQ ID NO: 422    moltype = AA   length = 50
FEATURE           Location/Qualifiers
source            1..50
                  mol_type = protein
                  organism = Mus musculus
SEQUENCE: 422
CACCCGGGGG GGCGACGAGG CGGGGACCCG CCGGACGGGG ACGGACGGGG    50

```
SEQ ID NO: 423        moltype = AA  length = 50
FEATURE               Location/Qualifiers
source                1..50
                      mol_type = protein
                      organism = Mus musculus
SEQUENCE: 423
GCCAACCGAG GCTCCTTCGG CGCTGCCGTA TCGTTCCGCT TGGGCGGATT                 50

SEQ ID NO: 424        moltype = AA  length = 50
FEATURE               Location/Qualifiers
source                1..50
                      mol_type = protein
                      organism = Mus musculus
SEQUENCE: 424
CCCGGGCCCC CGGACCCCCG AGAGGGACGA CGGAGGCGAC GGGGGGTGGG                 50

SEQ ID NO: 425        moltype = AA  length = 50
FEATURE               Location/Qualifiers
source                1..50
                      mol_type = protein
                      organism = Mus musculus
SEQUENCE: 425
TGGGAGGGGC GGCCCGGCCC CCGCGACCGC CCCCCTTTCC GCCACCCCAC                 50

SEQ ID NO: 426        moltype = AA  length = 50
FEATURE               Location/Qualifiers
source                1..50
                      mol_type = protein
                      organism = Mus musculus
SEQUENCE: 426
GGGAGAGGCC GGGGGGAGAG CGCGGCGACG GGTATCCGGC TCCCTCGGCC                 50

SEQ ID NO: 427        moltype = AA  length = 50
FEATURE               Location/Qualifiers
source                1..50
                      mol_type = protein
                      organism = Mus musculus
SEQUENCE: 427
CGCTGCTGCC GGGGGGCTGT AACACTCGGG GCGGGGTGGT CCGGCGCCCA                 50

SEQ ID NO: 428        moltype = AA  length = 50
FEATURE               Location/Qualifiers
source                1..50
                      mol_type = protein
                      organism = Mus musculus
SEQUENCE: 428
CGCCGCCGAC CCCGTGCGCT CGGCTTCGCT CCCCCCCACC CCGAGAAGGG                 50
```

NUCLEASE-BASED RNA DEPLETION

CROSS-REFERENCE TO RELATED APPLICATIONS

This application is a continuation of U.S. patent application Ser. No. 16/721,468, filed Dec. 19, 2019, which claims the benefit of priority of U.S. Provisional Application Nos. 62/783,869, filed Dec. 21, 2018, and 62/847,797, filed May 14, 2019, each of which is incorporated by reference herein in its entirety for any purpose.

SEQUENCE LISTING

The present application is filed with a Sequence Listing in electronic format. The Sequence Listing is provided as a file entitled "2022-07-13_01243-0012-01US_Seq_List_ST26" created on Jul. 13, 2022, which is 534,121 bytes in size. The information in the electronic format of the sequence listing is incorporated herein by reference in its entirety.

BACKGROUND

Unwanted RNA in a nucleic acid sample, like a nucleic acid sample taken from human cells or tissues, can complicate the analysis of that sample, analysis such as gene expression analysis, microarray analysis and sequencing of a sample. As ribosomal RNA (rRNA) comprises roughly 95% of the RNA in a cell its presence is one example of an RNA species that can interfere and obfuscate results of a target nucleic acid in a sample, or those nucleic acids that a researcher or diagnostician might want to understand more about. For example, unwanted rRNA species can make it especially difficult to analyze RNA molecules of interest in a sample, such as tRNA or mRNA. This is an ever-present problem particularly for tissues that have been fixed, for example fixed by formalin and then embedded in wax such as formalin fixed paraffin embedded (FFPE) tissues from biopsies. Without removing the rRNA species from FFPE tissues they can interfere with the measurement and characterization of target RNA in the tissue thereby making it extremely difficult to derive medically actionable information from the target RNAs such as disease and cancer identification, potential treatment options and disease or cancer diagnosis and prognosis. While FFPE tissue is an example, the same issues with rRNA hold true for samples of all kinds such a blood, cells, and other types of nucleic acid containing samples.

Current commercially available methods for depleting undesired RNA from a nucleic sample include RiboZero® (Epicentre) and NEBNext® rRNA Depletion kits (NEB) and RNA depletion methods as described in U.S. Pat. Nos. 9,745,570 and 9,005,891. However, these methods, while being useful in depleting RNA, have their own disadvantages, including ease of use, high sample input requirements, technician hands on time, cost, and/or efficiency in depleting undesired RNA from a sample. What are needed are materials and methods that can more easily or cost effectively deplete unwanted RNA species from a sample thereby unlocking information in the target RNA which might have been hidden such as rare or difficult to identify sequence variants. Straightforward and reliable methods as described in this disclosure can greatly increase the availability of target RNA molecules for testing purposes, thereby discovering the information they hold about the sample and the organism from which it derives.

SUMMARY OF THE INVENTION

Nucleic acid samples such as those from eukaryotes or prokaryotes contain multitude nucleic acids, many of which are not of interest to a researcher. Researchers oftentimes wish to study a specific type of a nucleic acid, such as either DNA or RNA. When studying RNA, the sample of interest can contain many different types of RNA species that can overwhelm and hide the target RNA that is the focus of study. As such, RNA depletion refers to removing unwanted RNA and/or DNA species from a nucleic acid sample thereby leaving a nucleic acid sample enriched with the desired RNA for study.

The present disclosure provides a solution for depleting a nucleic acid sample of an overabundance of unwanted RNA species prior to further study. For example, an RNA sample of interest not only includes the target RNA to be studied, but also includes abundant transcripts like rRNA, globin mRNA, viral contaminates, or any other unwanted nucleic acids that can dominate the sample and swamp out the target of interest, thereby greatly decreasing a researcher's ability to accurately analyze the desired portion of the transcriptome.

Therefore, depleting unwanted RNA from a nucleic acid sample prior to analysis, such as expression microarrays or sequencing, increases the specificity and accuracy of analysis for the desired RNA targets. In the present disclosure, depletion of off-target RNA through degradation of specific DNA:RNA hybrids allows for efficient removal of unwanted RNA species from a sample prior to library preparation and analysis. Once a sample is depleted of unwanted RNA species, the remaining target RNA can be converted to cDNA. Obtaining actionable data as a result of a robust sample can lead to a better understanding and potential treatment options for cancer prognostics and diagnostics, a better understanding of our microbiome and its importance in our and other eukaryotic systems, a more thorough understanding of expression analysis of genes of interest, and the like.

In one embodiment, the present disclosure describes a method for depleting off-target RNA molecules from a nucleic acid sample comprising:

a) contacting a nucleic acid sample comprising at least one RNA or DNA target sequence and at least one off-target RNA molecule with a probe set comprising at least two DNA probes complementary to discontiguous sequences along the full length of the at least one off-target RNA molecule, thereby hybridizing the DNA probes to the off-target RNA molecules to form DNA: RNA hybrids, wherein each DNA:RNA hybrid is at least 5 bases apart, or at least 10 bases apart, along a given off-target RNA molecule sequence from any other DNA:RNA hybrid; and b) contacting the DNA:RNA hybrids with a ribonuclease that degrades the RNA from the DNA:RNA hybrids, thereby degrading the off-target RNA molecules in the nucleic acid sample to form a degraded mixture.

In one embodiment, the present disclosure relates to a composition comprising a probe set comprising at least two DNA probes complementary to discontiguous sequences along the full length of at least one off-target RNA molecule (e.g., at least 5 or at least 10 bases apart along the full length) in a nucleic acid sample. In some embodiments, the composition also comprises a ribonuclease capable of degrading RNA in a DNA:RNA hybrid. In another embodiment, the present disclosure relates to a composition comprising a probe set comprising at least two DNA probes hybridized to at least one off-target RNA molecule, wherein each DNA probe is hybridized at least 5, or at least 10, bases apart along the length of the off-target RNA molecule from any other DNA probe in the probe set.

In one embodiment, the present disclosure describes a kit comprising a probe set comprising at least two DNA probes complementary to discontiguous sequences along the full length of at least one off-target rRNA molecule (e.g., at least 5 bases apart or at least 10 bases apart along the full length) in a nucleic acid sample and a ribonuclease capable of degrading RNA in a DNA:RNA hybrid.

In one embodiment, the present disclosure describes a method of supplementing a probe set for use in depleting off-target RNA nucleic acid molecules from a nucleic acid sample comprising: a) contacting a nucleic acid sample comprising at least one RNA or DNA target sequence and at least one off-target RNA molecule from a first species with a probe set comprising at least two DNA probes complementary to discontiguous sequences along the full length of the at least one off-target RNA molecule from a second species, thereby hybridizing the DNA probes to the off-target RNA molecules to form DNA:RNA hybrids, wherein each DNA:RNA hybrid is at least 5 bases apart, or at least 10 bases apart, along a given off-target RNA molecule sequence from any other DNA:RNA hybrid; b) contacting the DNA:RNA hybrids with a ribonuclease that degrades the RNA from the DNA:RNA hybrids, thereby degrading the off-target RNA molecules in the nucleic acid sample to form a degraded mixture; c) separating the degraded rRNA from the degraded mixture; d) sequencing the remaining RNA from the sample; e) evaluating the remaining RNA sequences for the presence of off-target RNA molecules from the first species, thereby determining gap sequence regions; and f) supplementing the probe set with additional DNA probes complementary to discontiguous sequences in one or more of the gap sequence regions.

BRIEF DESCRIPTION OF THE FIGURES

FIG. 3 shows exemplary next-generation sequencing (NGS) sequence data for rRNA depleted samples of Human Brain RNA (HBR) and Universal Human RNA (UHR) comparing different amounts of sequenced sample (100 ng, 10 ng, or 1 ng).

FIG. 4 shows exemplary NGS sequence data for rRNA depleted samples from mouse RNA and rat RNA using different concentrations of formamide (0%, 25%, 45%) added to the rRNA depletion workflow.

DETAILED DESCRIPTION

Figure 1:
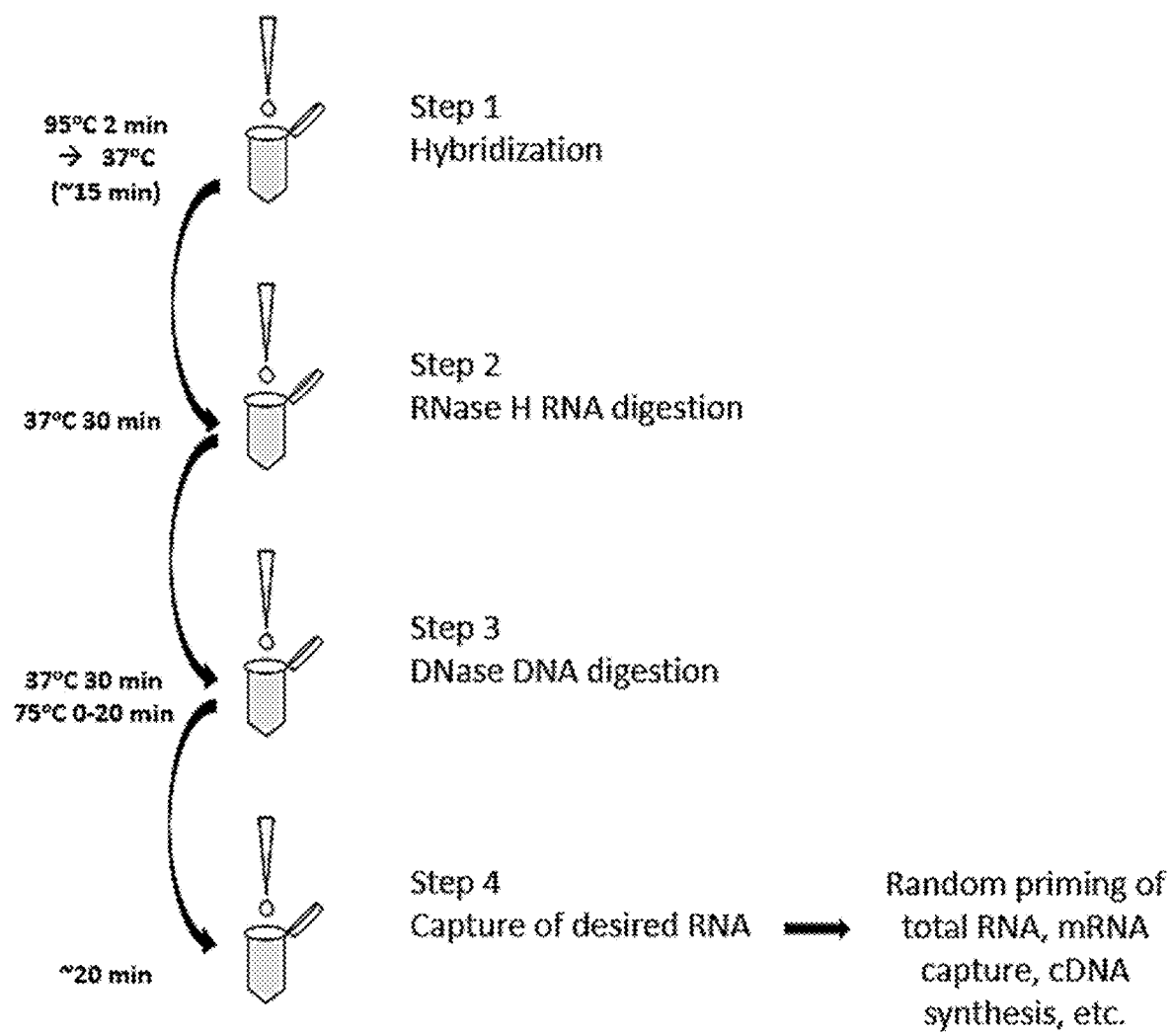
FIG. 1 shows an exemplary workflow for performing depletion of RNA species from a sample. Step 1 includes nucleic acid denaturation followed by addition of depletion DNA probes and hybridization of the probes with the unwanted RNA species, thereby creating DNA:RNA hybrids. Step 2 includes digestion of the RNA from the DNA:RNA hybrids using a ribonuclease such as RNase H. Step 3 includes digesting residual DNA probes from the degraded mixture by addition of DNase. Step 4 includes capturing the remaining target RNA in the sample, which is optionally followed by additional manipulations that will eventually result in a sample depleted of unwanted RNA species that can be sequenced, exposed to microarray expression analysis, qPCR, or other analysis techniques.

Creating nucleic acid libraries from RNA for sequencing is oftentimes difficult due to an abundance of unwanted transcripts such as ribosomal RNA, globin mRNA, viral contaminants, and the like that can dominate a sample and swamp out the RNA sequences of interest. If the unwanted transcripts are not removed, analysis of the transcriptome which would have prognostic, diagnostic or research benefit could be compromised. Therefore, depleting unwanted RNA from a nucleic acid sample prior to analysis such as sequencing or other downstream applications can increase the specificity and accuracy of the desired analysis.

The present disclosure describes methods and materials useful in depleting unwanted RNA species from a nucleic acid sample such that the RNA of importance can be studied and is not lost in the sea of undesired RNA transcripts.

Compared to existing methods for RNA depletion, the disclosed method can utilize smaller amounts of input total RNA while still maintaining comparable performance metrics. Therefore, the disclosed method can be used when a researcher has small amounts of starting material which other methods would not be able to accommodate. Further, the disclosed method can be performed with one pool of probes that target a variety of different organismal unwanted RNA species simultaneously without compromising depletion efficiency. For example, the present disclosure can simultaneously deplete unwanted eukaryotic and prokaryotic RNA species from an RNA sample, including but not limited to human, bacterial, viral and/or Archaea sources of unwanted RNA.

A nucleic acid sample or mixture refers to a sample that contains RNA or DNA or both, including both undesired (off-target or unwanted) and desired (target) nucleic acids. The DNA or RNA in the sample can be either unmodified or modified and includes, but is not limited to, single or double stranded DNA or RNA or derivatives thereof (e.g., some regions of the DNA or RNA are double stranded whereas concurrently other regions of the DNA or RNA are single stranded) and the like. In general, a nucleic acid sample includes all chemically, enzymatically, and/or metabolically modified forms of nucleic acids as well as all unmodified forms of nucleic acids, or combinations thereof. A nucleic acid sample can contain both wanted and unwanted nucleic acids such as genomic DNA or total cellular RNA or a combination of both. Unwanted nucleic acids include those nucleic acids from eukaryotes that are not targeted for study as well as contaminating nucleic acids from bacteria, viruses, Archaea species, and the like. Wanted or desired nucleic acids are those nucleic acids that are the basis or focus of study, the target nucleic acids. For example, a researcher may desire to study mRNA expression analysis, wherein rRNA, tRNA and DNA would be considered unwanted nucleic acids and mRNA is the target nucleic acid. As well, study of total RNA could be desired, whereas the rRNA, mRNA and DNA would be considered unwanted or undesired nucleic acids and the total RNA the target nucleic acid. Unwanted RNA includes, but is not limited to, ribosomal RNA (rRNA), mitochondrial rRNA, nuclear rRNA, mRNA such as globin RNAs, or transfer or tRNA, or a mixture thereof. In some embodiments, off-target RNA is rRNA. In some embodiments, off-target RNA is globin mRNA.

For example, a nucleic acid sample could contain the desired messenger RNA (mRNA) or total RNA while also including undesired ribosomal RNA (rRNA), transfer RNAs (tRNA) and perhaps undesired DNA. General methods for RNA extraction from a gross sample, like blood, tissue, cells, fixed tissues, etc., are well known in the art, as found in Current Protocols for Molecular Biology (John Wiley & Sons) and multitude molecular biology methods manuals. RNA isolation can be performed by commercially available purification kits, for example Qiagen RNeasy mini-columns, MasterPure Complete DNA and RNA Purification Kits (Epicentre), Parrafin Block RNA Isolation Kit (Ambion), RNA-Stat-60 (Tel-Test) or cesium chloride density gradient centrifugation. The current methods are not limited by how the RNA is isolated from a sample prior to RNA depletion.

There is an inherent skepticism that mixing probes targeting bacterial rRNA and human rRNA into the same pool would lead to extensive off-target depletion of desirable transcripts (Mauro et al., Proc. Natl. Acad. Sci. USA 1997, 94:422-427; Mignone and Pesole, Appl. Bioinformatics 2002, 1:145-54). Surprisingly, research performed while developing the disclosed methods demonstrates this isn't the case, as the specificity of the DNA probe hybridization with the unwanted RNA transcripts results in a sample efficiently depleted of unwanted RNA species. It was also discovered that the addition of a destabilizer such as formamide helps remove some unwanted RNA that was shown to be more problematic to deplete if formamide was not present. Although it is not necessary to understand the way in which formamide helps in removing those RNA, it is thought that the formamide may serve to relax structural barriers in the unwanted RNA so that the DNA probes can bind more efficiently. Further, the addition of formamide has demonstrated the added benefit of improving the detection of some non-targeted transcripts possibly by denaturing/relaxing regions of the mRNAs, for example, that have very stable secondary or tertiary structures and are not normally well represented well in other library preparation methods.

Nucleic Acid Samples or Mixtures

The present disclosure is not limited to the source of a nucleic acid sample, for example, the source could be from eukaryotes or prokaryotes including but not limited to humans, non-human primates, mammals, birds, reptiles, plants, bacteria, viruses, nucleic acids found in soils, water or other liquids and other environmental samples. The sample could be obtained from cells, tissues, organs, the environment, lysates, etc. and could come from any state of a sample such as fresh, frozen, lyophilized and reconstituted, or a fixed sample such as from a tissue or biopsy specimen that has been formalin fixed paraffin embedded (FFPE) or other cytological or histological sample manipulation.

The nucleic acid sample that could benefit from the RNA depletion methods could be from any species, eukaryotic or prokaryotic, such as humans, non-humans, mice, rats, bacteria, etc. and could include single or multiple species in one sample. Additionally, the present depletion methods could be used on fresh or preserved samples such as biopsy or tissue samples, including samples that have been processed using formalin and embedded in paraffin (e.g., formalin fixed paraffin embedded, FFPE, samples). In some embodiments, a nucleic acid sample is from a human or non-human source such as non-human eukaryotes, bacteria, viruses, plants, soil or a mixture thereof. Once a sample is depleted of unwanted RNA species, the remaining desired targets can be converted to cDNA for further processing as known to those skilled in the art.

In some embodiments, a nucleic acid sample is from a human or a non-human primate. In some embodiments, a nucleic acid sample is from a rat or a mouse. In some embodiments, a nucleic acid sample comprises nucleic acids of non-human origin. In some embodiments, nucleic acids of non-human origin are from non-human eukaryotes, bacteria, viruses, plants, soil, or a mixture thereof Depletion Methods As such, unwanted or undesired RNA in a nucleic acid sample is depleted by the described methods. The unwanted RNA is converted to a DNA:RNA hybrid by hybridizing partially or completely complementary DNA probes to the unwanted RNA molecules. Methods for hybridizing nucleic acid probes to nucleic acids are well established in the sciences and whether a probe is partially or completely complementary with the partner sequence, the fact that a DNA probe hybridizes to the unwanted RNA species following washes and other manipulations of the sample demonstrates a DNA probe that can be used in methods of the present disclosure. The unwanted RNA set for depletion can be from any eukaryotic species, for example, human, mice, rats, etc., where depletion of RNA from a sample might result in more favorable downstream studies such as sequencing (e.g., fewer results from unwanted nucleic acid species). DNA can also be considered an unwanted nucleic acid if the target for study is an RNA, at which point DNA can also be removed by depletion.

In one embodiment, the present disclosure describes a method for depleting off-target RNA molecules from a nucleic acid sample comprising:
 a) contacting a nucleic acid sample comprising at least one RNA or DNA target sequence and at least one off-target RNA molecule with a probe set comprising at least two DNA probes complementary to discontiguous sequences along the full length of the at least one off-target RNA molecule, thereby hybridizing the DNA probes to the off-target RNA molecules to form DNA:RNA hybrids, wherein each DNA:RNA hybrid is at least 5 bases apart, or at least 10 bases apart, along a given off-target RNA molecule sequence from any other DNA:RNA hybrid; and
 b) contacting the DNA:RNA hybrids with a ribonuclease that degrades the RNA from the DNA:RNA hybrids, thereby degrading the off-target RNA molecules in the nucleic acid sample to form a degraded mixture.

In one embodiment, an RNA sample is denatured in the presence of the DNA probes. An exemplary workflow is demonstrated in FIG. 1. In the example in FIG. 1, the DNA probes are added to the denatured RNA sample (denatured at 95° C. for 2 min.) whereupon cooling the reaction to 37° C. for 15-30 min results in hybridization of the DNA probes to their respective target RNA sequences thereby creating DNA:RNA hybrid molecules.

In some embodiments, contacting with the probe set comprises treating the nucleic acid sample with a destabilizer. In some embodiments, a destabilizer is heat or a nucleic acid destabilizing chemical. In some embodiments, a nucleic acid destabilizing chemical is betaine, DMSO, formamide, glycerol, or a derivative thereof, or a mixture thereof. In some embodiments, a nucleic acid destabilizing chemical is formamide or a derivative thereof, optionally wherein the formamide or derivative thereof is present at a concentration of from about 10 to 45% of the total hybridization reaction volume. In some embodiments, treating the sample with heat comprises applying heat above the melting temperature of the at least one DNA:RNA hybrid.

In some embodiments, formamide is added to the hybridization reaction regardless of RNA sample source (e.g., human, mouse, rat, etc.). For example, in some embodiments, hybridizing to the DNA probes is performed in the presence of at least 3%, 5%, 10%, 20%, 25%, 30%, 35%, 40%, or 45% by volume of formamide. In one embodiment, a hybridization reaction for RNA depletion includes approximately 25% to 45% by volume of formamide.

Following the hybridization reaction, a ribonuclease that degrades RNA from a DNA:RNA hybrid is added to the reaction. In some embodiments, a ribonuclease is RNase H or Hybridase. RNase H (NEB) or Hybridase (Lucigen) are examples of enzymes that will degrade RNA from a DNA:RNA hybrid. Degradation by a ribonuclease such as RNase H or Hybridase degrades the RNA into small molecules that can then be removed. For example, RNase H is reported to digest RNA from a DNA:RNA hybrid approximately every 7-21 bases (Schultz et al., J. Biol. Chem. 2006, 281:1943-1955; Champoux and Schultz, FEBS J. 2009, 276:1506-1516). In some embodiments, the digestion of the RNA of the DNA:RNA hybrid can occur at 37° C. for approximately 30 min as described in FIG. 1, Step 2, and Example 1.

In some embodiments, following DNA:RNA hybrid molecule digestion, the remaining DNA probes and any off-target DNA in the nucleic acid sample are degraded. Thus, in some embodiments, the methods comprise contacting the ribonuclease-degraded mixture with a DNA digesting enzyme, thereby degrading DNA in the mixture. In some embodiments, the digested sample is exposed to a DNA digesting enzyme such as DNase I, which degrades the DNA probes. The DNase DNA digestion reaction is incubated, for example, at 37° C. for 30 min, after which point the DNase enzyme can be denatured at 75° C. for a period of time as necessary to denature the DNase, for example for up to 20 min.

In some embodiments, the depletion method comprises separating the degraded RNA from the degraded mixture. In some embodiments, separating comprises purifying the target RNA from the degraded RNA (and degraded DNA if present), for example, using a nucleic acid purification medium, such as RNA capture beads, such as RNAClean XP beads (Beckman Coulter). Thus, in some embodiments, following the enzymatic digestion(s), the target RNA can be enriched by removing the degraded products while leaving the desired and longer RNA targets behind. Suitable enrichment methods include treating the degraded mixture with magnetic beads which bind to the desired fragment size of the enriched RNA targets, spin columns, and the like. In some embodiments, magnetic beads such as AMPure XP beads, SPRISelect beads, RNAClean XP beads (Beckman Coulter) can be used, as long as the beads are free of RNases (e.g., Quality Controlled to be RNase free). These beads provide different size selection options for nucleic acid binding, for example RNAClean XP beads target 100 nt or longer nucleic acid fragments and SPRISelect beads target 150 to 800 nt nucleic acid fragments and do not target shorter nucleic acid sequences such as the degraded RNA and DNA that results from the enzymatic digestions of RNase H and DNase. If mRNA is the target RNA to be studied, then the mRNA can be further enriched by capture using, for example, beads that comprise oligodT sequences for capturing the mRNA adenylated tails. Methods of mRNA capture are well known by skilled artisans.

Once the target RNA has been purified away from the reaction components including the undesired degraded nucleic acids, additional sample manipulation can occur. In the present disclosure, Examples 2 and 3 provide exemplary workflows for cDNA synthesis from the enriched target total RNA followed by an exemplary library preparation workflow that is typical for subsequent sequencing on, for example, an Illumina sequencer. However, it should be understood that these workflows are exemplary only and a skilled artisan will understand that the enriched RNA can be used in multitude additional applications such as PCR, qPCR, microarray analysis, and the like either directly or following additional manipulation such as converting the RNA to cDNA by using established and will understood protocols.

The methods described herein for RNA depletion will result in a sample enriched with the target RNA molecules. For example, the methods described herein result is a depleted RNA sample comprising less than 15%, 13%, 11%, 9%, 7%, 5%, 3%, 2% or 1% or any range in between of the unwanted RNA species. The enriched RNA sample then comprises at least 99%, 98%, 97%, 95%, 93%, 91%, 89% or 87% or any range in between of the target total RNA. Once the sample has been enriched it can be used for library preparation or other downstream manipulations.

DNA Probe Sets/DNA Probes

A DNA probe refers to a single stranded DNA oligonucleotide that has sequence complementarity to unwanted RNA species. The DNA probe sequence can be partly or completely complementary to the undesired RNA for depletion in the nucleic acid sample. The unwanted RNA for depletion includes, but is not limited to, rRNA, tRNA, and mRNA, and mixtures thereof. In some embodiments, each DNA probe is from about 10 and 100 nucleotides long, or from about 20 and 80 nucleotides long, or from about 40 to 60 nucleotides long, or about 50 nucleotides long. The DNA probes are capable of hybridizing to the unwanted RNA species, thereby creating DNA:RNA hybrid molecules. While in some embodiments, at least two DNA probes hybridize to a particular off-target RNA molecule, the DNA probes do not cover the entire length of an unwanted RNA molecule sequence. For example, in some embodiments, a probe set leaves gaps or regions of the unwanted RNA without a complementary DNA probe in the probe set. The DNA probes hybridize, completely or partly, to the unwanted RNA in a non-overlapping manner, leaving gaps of at least 5, 10, 15, 20, 30, 40, 50, 60, 70, 80 or more nucleotides between the resultant DNA:RNA hybrids. Thus, in some embodiments, each DNA probe is hybridized at least 5, or at least 10, bases apart along the full length of the at least one off-target RNA molecule from any other DNA probe in the probe set. As such, the unwanted RNA in its entirety is not completely hybridized to DNA probes. Further, the present disclosure provides for a plurality of DNA probes that hybridize to a single RNA for depletion as such there is not a "one DNA probe for one RNA", but instead multiple discontinuous DNA probes in a probe set that target a given unwanted RNA. For example, in some embodiments, for a given RNA set for depletion, a DNA probe set is used where each probe is approximately 20-80 nucleotides long and each probe hybridizes to the unwanted RNA anywhere from 5-15 nucleotides away from another DNA probe in the set. A DNA probe can be completely or partially complementary to a particular location on the RNA to be depleted, for example the DNA probe sequence can be at least 80%, 85%, 90%, 95%, or 100% complementary, or any range in between, to the target location on an RNA transcript to be depleted. The only limitation to complementarity is that the DNA probe should hybridize to the target RNA to be depleted in such a manner that a DNA:RNA hybrid results that is enzymatically digestible as described herein. In some cases, mRNA is the target of interest and not targeted for depletion, in which case the DNA probes do not comprise a polyT sequence so that the probes will not hybridize to mRNA species. In some embodiments, the DNA probes do not comprise a tag with a capture moiety such as biotin, avidin, streptavidin, or a magnetic bead that would allow for depletion of the hybrid by physical means, whereas in other embodiments the DNA probes do comprise a tag with a capture moiety such as biotin, avidin, streptavidin, or a magnetic bead that would allow for depletion of the hybrid by physical means.

In some embodiments, a probe set comprises at least DNA probes that hybridize to off-target RNA molecules from humans and bacteria. In some embodiments, a probe set comprises at least DNA probes that hybridize to off-target RNA molecules from humans, bacteria, and Archaea. In some embodiments, a probe set comprises at least DNA probes that hybridize to off-target RNA molecules from humans, bacteria, mouse, and rat. In some embodiments, a probe set comprises at least DNA probes that hybridize to off-target RNA molecules from humans, bacteria, mouse, rat, and Archaea. In some embodiments, the off-target RNA molecules from bacteria are from Gram-positive bacteria or Gram-negative bacteria, or a mixture thereof. In some embodiments, a probe set comprises at least two DNA probes that hybridize to one or more off-target RNA molecules from an Archaea species. In some embodiments, a probe set comprises at least two DNA probes complementary to two or more rRNA sequences from an Archaea species.

In some embodiments, a probe set comprises at least two DNA probes that hybridize to at least one, or at least two, off-target RNA molecules selected from 28S, 23S, 18S, 5.8S, 5S, 16S, 12S, HBA-A1, HBA-A2, HBB, HBB-B1, HBB-B2, HBG1, and HBG2. In some embodiments, the probe set comprises at least two DNA probes complementary to two or more rRNA sequences selected from the group consisting of 28S, 23S, 18S, 5.8S, 5S, 16S, 12S, HBA-A1, HBA-A2, HBB, HBB-B1, HBB-B2, HBG1, and HBG2. In some embodiments, a probe set comprises at least two DNA probes that hybridize to one or more, or two or more, off-target RNA molecules selected from 28S, 18S, 5.8S, 5S, 16S, and 12S from humans. In some embodiments, a probe set comprises at least two DNA probes that hybridize to one or more, or two or more, off-target RNA molecules from rat and/or mouse, optionally selected from rat 16S, rat 28S, mouse 16S, and mouse 28S, and combinations thereof. In some embodiments, a probe set comprises at least two DNA probes that hybridize to one or more off-target RNA molecules selected from HBA-A1, HBA-A2, HBB, HBB-B1, HBB-B2, HBG1, and HBG2 from hemoglobin. In some embodiments, a probe set comprises at least two DNA probes that hybridize to one or more off-target RNA molecules selected from 23S, 16S, and 5S from Gram positive and/or Gram negative bacteria. Globin mRNAs for depletion can include, but are not limited to, those found in rodents such as mouse or rat including HBA-A1, HBA-A2, HBB, HBB-B1, HBB-B2, and those found in humans including HBA-A1, HBA-A2, HBB, HGB1 and HGB2. Mitochondrial rRNAs suitable for depletion include 18S and 12S (humans and rodents). Nuclear rRNAs suitable for depletion include 28S, 18S, 5.8S and 5S (humans and rodents) and prokaryotic rRNAs including 5S, 16S and 23S. In some samples, the depletion of rRNAs from Archaea species may also be desired, such as rRNAs 23S, 16S or 5S. In further embodiments, the probe set comprises at least two DNA probes complementary to two or more rRNA sequences selected from the group consisting of Gram positive or Gram negative bacterial rRNA 5S, 16S and 23S. In some embodiments, the probe set comprises at least two (or at least five, or at least 10, or at least 20) DNA probes complementary to each of human 28S, 18S, 5.8S, 5S, 16S, and 12S, globin mRNA HBA-A1, HBA-A2, HBB, HBG1, and HBG2, and Gram positive or Gram negative bacterial rRNA 5S, 16S and 23S. In some embodiments, the probes to a particular off-target RNA molecule are complementary to about 80 to 85% of the sequence of the off-target RNA molecule, with gaps of at least 5, or at least 10 bases between each probe hybridization site.

In some embodiments, a probe set comprises two or more, or five or more, or 10 or more, or 25 or more, or 50 or more, or 100 or more, or 150 or more, or 200 or more, or 250 or more, or 300 or more, or 333 sequences from SEQ ID NOs: 1-333 (human, Gram-positive bacteria, and Gram-negative bacteria). In some embodiments, a probe set comprises two or more, or five or more, or 10 or more, or 25 or more, or 50 or more, or 100 or more, or 150 or more, or 200 or more, or 250 or more, or 300 or more, or 350 or more, or 400 or more, or 428 sequences from SEQ ID NOs: 1-428 (human, Gram-positive bacteria, Gram-negative bacteria, Archaea, mouse, and rat). In some embodiments, a probe set comprises two or more, or five or more, or 10 or more, or 25 or more, or 50 or more, or 100 or more, or 150 or more, or 200 or more, or 250 or more, or 300 or more, or 350 or more, or 377 sequences from SEQ ID NOs: 1-377 (human, Gram-positive bacteria, Gram-negative bacteria, and Archaea). In some embodiments, a probe set comprises two or more, or five or more, or 10 or more, or 25 or more, or 50 or more, or 100 or more, or 150 or more, or 200 or more, or 250 or more, or 300 or more, or 350 or more, or 384 sequences from SEQ ID NOs: 1-333 (human, Gram-positive bacteria, and Gram-negative bacteria) and SEQ ID NOs: 378-428 (mouse and rat). In some embodiments, a probe set comprises two or more, or five or more, or 10 or more, or 25 or more, or 44 sequences from SEQ ID NOs: 334-377 (Archaea). In some embodiments, a probe set comprises two or more, or five or more, or 10 or more, or 25 or more, or 50 or more, or 51 sequences from SEQ ID NOs: 378-428 (mouse and rat).

In some embodiments, the DNA probes are partially or completely complementary and comprise sequences that hybridize to human 28S, 18S, 5.8S and/or 5S rRNA, for example DNA probe sequences as shown in Table 1, SEQ ID NO: 40 through SEQ ID NO: 150. In a second embodiment, the DNA probes include sequences that hybridize to mitochondrial rRNAs 16S and/or 12S, for example DNA probe sequences as shown in Table 1, SEQ ID NO: 1 through SEQ ID NO: 39. In other embodiments, the DNA probes include sequences that hybridize to hemoglobin mRNA including HBA-A1, HBA-A2, HBB, HBB-B1, HBB-B2, HBG1, and/or HBG2, for example DNA probe sequences as shown in Table 1, SEQ ID NO: 151 through SEQ ID NO: 194. In some embodiments, the DNA probes include sequences that hybridize to bacterial rRNAs such as Gram positive and/or Gram negative bacterial rRNAs 23S, 16S and/or 5S, for example DNA probe sequences as shown in Table 1, SEQ ID NO: 195 through SEQ ID NO: 262 (Gram negative bacterial representative *E. coli*) and SEQ ID NO: 263 through SEQ ID NO: 333 (Gram positive bacterial representative *Bacillus subtilis*). In other embodiments, the DNA probes include sequences that hybridize to Archaea rRNAs, such as rRNAs 23S, 16S and/or 5S, for example the DNA probe sequences shown in Table 1, SEQ ID NO: 334 through SEQ ID NO: 384, which hybridize to rRNAs from Archaea species *Methanobrevibacter smithii*. In some embodiments, the DNA probes include sequences that hybridize to mouse rRNAs, such as mouse 16S and/or 28S, for example the DNA probe sequences shown in Table 1, SEQ ID NO: 385 through SEQ ID NO: 393 and SEQ ID NO:400 through SEQ ID NO: 419. In some embodiments, the DNA probes include sequences that hybridize to rat rRNAs, such as rat 16S and/or 28S, for example the DNA probe sequences shown in Table 1, SEQ ID NO: 394 through SEQ ID NO: 399 and SEQ ID NO: 420 through SEQ ID NO: 428.

TABLE 1

DNA probe sequences for unwanted RNA depletion

| SEQ ID NO | Probe name | Probe sequence 5'-3' |
|---|---|---|
| 1 | 12S_P1 | GTTCGTCCAAGTGCACTTTCCAGTACACTTACCATGTTACGACTTGTCTC |
| 2 | 12S_P2 | TAGGGGTTTTAGTTAAATGTCCTTTGAAGTATACTTGAGGAGGGTGACGG |
| 3 | 12S_P3 | TTCAGGGCCCTGTTCAACTAAGCACTCTACTCTCAGTTTACTGCTAAATC |
| 4 | 12S_P4 | AGTTTCATAAGGGCTATCGTAGTTTTCTGGGGTAGAAAATGTAGCCCATT |
| 5 | 12S_P5 | GGCTACACCTTGACCTAACGTCTTTACGTGGGTACTTGCGCTTACTTTGT |
| 6 | 12S_P6 | TTGCTGAAGATGGCGGTATATAGGCTGAGCAAGAGGTGGTGAGGTTGATC |
| 7 | 12S_P7 | CAGAACAGGCTCCTCTAGAGGGATATGAAGCACCGCCAGGTCCTTTGAGT |
| 8 | 12S_P8 | GTAGTGTTCTGGCGAGCAGTTTTGTTGATTTAACTGTTGAGGTTTAGGGC |
| 9 | 12S_P9 | ATCTAATCCCAGTTTGGGTCTTAGCTATTGTGTGTTCAGATATGTTAAAG |
| 10 | 12S_P10 | ATTTTGTGTCAACTGGAGTTTTTTACAACTCAGGTGAGTTTTAGCTTTAT |
| 11 | 12S_P11 | CTAAAACACTCTTTACGCCGGCTTCTATTGACTTGGGTTAATCGTGTGAC |
| 12 | 12S_P12 | GAAATTGACCAACCCTGGGGTTAGTATAGCTTAGTTAAACTTTCGTTTAT |
| 13 | 12S_P13 | ACTGCTGTTTCCCGTGGGGGTGTGGCTAGGCTAAGCGTTTTGAGCTGCAT |
| 14 | 12S_P14 | GCTTGTCCCTTTTGATCGTGGTGATTTAGAGGGTGAACTCACTGGAACGG |
| 15 | 12S_P15 | TAATCTTACTAAGAGCTAATAGAAAGGCTAGGACCAAACCTATTTGTTTA |
| 16 | 16S_P1 | AAACCCTGTTCTTGGGTGGGTGTGGGTATAATACTAAGTTGAGATGATAT |
| 17 | 16S_P2 | GCGCTTTGTGAAGTAGGCCTTATTTCTCTTGTCCTTTCGTACAGGGAGGA |
| 18 | 16S_P3 | AAACCGACCTGGATTACTCCGGTCTGAACTCAGATCACGTAGGACTTTAA |
| 19 | 16S_P4 | ACCTTTAATAGCGGCTGCACCATCGGGATGTCCTGATCCAACATCGAGGT |
| 20 | 16S_P5 | TGATATGGACTCTAGAATAGGATTGCGCTGTTATCCCTAGGGTAACTTGT |
| 21 | 16S_P6 | ATTGGATCAATTGAGTATAGTAGTTCGCTTTGACTGGTGAAGTCTTAGCA |
| 22 | 16S_P7 | TTGGGTTCTGCTCCGAGGTCGCCCCAACCGAAATTTTTAATGCAGGTTTG |

TABLE 1-continued

DNA probe sequences for unwanted RNA depletion

| SEQ ID NO | Probe name | Probe sequence 5'-3' |
|---|---|---|
| 23 | 16S_P8 | TGGGTTTGTTAGGTACTGTTTGCATTAATAAATTAAAGCTCCATAGGGTC |
| 24 | 16S_P9 | GTCATGCCCGCCTCTTCACGGGCAGGTCAATTTCACTGGTTAAAAGTAAG |
| 25 | 16S_P10 | CGTGGAGCCATTCATACAGGTCCCTATTTAAGGAACAAGTGATTATGCTA |
| 26 | 16S_P11 | GGTACCGCGGCCGTTAAACATGTGTCACTGGGCAGGCGGTGCCTCTAATA |
| 27 | 16S_P12 | GTGATGTTTTTGGTAAACAGGCGGGGTAAGGTTTGCCGAGTTCCTTTTAC |
| 28 | 16S_P13 | CTTATGAGCATGCCTGTGTTGGGTTGACAGTGAGGGTAATAATGACTTGT |
| 29 | 16S_P14 | ATTGGGCTGTTAATTGTCAGTTCAGTGTTTTGATCTGACGCAGGCTTATG |
| 30 | 16S_P15 | TCATGTTACTTATACTAACATTAGTTCTTCTATAGGGTGATAGATTGGTC |
| 31 | 16S_P16 | AGTTCAGTTATATGTTTGGGATTTTTTAGGTAGTGGGTGTTGAGCTTGAA |
| 32 | 16S_P17 | TGGCTGCTTTTAGGCCTACTATGGGTGTTAAATTTTTACTCTCTACA |
| 33 | 16S_P18 | GTCCAAAGAGCTGTTCCTCTTTGGACTAACAGTTAAATTTACAAGGGGAT |
| 34 | 16S_P19 | GGCAAATTTAAAGTTGAACTAAGATTCTATCTTGGACAACCAGCTATCAC |
| 35 | 16S_P20 | TGTCGCCTCTACCTATAAATCTTCCCACTATTTTGCTACATAGACGGGTG |
| 36 | 16S_P21 | TCTTAGGTAGCTCGTCTGGTTTCGGGGGTCTTAGCTTTGGCTCTCCTTGC |
| 37 | 16S_P22 | TAATTCATTATGCAGAAGGTATAGGGGTTAGTCCTTGCTATATTATGCTT |
| 38 | 16S_P23 | TCTTTCCCTTGCGGTACTATATCTATTGCGCCAGGTTTCAATTTCTATCG |
| 39 | 16S_P24 | GGTAAATGGTTTGGCTAAGGTTGTCTGGTAGTAAGGTGGAGTGGGTTTGG |
| 40 | 18S_P1 | TAATGATCCTTCCGCAGGTTCACCTACGGAAACCTTGTTACGACTTTTAC |
| 41 | 18S_P2 | AAGTTCGACCGTCTTCTCAGCGCTCCGCCAGGGCCGTGGGCCGACCCCGG |
| 42 | 18S_P3 | GGCCTCACTAAACCATCCAATCGGTAGTAGCGACGGGCGGTGTGTACAAA |
| 43 | 18S_P4 | CAACGCAAGCTTATGACCCGCACTTACTCGGGAATTCCCTCGTTCATGGG |
| 44 | 18S_P5 | CCGATCCCCATCACGAATGGGGTTCAACGGGTTACCCGCGCCTGCCGGCG |
| 45 | 18S_P6 | CTGAGCCAGTCAGTGTAGCGCGCGTGCAGCCCCGGACATCTAAGGGCATC |
| 46 | 18S_P7 | CTCAATCTCGGGTGGCTGAACGCCACTTGTCCCTCTAAGAAGTTGGGGGA |
| 47 | 18S_P8 | GGTCGCGTAACTAGTTAGCATGCCAGAGTCTCGTTCGTTATCGGAATTAA |
| 48 | 18S_P9 | CACCAACTAAGAACGGCCATGCACCACCACCCACGGAATCGAGAAAGAGC |
| 49 | 18S_P10 | CCTGTCCGTGTCCGGGCCGGGTGAGGTTTCCCGTGTTGAGTCAAATTAAG |
| 50 | 18S_P11 | CTGGTGGTGCCCTTCCGTCAATTCCTTTAAGTTTCAGCTTTGCAACCATA |
| 51 | 18S_P12 | AAAGACTTTGGTTTCCCGGAAGCTGCCCGGCGGGTCATGGGAATAACGCC |
| 52 | 18S_P13 | GGCATCGTTTATGGTCGGAACTACGACGGTATCTGATCGTCTTCGAACCT |
| 53 | 18S_P14 | GATTAATGAAAACATTCTTGGCAAATGCTTTCGCTCTGGTCCGTCTTGCG |
| 54 | 18S_P15 | CACCTCTAGCGGCGCAATACGAATGCCCCCGGCCGTCCCTCTTAATCATG |
| 55 | 18S_P16 | ACCAACAAAATAGAACCGCGGTCCTATTCCATTATTCCTAGCTGCGGTAT |
| 56 | 18S_P17 | CTGCTTTGAACACTCTAATTTTTTCAAAGTAAACGCTTCGGGCCCCGCGG |
| 57 | 18S_P18 | GCATCGAGGGGCGCCGAGAGGCAAGGGGCGGGGACGGGCGGTGGCTCGC |
| 58 | 18S_P19 | CCGCCCGCTCCCAAGATCCAACTACGAGCTTTTTAACTGCAGCAACTTTA |
| 59 | 18S_P20 | GCTGGAATTACCGCGGCTGCTGGCACCAGACTTGCCCTCCAATGGATCCT |

TABLE 1-continued

DNA probe sequences for unwanted RNA depletion

| SEQ ID NO | Probe name | Probe sequence 5'-3' |
|---|---|---|
| 60 | 18S_P21 | AGTGGACTCATTCCAATTACAGGGCCTCGAAAGAGTCCTGTATTGTTATT |
| 61 | 18S_P22 | CCCGGGTCGGGAGTGGGTAATTTGCGCGCCTGCTGCCTTCCTTGGATGTG |
| 62 | 18S_P23 | GCTCCCTCTCCGGAATCGAACCCTGATTCCCCGTCACCCGTGGTCACCAT |
| 63 | 18S_P24 | TACCATCGAAAGTTGATAGGGCAGACGTTCGAATGGGTCGTCGCCGCCAC |
| 64 | 18S_P25 | GGCCCGAGGTTATCTAGAGTCACCAAAGCCGCCGGCGCCCGCCCCCCGGC |
| 65 | 18S_P26 | GCTGACCGGGTTGGTTTTGATCTGATAAATGCACGCATCCCCCCCGCGAA |
| 66 | 18S_P27 | TCGGCATGTATTAGCTCTAGAATTACCACAGTTATCCAAGTAGGAGAGGA |
| 67 | 18S_P28 | AACCATAACTGATTTAATGAGCCATTCGCAGTTTCACTGTACCGGCCGTG |
| 68 | 18S_P29 | ATGGCTTAATCTTTGAGACAAGCATATGCTACTGGCAGGATCAACCAGGT |
| 69 | 28S_P1 | GACAAACCCTTGTGTCGAGGGCTGACTTTCAATAGATCGCAGCGAGGGAG |
| 70 | 28S_P2 | CGAAACCCCGACCCAGAAGCAGGTCGTCTACGAATGGTTTAGCGCCAGGT |
| 71 | 28S_P3 | GGTGCGTGACGGGCGAGGGGGCGGCCGCCTTTCCGGCCGCGCCCCGTTTC |
| 72 | 28S_P4 | CTCCGCACCGGACCCCGGTCCCGGCGCGCGGCGGGGCACGCGCCCTCCCG |
| 73 | 28S_P5 | AGGGGGGGGCGGCCCGCCGGCGGGGACAGGCGGGGGACCGGCTATCCGAG |
| 74 | 28S_P6 | GCGGCGCTGCCGTATCGTTCGCCTGGGCGGGATTCTGACTTAGAGGCGTT |
| 75 | 28S_P7 | AGATGGTAGCTTCGCCCCATTGGCTCCTCAGCCAAGCACATACACCAAAT |
| 76 | 28S_P8 | TCCTCTCGTACTGAGCAGGATTACCATGGCAACAACACATCATCAGTAGG |
| 77 | 28S_P9 | CTCACGACGGTCTAAACCCAGCTCACGTTCCCTATTAGTGGGTGAACAAT |
| 78 | 28S_P10 | TTCTGCTTCACAATGATAGGAAGAGCCGACATCGAAGGATCAAAAAGCGA |
| 79 | 28S_P11 | TTGGCCGCCACAAGCCAGTTATCCCTGTGGTAACTTTTCTGACACCTCCT |
| 80 | 28S_P12 | GGTCAGAAGGATCGTGAGGCCCCGCTTTCACGGTCTGTATTCGTACTGAA |
| 81 | 28S_P13 | AGCTTTTGCCCTTCTGCTCCACGGGAGGTTTCTGTCCTCCCTGAGCTCGC |
| 82 | 28S_P14 | TTACCGTTTGACAGGTGTACCGCCCCAGTCAAACTCCCCACCTGGCACTG |
| 83 | 28S_P15 | GCGCCCGGCCGGGCGGGCGCTTGGCGCCAGAAGCGAGAGCCCCTCGGGCT |
| 84 | 28S_P16 | CCGGGTCAGTGAAAAAACGATCAGAGTAGTGGTATTTCACCGGCGGCCCG |
| 85 | 28S_P17 | CGCCCCGGGCCCCTCGCGGGGACACCGGGGGGCGCCGGGGCCTCCCAC |
| 86 | 28S_P18 | CATGTCTCTTCACCGTGCCAGACTAGAGTCAAGCTCAACAGGGTCTTCTT |
| 87 | 28S_P19 | CCAAGCCCGTTCCCTTGGCTGTGGTTTCGCTGGATAGTAGGTAGGGACAG |
| 88 | 28S_P20 | TCCATTCATGCGCGTCACTAATTAGATGACGAGGCATTTGGCTACCTTAA |
| 89 | 28S_P21 | TCCCGCCGTTTACCCGCGCTTCATTGAATTTCTTCACTTTGACATTCAGA |
| 90 | 28S_P22 | CACATCGCGTCAACACCCGCCGCGGGCCTTCGCGATGCTTTGTTTTAATT |
| 91 | 28S_P23 | CCTGGTCCGACACCAGTTCTAAGTCGGCTGCTAGGCGCCGGCCGAGGCGAG |
| 92 | 28S_P24 | CGGCCCCGGGGCGGACCCGGCGGGGGGACCGGCCCGCGGCCCCTCCGC |
| 93 | 28S_P25 | CCGCCGCGCGCCGAGGAGGAGGGGGGAACGGGGGGCGGACGGGGCCGGGG |
| 94 | 28S_P26 | ACGAACCGCCCCGCCCCGCCGCCCGCCGACCGCCGCCGCCCGACCGCTCC |
| 95 | 28S_P27 | CGCGCGCGACCGAGACGTGGGGTGGGGTGGGGGCGCGCCGCGCCGCCG |
| 96 | 28S_P28 | GCGGCCGCGACGCCCGCCGCAGCTGGGGCGATCCACGGGAAGGGCCCGGC |
| 97 | 28S_P29 | GCGCCGCCGCCGGCCCCCCGGGTCCCCGGGGCCCCCCTCGCGGGGACCTG |

TABLE 1-continued

DNA probe sequences for unwanted RNA depletion

| SEQ ID NO | Probe name | Probe sequence 5'-3' |
|---|---|---|
| 98 | 28S_P30 | CCGGCGGCCGCCGCGCGGCCCCTGCCGCCCCGACCCTTCTCCCCCCGCCG |
| 99 | 28S_P31 | CTCCCCCGGGGAGGGGGAGGACGGGGAGCGGGGGAGAGAGAGAGAGAGA |
| 100 | 28S_P32 | AGGGAGCGAGCGGCGCGCGCGGGTGGGGCGGGGAGGGCCGCGAGGGGGG |
| 101 | 28S_P33 | GGGGGCGCGCGCCTCGTCCAGCCGCGGCGCGCGCCCAGCCCCGCTTCGCG |
| 102 | 28S_P34 | CCCAGCCCTTAGAGCCAATCCTTATCCCGAAGTTACGGATCCGGCTTGCC |
| 103 | 28S_P35 | CATTGTTCCAACATGCCAGAGGCTGTTCACCTTGGAGACCTGCTGCGGAT |
| 104 | 28S_P36 | CGCGAGATTTACACCCTCTCCCCCGGATTTTCAAGGGCCAGCGAGAGCTC |
| 105 | 28S_P37 | AACCGCGACGCTTTCCAAGGCACGGGCCCCTCTCTCGGGGCGAACCCATT |
| 106 | 28S_P38 | CTTCACAAAGAAAAGAGAACTCTCCCCGGGGCTCCCGCCGGCTTCTCCGG |
| 107 | 28S_P39 | CGCACTGGACGCCTCGCGGCGCCCATCTCCGCCACTCCGGATTCGGGGAT |
| 108 | 28S_P40 | TTTCGATCGGCCGAGGGCAACGGAGGCCATCGCCCGTCCCTTCGGAACGG |
| 109 | 28S_P41 | CAGGACCGACTGACCCATGTTCAACTGCTGTTCACATGGAACCCTTCTCC |
| 110 | 28S_P42 | GTTCTCGTTTGAATATTTGCTACTACCACCAAGATCTGCACCTGCGGCGG |
| 111 | 28S_P43 | CGCCCTAGGCTTCAAGGCTCACCGCAGCGGCCCTCCTACTCGTCGCGGCG |
| 112 | 28S_P44 | TCCGGGGCGGGGAGCGGGGCGTGGGCGGGAGGAGGGGAGGAGGCGTGGG |
| 113 | 28S_P45 | AGGACCCCACACCCCCGCCGCCGCCGCCGCCGCCGCCCTCCGACGCACAC |
| 114 | 28S_P46 | GCGCGCCGCCCCCGCCGCTCCCGTCCACTCTCGACTGCCGGCGACGGCCG |
| 115 | 28S_P47 | CTCCAGCGCCATCCATTTTCAGGGCTAGTTGATTCGGCAGGTGAGTTGTT |
| 116 | 28S_P48 | GATTCCGACTTCCATGGCCACCGTCCTGCTGTCTATATCAACCAACACCT |
| 117 | 28S_P49 | GAGCGTCGGCATCGGGCGCCTTAACCCGGCGTTCGGTTCATCCCGCAGCG |
| 118 | 28S_P50 | AAAAGTGGCCCACTAGGCACTCGCATTCCACGCCCGGCTCCACGCCAGCG |
| 119 | 28S_P51 | CCATTTAAAGTTTGAGAATAGGTTGAGATCGTTTCGGCCCCAAGACCTCT |
| 120 | 28S_P52 | CGGATAAAACTGCGTGGCGGGGTGCGTCGGGTCTGCGAGAGCGCCAGCT |
| 121 | 28S_P53 | TCGGAGGGAACCAGCTACTAGATGGTTCGATTAGTCTTTCGCCCCTATAC |
| 122 | 28S_P54 | GATTTGCACGTCAGGACCGCTACGGACCTCCACCAGAGTTTCCTCTGGCT |
| 123 | 28S_P55 | ATAGTTCACCATCTTTCGGGTCCTAACACGTGCGCTCGTGCTCCACCTCC |
| 124 | 28S_P56 | AGACGGGCCGGTGGTGCGCCCTCGGCGGACTGGAGAGGCCTCGGGATCCC |
| 125 | 28S_P57 | CGCGCCGGCCTTCACCTTCATTGCGCCACGGCGGCTTTCGTGCGAGCCCC |
| 126 | 28S_P58 | TTAGACTCCTTGGTCCGTGTTTCAAGACGGGTCGGGTGGGTAGCCGACGT |
| 127 | 28S_P59 | GCGCTCGCTCCGCCGTCCCCCTCTTCGGGGGACGCGCGCGTGGCCCCGAG |
| 128 | 28S_P60 | CCCGACGGCGCGACCCGCCCGGGGCGCACTGGGGACAGTCCGCCCCGCCC |
| 129 | 28S_P61 | GCACCCCCCCGTCGCCGGGGCGGGGCGCGGGAGGAGGGGTGGGAGAG |
| 130 | 28S_P62 | AGGGGTGGCCCGGCCCCCCACGAGGAGACGCCGGCGCGCCCCGCGGGG |
| 131 | 28S_P63 | GGGGATTCCCCGCGGGGTGGGCGCCGGGAGGGGGAGAGCGCGGCGACG |
| 132 | 28S_P64 | GCCCCGGGATTCGGCGAGTGCTGCTGCCGGGGGGCTGTAACACTCGGGG |
| 133 | 28S_P65 | CCGCCCCGCCGCCGCCGCCACCGCCGCCGCCGCCGCCGCCCCGACCCGC |
| 134 | 28S_P66 | AGGACGCGGGGCCGGGGGGCGGAGACGGGGAGGAGGAGGACGGACGGAC |

TABLE 1-continued

DNA probe sequences for unwanted RNA depletion

| SEQ ID NO | Probe name | Probe sequence 5'-3' |
|---|---|---|
| 135 | 28S_P67 | AGCCACCTTCCCCGCCGGGCCTTCCCAGCCGTCCCGGAGCCGGTCGCGGC |
| 136 | 28S_P68 | AAATGCGCCCGGCGGCGGCCGGTCGCCGGTCGGGGACGGTCCCCCGCCG |
| 137 | 28S_P69 | CCGCCCGCCCACCCCCGCACCCGCCGGAGCCCGCCCCCTCCGGGGAGGAG |
| 138 | 28S_P70 | GGGAAGGGAGGGCGGGTGGAGGGGTCGGGAGGAACGGGGGGCGGGAAAGA |
| 139 | 28S_P71 | ACACGGCCGGACCCGCCGCCGGGTTGAATCCTCCGGGCGGACTGCGCGGA |
| 140 | 28S_P72 | TCTTAACGGTTTCACGCCCTCTTGAACTCTCTCTTCAAAGTTCTTTTCAA |
| 141 | 28S_P73 | CTTGTTGACTATCGGTCTCGTGCCGGTATTTAGCCTTAGATGGAGTTTAC |
| 142 | 28S_P74 | GCATTCCCAAGCAACCCGACTCCGGGAAGACCCGGGCGCGCGCCGGCCGC |
| 143 | 28S_P75 | GTCCACGGGCTGGGCCTCGATCAGAAGGACTTGGGCCCCCCACGAGCGGC |
| 144 | 28S_P76 | TTCCGTACGCCACATGTCCCGCGCCCCGCGGGGCGGGGATTCGGCGCTGG |
| 145 | 28S_P77 | CTCGCCGTTACTGAGGGAATCCTGGTTAGTTTCTTTTCCTCCGCTGACTA |
| 146 | 28S_P78 | GCGGGTCGCCACGTCTGATCTGAGGTCGCGTCTCGGAGGGGGACGGGCCG |
| 147 | 5.8S_P1 | AAGCGACGCTCAGACAGGCGTAGCCCCGGGAGGAACCCGGGGCCGCAAGT |
| 148 | 5.8S_P3 | GCAGCTAGCTGCGTTCTTCATCGACGCACGAGCCGAGTGATCCACCGCTA |
| 149 | 5S_P1 | AAAGCCTACAGCACCCGGTATTCCCAGGCGGTCTCCCATCCAAGTACTAA |
| 150 | 5S_P3 | TTCCGAGATCAGACGAGATCGGGCGCGTTCAGGGTGGTATGGCCGTAGAC |
| 151 | HBA1_P1 | GCCGCCCACTCAGACTTTATTCAAAGACCACGGGGGTACGGGTGCAGGAA |
| 152 | HBA1_P2 | GGGGGAGGCCCAAGGGGCAAGAAGCATGGCCACCGAGGCTCCAGCTTAAC |
| 153 | HBA1_P3 | GCACGGTGCTCACAGAAGCCAGGAACTTGTCCAGGGAGGCGTGCACCGCA |
| 154 | HBA1_P4 | GGGAGGTGGGCGGCCAGGGTCACCAGCAGGCAGTGGCTTAGGAGCTTGAA |
| 155 | HBA1_P5 | CCGAAGCTTGTGCGCGTGCAGGTCGCTCAGGGCGGACAGCGCGTTGGGCA |
| 156 | HBA1_P6 | CCACGGCGTTGGTCAGCGCGTCGGCCACCTTCTTGCCGTGGCCCTTAACC |
| 157 | HBA1_P7 | CTCAGGTCGAAGTGCGGGAAGTAGGTCTTGGTGGTGGGGAAGGACAGGAA |
| 158 | HBA1_P8 | CTCCGCACCATACTCGCCAGCGTGCGCGCCGACCTTACCCCAGGCGGCCT |
| 159 | HBA1_P9 | CGGCAGGAGACAGCACCATGGTGGGTTCTCTCTGAGTCTGTGGGGACCAG |
| 160 | HBA2_P1 | GAGGGGAGGAGGGCCCGTTGGGAGGCCCAGCGGGCAGGAGGAACGGCTAC |
| 161 | HBA2_P2 | ACGGTATTTGGAGGTCAGCACGGTGCTCACAGAAGCCAGGAACTTGTCCA |
| 162 | HBA2_P3 | CAGGGGTGAACTCGGCGGGGAGGTGGGCGGCCAGGGTCACCAGCAGGCAG |
| 163 | HBA2_P4 | AAGTTGACCGGGTCCACCCGAAGCTTGTGCGCGTGCAGGTCGCTCAGGGC |
| 164 | HBA2_P5 | CATGTCGTCCACGTGCGCCACGGCGTTGGTCAGCGCGTCGGCCACCTTCT |
| 165 | HBA2_P6 | CCTGGGCAGAGCCGTGGCTCAGGTCGAAGTGCGGGAAGTAGGTCTTGGTG |
| 166 | HBA2_P7 | AACATCCTCTCCAGGGCCTCCGCACCATACTCGCCAGCGTGCGCGCCGAC |
| 167 | HBA2_P8 | CTTGACGTTGGTCTTGTCGGCAGGAGACAGCACCATGGTGGGTTCTCTCT |
| 168 | HBB_P1 | GCAATGAAAATAAATGTTTTTTATTAGGCAGAATCCAGATGCTCAAGGCC |
| 169 | HBB_P2 | CAGTTTAGTAGTTGGACTTAGGGAACAAAGGAACCTTTAATAGAAATTGG |
| 170 | HBB_P3 | GCTTAGTGATACTTGTGGGCCAGGGCATTAGCCACACCAGCCACCACTTT |
| 171 | HBB_P4 | CACTGGTGGGGTGAATTCTTTGCCAAAGTGATGGGCCAGCACACAGACCA |
| 172 | HBB_P5 | GCCTGAAGTTCTCAGGATCCACGTGCAGCTTGTCACAGTGCAGCTCACTC |

TABLE 1-continued

DNA probe sequences for unwanted RNA depletion

| SEQ ID NO | Probe name | Probe sequence 5'-3' |
|---|---|---|
| 173 | HBB_P6 | CCCTTGAGGTTGTCCAGGTGAGCCAGGCCATCACTAAAGGCACCGAGCAC |
| 174 | HBB_P7 | CTTCACCTTAGGGTTGCCCATAACAGCATCAGGAGTGGACAGATCCCCAA |
| 175 | HBB_P8 | TCTGGGTCCAAGGGTAGACCACCAGCAGCCTGCCCAGGGCCTCACCACCA |
| 176 | HBB_P9 | ACCTTGCCCCACAGGGCAGTAACGGCAGACTTCTCCTCAGGAGTCAGATG |
| 177 | HBG1_P1 | GTGATCTCTCAGCAGAATAGATTTATTATTTGTATTGCTTGCAGAATAAA |
| 178 | HBG1_P2 | CTCTGAATCATGGGCAGTGAGCTCAGTGGTATCTGGAGGACAGGGCACTG |
| 179 | HBG1_P3 | ATCTTCTGCCAGGAAGCCTGCACCTCAGGGGTGAATTCTTTGCCGAAATG |
| 180 | HBG1_P4 | CACCAGCACATTTCCCAGGAGCTTGAAGTTCTCAGGATCCACATGCAGCT |
| 181 | HBG1_P5 | CACTCAGCTGGGCAAAGGTGCCCTTGAGATCATCCAGGTGCTTTGTGGCA |
| 182 | HBG1_P6 | AGCACCTTCTTGCCATGTGCCTTGACTTTGGGGTTGCCCATGATGGCAGA |
| 183 | HBG1_P7 | GCCAAAGCTGTCAAAGAACCTCTGGGTCCATGGGTAGACAACCAGGAGCC |
| 184 | HBG1_P8 | CTCCAGCATCTTCCACATTCACCTTGCCCCACAGGCTTGTGATAGTAGCC |
| 185 | HBG1_P9 | AAATGACCCATGGCGTCTGGACTAGGAGCTTATTGATAACCTCAGACGTT |
| 186 | HBG2_P1 | GTGATCTCTTAGCAGAATAGATTTATTATTTGATTGCTTGCAGAATAAAG |
| 187 | HBG2_P2 | TCTGCATCATGGGCAGTGAGCTCAGTGGTATCTGGAGGACAGGGCACTGG |
| 188 | HBG2_P3 | TCTTCTGCCAGGAAGCCTGCACCTCAGGGGTGAATTCTTTGCCGAAATGG |
| 189 | HBG2_P4 | ACCAGCACATTTCCCAGGAGCTTGAAGTTCTCAGGATCCACATGCAGCTT |
| 190 | HBG2_P5 | ACTCAGCTGGGCAAAGGTGCCCTTGAGATCATCCAGGTGCTTTATGGCAT |
| 191 | HBG2_P6 | GCACCTTCTTGCCATGTGCCTTGACTTTGGGGTTGCCCATGATGGCAGAG |
| 192 | HBG2_P7 | CCAAAGCTGTCAAAGAACCTCTGGGTCCATGGGTAGACAACCAGGAGCCT |
| 193 | HBG2_P8 | TCCAGCATCTTCCACATTCACCTTGCCCCACAGGCTTGTGATAGTAGCCT |
| 194 | HBG2_P9 | AATGACCCATGGCGTCTGGACTAGGAGCTTATTGATAACCTCAGACGTTC |
| 195 | 5S_GNbac_P1 | ATGCCTGGCAGTTCCCTACTCTCGCATGGGGAGACCCCACACTACCATCG |
| 196 | 5S_GNbac_P2 | ACTTCTGAGTTCGGCATGGGGTCAGGTGGGACCACCGCGCTACGGCCGCC |
| 197 | 16S_GNbac_P1 | GGTTACCTTGTTACGACTTCACCCCAGTCATGAATCACAAAGTGGTAAGT |
| 198 | 16S_GNbac_P2 | AAGCTACCTACTTCTTTTGCAACCCACTCCCATGGTGTGACGGGCGGTGT |
| 199 | 16S_GNbac_P3 | ACGTATTCACCGTGGCATTCTGATCCACGATTACTAGCGATTCCGACTTC |
| 200 | 16S_GNbac_P4 | AGACTCCAATCCGGACTACGACGCACTTTATGAGGTCCGCTTGCTCTCGC |
| 201 | 16S_GNbac_P5 | TGTATGCGCCATTGTAGCACGTGTGTAGCCCTGGTCGTAAGGGCCATGAT |
| 202 | 16S_GNbac_P6 | CCACCTTCCTCCAGTTTATCACTGGCAGTCTCCTTTGAGTTCCCGGCCGG |
| 203 | 16S_GNbac_P7 | GGATAAGGGTTGCGCTCGTTGCGGGACTTAACCCAACATTTCACAACACG |
| 204 | 16S_GNbac_P8 | TGCAGCACCTGTCTCACGGTTCCCGAAGGCACATTCTCATCTCTGAAAAC |
| 205 | 16S_GNbac_P9 | GACCAGGTAAGGTTCTTCGCGTTGCATCGAATTAAACCACATGCTCCACC |
| 206 | 16S_GNbac_P10 | CGTCAATTCATTTGAGTTTTAACCTTGCGGCCGTACTCCCCAGGCGGTCG |
| 207 | 16S_GNbac_P11 | TCCGGAAGCCACGCCTCAAGGGCACAACCTCCAAGTCGACATCGTTTACG |
| 208 | 16S_GNbac_P12 | GTATCTAATCCTGTTTGCTCCCCACGCTTTCGCACTGAGCGTCAGTCTTC |
| 209 | 16S_GNbac_P13 | TTCGCCACCGGTATTCCTCCAGATCTCTACGCATTTCACCGCTACACCTG |

TABLE 1-continued

DNA probe sequences for unwanted RNA depletion

| SEQ ID NO | Probe name | Probe sequence 5'-3' |
|---|---|---|
| 210 | 16S_GNbac_P14 | CTACGAGACTCAAGCTTGCCAGTATCAGATGCAGTTCCCAGGTTGAGCCC |
| 211 | 16S_GNbac_P15 | GACTTAACAAACCGCCTGCGTGCGCTTTACGCCCAGTAATTCCGATTAAC |
| 212 | 16S_GNbac_P16 | ATTACCGCGGCTGCTGGCACGGAGTTAGCCGGTGCTTCTTCTGCGGGTAA |
| 213 | 16S_GNbac_P17 | GTATTAACTTTACTCCCTTCCTCCCCGCTGAAAGTACTTTACAACCCGAA |
| 214 | 16S_GNbac_P18 | CGCGGCATGGCTGCATCAGGCTTGCGCCCATTGTGCAGTATTCCCCACTG |
| 215 | 16S_GNbac_P19 | GTCTGGACCGTGTCTCAGTTCCAGTGTGGCTGGTCATCCTCTCAGACCAG |
| 216 | 16S_GNbac_P20 | TAGGTGAGCCGTTACCCCACCTACTAGCTAATCCCATCTGGGCACATCCG |
| 217 | 16S_GNbac_P21 | AAGGTCCCCCTCTTTGGTCTTGCGACGTTATGCGGTATTAGCTACCGTTT |
| 218 | 16S_GNbac_P22 | CTCCATCAGGCAGTTTCCCAGACATTACTCACCCGTCCGCCACTCGTCAG |
| 219 | 23S_GNbac_P1 | AAGGTTAAGCCTCACGGTTCATTAGTACCGGTTAGCTCAACGCATCGCTG |
| 220 | 23S_GNbac_P2 | CCTATCAACGTCGTCGTCTTCAACGTTCCTTCAGGACCCTTAAAGGGTCA |
| 221 | 23S_GNbac_P3 | GGGGCAAGTTTCGTGCTTAGATGCTTTCAGCACTTATCTCTTCCGCATTT |
| 222 | 23S_GNbac_P4 | CCATTGGCATGACAACCCGAACACCAGTGATGCGTCCACTCCGGTCCTCT |
| 223 | 23S_GNbac_P5 | CCCCCTCAGTTCTCCAGCGCCCACGGCAGATAGGGACCGAACTGTCTCAC |
| 224 | 23S_GNbac_P6 | GCTCGCGTACCACTTTAAATGGCGAACAGCCATACCCTTGGGACCTACTT |
| 225 | 23S_GNbac_P7 | ATGAGCCGACATCGAGGTGCCAAACACCGCCGTCGATATGAACTCTTGGG |
| 226 | 23S_GNbac_P8 | ATCCCCGGAGTACCTTTTATCCGTTGAGCGATGGCCCTTCCATTCAGAAC |
| 227 | 23S_GNbac_P9 | ACCTGCTTTCGCACCTGCTCGCGCCGTCACGCTCGCAGTCAAGCTGGCTT |
| 228 | 23S_GNbac_P10 | CCTCCTGATGTCCGACCAGGATTAGCCAACCTTCGTGCTCCTCCGTTACT |
| 229 | 23S_GNbac_P11 | GCCCCAGTCAAACTACCCACCAGACACTGTCCGCAACCCGGATTACGGGT |
| 230 | 23S_GNbac_P12 | AAACATTAAAGGGTGGTATTTCAAGGTCGGCTCCATGCAGACTGGCGTCC |
| 231 | 23S_GNbac_P13 | CCACCTATCCTACACATCAAGGCTCAATGTTCAGTGTCAAGCTATAGTAA |
| 232 | 23S_GNbac_P14 | TTCCGTCTTGCCGCGGGTACACTGCATCTTCACAGCGAGTTCAATTTCAC |
| 233 | 23S_GNbac_P15 | GACAGCCTGGCCATCATTACGCCATTCGTGCAGGTCGGAACTTACCCGAC |
| 234 | 23S_GNbac_P16 | CTTAGGACCGTTATAGTTACGGCCGCCGTTTACCGGGGCTTCGATCAAGA |
| 235 | 23S_GNbac_P17 | ACCCCATCAATTAACCTTCCGGCACCGGGCAGGCGTCACACCGTATACGT |
| 236 | 23S_GNbac_P18 | CACAGTGCTGTGTTTTAATAAACAGTTGCAGCCAGCTGGTATCTTCGAC |
| 237 | 23S_GNbac_P19 | CCGCGAGGGACCTCACCTACATATCAGCGTGCCTTCTCCCGAAGTTACGG |
| 238 | 23S_GNbac_P20 | TTCCTTCACCCGAGTTCTCTCAAGCGCCTTGGTATTCTCTACCTGACCAC |
| 239 | 23S_GNbac_P21 | GTACGATTTGATGTTACCTGATGCTTAGAGGCTTTTCCTGGAAGCAGGGC |
| 240 | 23S_GNbac_P22 | ACCGTAGTGCCTCGTCATCACGCCTCAGCCTTGATTTTCCGGATTTGCCT |
| 241 | 23S_GNbac_P23 | ACGCTTAAACCGGGACAACCGTCGCCCGGCCAACATAGCCTTCTCCGTCC |
| 242 | 23S_GNbac_P24 | ACCAAGTACAGGAATATTAACCTGTTTCCCATCGACTACGCCTTTCGGCC |
| 243 | 23S_GNbac_P25 | ACTCACCCTGCCCCGATTAACGTTGGACAGGAACCCTTGGTCTTCCGGCG |
| 244 | 23S_GNbac_P26 | CGCTTTATCGTTACTTATGTCAGCATTCGCACTTCTGATACCTCCAGCAT |
| 245 | 23S_GNbac_P27 | TTCGCAGGCTTACAGAACGCTCCCCTACCCAACAACGCATAAGCGTCGCT |
| 246 | 23S_GNbac_P28 | CATGGTTTAGCCCCGTTACATCTTCCGCGCAGGCCGACTCGACCAGTGAG |
| 247 | 23S_GNbac_P29 | TAAATGATGGCTGCTTCTAAGCCAACATCCTGGCTGTCTGGGCCTTCCCA |

TABLE 1-continued

DNA probe sequences for unwanted RNA depletion

| SEQ ID NO | Probe name | Probe sequence 5'-3' |
|---|---|---|
| 248 | 23S_GNbac_P30 | AACCATGACTTTGGGACCTTAGCTGGCGGTCTGGGTTGTTTCCCTCTTCA |
| 249 | 23S_GNbac_P31 | CCCGCCGTGTGTCTCCCGTGATAACATTCTCCGGTATTCGCAGTTTGCAT |
| 250 | 23S_GNbac_P32 | GGATGACCCCCTTGCCGAAACAGTGCTCTACCCCCGGAGATGAATTCACG |
| 251 | 23S_GNbac_P33 | AGCTTTCGGGGAGAACCAGCTATCTCCCGGTTTGATTGGCCTTTCACCCC |
| 252 | 23S_GNbac_P34 | CGCTAATTTTTCAACATTAGTCGGTTCGGTCCTCCAGTTAGTGTTACCCA |
| 253 | 23S_GNbac_P35 | ATGGCTAGATCACCGGGTTTCGGGTCTATACCCTGCAACTTAACGCCCAG |
| 254 | 23S_GNbac_P36 | CCTTCGGCTCCCCTATTCGGTTAACCTTGCTACAGAATATAAGTCGCTGA |
| 255 | 23S_GNbac_P37 | GTACGCAGTCACACGCCTAAGCGTGCTCCCACTGCTTGTACGTACACGGT |
| 256 | 23S_GNbac_P38 | ACTCCCCTCGCCGGGGTTCTTTTCGCCTTTCCCTCACGGTACTGGTTCAC |
| 257 | 23S_GNbac_P39 | AGTATTTAGCCTTGGAGGATGGTCCCCCCATATTCAGACAGGATACCACG |
| 258 | 23S_GNbac_P40 | ATCGAGCTCACAGCATGTGCATTTTTGTGTACGGGGCTGTCACCCTGTAT |
| 259 | 23S_GNbac_P41 | ACGCTTCCACTAACACACACTGATTCAGGCTCTGGGCTGCTCCCCGTT |
| 260 | 23S_GNbac_P42 | GGGGAATCTCGGTTGATTTCTTTTCCTCGGGGTACTTAGATGTTTCAGTT |
| 261 | 23S_GNbac_P43 | ATTAACCTATGGATTCAGTTAATGATAGTGTGTCGAAACACACTGGGTTT |
| 262 | 23S_GNbac_P44 | GCCGGTTATAACGGTTCATATCACCTTACCGACGCTTATCGCAGATTAGC |
| 263 | 5S_GPbac_P1 | GCTTGGCGGCGTCCTACTCTCACAGGGGGAAACCCCCGACTACCATCGGC |
| 264 | 5S_GPbac_P2 | TTCCGTGTTCGGTATGGGAACGGGTGTGACCTCTTCGCTATCGCCACCAA |
| 265 | 16S_GPbac_P1 | TAGAAAGGAGGTGATCCAGCCGCACCTTCCGATACGGCTACCTTGTTACG |
| 266 | 16S_GPbac_P2 | TCTGTCCCACCTTCGGCGGCTGGCTCCTAAAAGGTTACCTCACCGACTTC |
| 267 | 16S_GPbac_P3 | TCGTGGTGTGACGGGCGGTGTGTACAAGGCCCGGGAACGTATTCACCGCG |
| 268 | 16S_GPbac_P4 | ATTACTAGCGATTCCAGCTTCACGCAGTCGAGTTGCAGACTGCGATCCGA |
| 269 | 16S_GPbac_P5 | GTGGGATTGGCTTAACCTCGCGGTTTCGCTGCCCTTTGTTCTGTCCATTG |
| 270 | 16S_GPbac_P6 | CCAGGTCATAAGGGGCATGATGATTTGACGTCATCCCCACCTTCCTCCGG |
| 271 | 16S_GPbac_P7 | CACCTTAGAGTGCCCAACTGAATGCTGGCAACTAAGATCAAGGGTTGCGC |
| 272 | 16S_GPbac_P8 | ACCCAACATCTCACGACACGAGCTGACGACAACCATGCACCACCTGTCAC |
| 273 | 16S_GPbac_P9 | GACGTCCTATCTCTAGGATTGTCAGAGGATGTCAAGACCTGGTAAGGTTC |
| 274 | 16S_GPbac_P10 | ATTAAACCACATGCTCCACCGCTTGTGCGGGCCCCCGTCAATTCCTTTGA |
| 275 | 16S_GPbac_P11 | CCGTACTCCCCAGGCGGAGTGCTTAATGCGTTAGCTGCAGCACTAAGGGG |
| 276 | 16S_GPbac_P12 | ACTTAGCACTCATCGTTTACGGCGTGGACTACCAGGGTATCTAATCCTGT |
| 277 | 16S_GPbac_P13 | TCGCTCCTCAGCGTCAGTTACAGACCAGAGAGTCGCCTTCGCCACTGGTG |
| 278 | 16S_GPbac_P14 | ACGCATTTCACCGCTACACGTGGAATTCCACTCTCCTCTTCTGCACTCAA |
| 279 | 16S_GPbac_P15 | ATGACCCTCCCCGGTTGAGCCGGGGCTTTCACATCAGACTTAAGAAACC |
| 280 | 16S_GPbac_P16 | ACGCCCAATAATTCCGGACAACGCTTGCCACCTACGTATTACCGCGGCTG |
| 281 | 16S_GPbac_P17 | CCGTGGCTTTCTGGTTAGGTACCGTCAAGGTACCGCCCTATTCGAACGGT |
| 282 | 16S_GPbac_P18 | ACAACAGAGCTTTACGATCCGAAAACCTTCATCACTCACGCGGCGTTGCT |
| 283 | 16S_GPbac_P19 | CCATTGCGGAAGATTCCCTACTGCTGCCTCCCGTAGGAGTCTGGGCCGTG |
| 284 | 16S_GPbac_P20 | GGCCGATCACCCTCTCAGGTCGGCTACGCATCGTCGCCTTGGTGAGCCGT |

TABLE 1-continued

DNA probe sequences for unwanted RNA depletion

| SEQ ID NO | Probe name | Probe sequence 5'-3' |
|---|---|---|
| 285 | 16S_GPbac_P21 | CTAATGCGCCGCGGGTCCATCTGTAAGTGGTAGCCGAAGCCACCTTTTAT |
| 286 | 16S_GPbac_P22 | TTCAAACAACCATCCGGTATTAGCCCCGGTTTCCCGGAGTTATCCCAGTC |
| 287 | 16S_GPbac_P23 | CCACGTGTTACTCACCCGTCCGCCGCTAACATCAGGGAGCAAGCTCCCAT |
| 288 | 16S_GPbac_P24 | GCATGTATTAGGCACGCCGCCAGCGTTCGTCCTGAGCCAGGATCAAACTC |
| 289 | 23S_GPbac_P1 | TGGTTAAGTCCTCGATCGATTAGTATCTGTCAGCTCCATGTGTCGCCACA |
| 290 | 23S_GPbac_P2 | TATCAACCTGATCATCTTTCAGGGATCTTACTTCCTTGCGGAATGGGAAA |
| 291 | 23S_GPbac_P3 | GGCTTCATGCTTAGATGCTTTCAGCACTTATCCCGTCCGCACATAGCTAC |
| 292 | 23S_GPbac_P4 | GCAGAACAACTGGTACACCAGCGGTGCGTCCATCCCGGTCCTCTCGTACT |
| 293 | 23S_GPbac_P5 | CAAATTTCCTGCGCCCGCGACGGATAGGGACCGAACTGTCTCACGACGTT |
| 294 | 23S_GPbac_P6 | GTACCGCTTTAATGGGCGAACAGCCCAACCCTTGGGACTGACTACAGCCC |
| 295 | 23S_GPbac_P7 | CGACATCGAGGTGCCAAACCTCCCCGTCGATGTGGACTCTTGGGGGAGAT |
| 296 | 23S_GPbac_P8 | GGGGTAGCTTTTATCCGTTGAGCGATGGCCCTTCCATGCGGAACCACCGG |
| 297 | 23S_GPbac_P9 | TTTCGTCCCTGCTCGACTTGTAGGTCTCGCAGTCAAGCTCCCTTGTGCCT |
| 298 | 23S_GPbac_P10 | GATTTCCAACCATTCTGAGGGAACCTTTGGGCGCCTCCGTTACCTTTTAG |
| 299 | 23S_GPbac_P11 | GTCAAACTGCCCACCTGACACTGTCTCCCCGCCCGATAAGGGCGGCGGGT |
| 300 | 23S_GPbac_P12 | GCCAGGGTAGTATCCCACCGATGCCTCCACCGAAGCTGGCGCTCCGGTTT |
| 301 | 23S_GPbac_P13 | ATCCTGTACAAGCTGTACCAACATTCAATATCAGGCTGCAGTAAAGCTCC |
| 302 | 23S_GPbac_P14 | CCTGTCGCGGGTAACCTGCATCTTCACAGGTACTATAATTTCACCGAGTC |
| 303 | 23S_GPbac_P15 | GCCCAGATCGTTGCGCCTTTCGTGCGGGTCGGAACTTACCCGACAAGGAA |
| 304 | 23S_GPbac_P16 | ACCGTTATAGTTACGGCCGCCGTTTACTGGGGCTTCAATTCGCACCTTCG |
| 305 | 23S_GPbac_P17 | CCTCTTAACCTTCCAGCACCGGGCAGGCGTCAGCCCCTATACTTCGCCTT |
| 306 | 23S_GPbac_P18 | CCTGTGTTTTTGCTAAACAGTCGCCTGGGCCTATTCACTGCGGCTCTCTC |
| 307 | 23S_GPbac_P19 | CAGAGCACCCCTTCTCCCGAAGTTACGGGGTCATTTTGCCGAGTTCCTTA |
| 308 | 23S_GPbac_P20 | ATCACCTTAGGATTCTCTCCTCGCCTACCTGTGTCGGTTTGCGGTACGGG |
| 309 | 23S_GPbac_P21 | TAGAGGCTTTTCTTGGCAGTGTGGAATCAGGAACTTCGCTACTATATTTC |
| 310 | 23S_GPbac_P22 | TCAGCCTTATGGGAAACGGATTTGCCTATTTCCCAGCCTAACTGCTTGGA |
| 311 | 23S_GPbac_P23 | CCGCGCTTACCCTATCCTCCTGCGTCCCCCCATTGCTCAAATGGTGAGGA |
| 312 | 23S_GPbac_P24 | TCAACCTGTTGTCCATCGCCTACGCCTTTCGGCCTCGGCTTAGGTCCCGA |
| 313 | 23S_GPbac_P25 | CGAGCCTTCCTCAGGAAACCTTAGGCATTCGGTGGAGGGGATTCTCACCC |
| 314 | 23S_GPbac_P26 | TACCGGCATTCTCACTTCTAAGCGCTCCACCAGTCCTTCCGGTCTGGCTT |
| 315 | 23S_GPbac_P27 | GCTCTCCTACCACTGTTCGAAGAACAGTCCGCAGCTTCGGTGATACGTTT |
| 316 | 23S_GPbac_P28 | TCGGCGCAGAGTCACTCGACCAGTGAGCTATTACGCACTCTTTAAATGGT |
| 317 | 23S_GPbac_P29 | AACATCCTGGTTGTCTAAGCAACTCCACATCCTTTTCCACTTAACGTATA |
| 318 | 23S_GPbac_P30 | TGGCGGTCTGGGCTGTTTCCCTTTCGACTACGGATCTTATCACTCGCAGT |
| 319 | 23S_GPbac_P31 | AAGTCATTGGCATTCGGAGTTTGACTGAATTCGGTAACCCGGTAGGGGCC |
| 320 | 23S_GPbac_P32 | GCTCTACCTCCAAGACTCTTACCTTGAGGCTAGCCCTAAAGCTATTTCGG |
| 321 | 23S_GPbac_P33 | TCCAGGTTCGATTGGCATTTCACCCCTACCCACACCTCATCCCCGCACTT |
| 322 | 23S_GPbac_P34 | TTCGGGCCTCCATTCAGTGTTACCTGAACTTCACCCTGGACATGGGTAGA |

TABLE 1-continued

DNA probe sequences for unwanted RNA depletion

| SEQ ID NO | Probe name | Probe sequence 5'-3' |
|---|---|---|
| 323 | 23S_GPbac_P35 | TCTACGACCACGTACTCATGCGCCCTATTCAGACTCGCTTTCGCTGCGGC |
| 324 | 23S_GPbac_P36 | TAACCTTGCACGGGATCGTAACTCGCCGGTTCATTCTACAAAAGGCACGC |
| 325 | 23S_GPbac_P37 | GGCTCTGACTACTTGTAGGCACACGGTTTCAGGATCTCTTTCACTCCCCT |
| 326 | 23S_GPbac_P38 | ACCTTTCCCTCACGGTACTGGTTCACTATCGGTCACTAGGGAGTATTTAG |
| 327 | 23S_GPbac_P39 | CTCCCGGATTCCGACGGAATTTCACGTGTTCCGCCGTACTCAGGATCCAC |
| 328 | 23S_GPbac_P40 | GTTTTGACTACAGGGCTGTTACCTCCTATGGCGGGCCTTTCCAGACCTCT |
| 329 | 23S_GPbac_P41 | CTTTGTAACTCCGTACAGAGTGTCCTACAACCCCAAGAGGCAAGCCTCTT |
| 330 | 23S_GPbac_P42 | CGTTTCGCTCGCCGCTACTCAGGGAATCGCATTTGCTTTCTCTTCCTCCG |
| 331 | 23S_GPbac_P43 | CAGTTCCCCGGGTCTGCCTTCTCATATCCTATGAATTCAGATATGGATAC |
| 332 | 23S_GPbac_P44 | GGTGGGTTTCCCCATTCGGAAATCTCCGGATCAAAGCTTGCTTACAGCTC |
| 333 | 23S_GPbac_P45 | TGTTCGTCCCGTCCTTCATCGGCTCCTAGTGCCAAGGCATCCACCGTGCG |
| 334 | 16S:A1 | AAACTAGATTCGAATATAACAAAACATTACATCCTCATCCAATCCCTTTT |
| 335 | 16S:A2 | GCGGTGTGTGCAAGGAGCAGGGACGTATTCACCGCGCGATTGTGACACGC |
| 336 | 16S:A3 | GCCTTTCGGCGTCGGAACCCATTGTCTCAGCCATTGTAGCCCGCGTGTTG |
| 337 | 16S:A4 | GCATACGGACCTACCGTCGTCCACTCCTTCCTCCTATTTATCATAGGCGG |
| 338 | 16S:A5 | CGGCATCCAAAAAAGGATCCGCTGGTAACTAAGAGCGTGGGTCTCGCTCG |
| 339 | 16S:A6 | CAACCTGGCTATCATACAGCTGTCGCCTCTGGTGAGATGTCCGGCGTTGA |
| 340 | 16S:A7 | AGGCTCCACGCGTTGTGGTGCTCCCCCGCCAATTCCTTTAAGTTTCAGTC |
| 341 | 16S:A8 | CCAGGCGGCGGACTTAACAGCTTCCCTTCGGCACTGGGACAGCTCAAAGC |
| 342 | 16S:A9 | TCCGCATCGTTTACAGCTAGGACTACCCGGGTATCTAATCCGGTTCGCGC |
| 343 | 16S:A10 | TTCCCACAGTTAAGCTGCAGGATTTCACCAGAGACTTATTAAACCGGCTA |
| 344 | 16S:A12 | CTCTTATTCCAAAAGCTCTTTACACTAATGAAAAGCCATCCCGTTAAGAA |
| 345 | 16S:A13 | CCCCCGTCGCGATTTCTCACATTGCGGAGGTTTCGCGCCTGCTGCACCCC |
| 346 | 16S:A14 | TTGTCTCAGGTTCCATCTCCGGGCTCTTGCTCTCACAACCCGTACCGATC |
| 347 | 16S:A16 | CATTACCTAACCAACTACCTAATCGGCCGCAGACCCATCCTTAGGCGAAA |
| 348 | 16S:A17 | AAACCATTACAGGAATAATTGCCTATCCAGTATTATCCCCAGTTTCCCAG |
| 349 | 16S:A18 | AAGGGTAGGTTATCCACGTGTTACTGAGCCGTACGCCACGAGCCTAAACT |
| 350 | 23S:A1 | ACCTAGCGCGTAGCTGCCCGGCACTGCCTTATCAGACAACCGGTCGACCA |
| 351 | 23S:A2 | CGTTCCTCTCGTACTGGAGCCACCTTCCCCTCAGACTACTAACACATCCA |
| 352 | 23S:A3 | CCTGTCTCACGACGGTCTAAACCCAGCTCACGTTCCCCTTTAATGGGCGA |
| 353 | 23S:A4 | GGTGCTGCTGCACACCCAGGATGGAAAGAACCGACATCGAAGTAGCAAGC |
| 354 | 23S:A5 | GGCTCTTGCCTGCGACCACCCAGTTATCCCCGAGGTAGTTTTTCTGTCAT |
| 355 | 23S:A6 | AGGAGGACTCTGAGGTTCGCTAGGCCCGGCTTTCGCCTCTGGATTTCTTG |
| 356 | 23S:A7 | CAAAGTAAGTTAGAAACACAGTCATAAGAAAGTGGTGTCTCAAGAACGAA |
| 357 | 23S:A8 | GACTTATAATCGAATTCTCCCACTTACACTGCATACCTATAACCAAGCTT |
| 358 | 23S:A9 | GTAAAACTCTACGGGGTCTTCGCTTCCCAATGGAAGACTCTGGCTTGTGC |
| 359 | 23S:A10 | TCACTAAGTTCTAGCTAGGGACAGTGGGGACCTCGTTCTACCATTCATGC |

TABLE 1-continued

DNA probe sequences for unwanted RNA depletion

| SEQ ID NO | Probe name | Probe sequence 5'-3' |
|---|---|---|
| 360 | 23S:A11 | CGACAAGGCATTTCGCTACCTTAAGAGGGTTATAGTTACCCCCGCCGTTT |
| 361 | 23S:A12 | AACTGAACTCCAGCTTCACGTGCCAGCACTGGGCAGGTGTCGCCCTCTGT |
| 362 | 23S:A13 | CTAGCAGAGAGCTATGTTTTTATTAAACAGTCGGGCCCCCCTAGTCACTG |
| 363 | 23S:A14 | TTAAAACGCCTTAGCCTACTCAGCTAGGGGCACCTGTGACGGATCTCGGT |
| 364 | 23S:A15 | ACAAAACTAACTCCCTTTTCAAGGACTCCATGAATCAGTTAAACCAGTAC |
| 365 | 23S:A16 | ATAATGCCTACACCTGGTTCTCGCTATTACACCTCTCCCCAGGCTTAAAC |
| 366 | 23S:A17 | CAATCCTACAAAACATATCTCGAAGTGTCAGAAATTAGCCCTCAACGTCA |
| 367 | 23S:A18 | CTTTGCTGCTACTACTACCAGGATCCACATACCTGCAAGGTCCAAAGGAA |
| 368 | 23S:A19 | CAACCCACACAGGTCGCCACTCTACACAATCACCAAAAAAAAGGTGTTCC |
| 369 | 23S:A20 | GGATTAATTCCCGTCCATTTTAGGTGCCTCTGACCTCGATGGGTGATCTG |
| 370 | 23S:A21 | AGGGTGGCTGCTTCTAAGCCCACCTTCCCATTGTCTTGGGCCAAAGACTC |
| 371 | 23S:A22 | GTATTTAGGGGCCTTAACCATAGTCTGAGTTGTTTCTCTTTCGGACACA |
| 372 | 23S:A23 | CCTCACTCCAACCTTCTACGACGGTGACGAGTTCGGAGTTTTACAGTACG |
| 373 | 23S:A24 | CCCTAAACGTCCAATTAGTGCTCTACCCCGCCACCAACCTCCAGTCAGGC |
| 374 | 23S:A25 | AATAGATCGACCGGCTTCGGGTTTCAATGCTGTGATTCCAGGCCCTATTA |
| 375 | 23S:A26 | ACAACGCTGCGGGCATATCGGTTTCCCTACGACTACAAGGATAAAAACCT |
| 376 | 23S:A27 | ACAAAGAACTCCCTGGCCCGTGTTTCAAGACGGACGATGCAACACTAGTC |
| 377 | 23S:A28 | ACAATGTTACCACTGATTCTTTCGGAAGAATTCATTCCTTACGCGCCACA |
| 378 | 23S:A29 | CTGGTTTCAGGTACTTTTCACCCCCCTATAGGGGTACTTTTCAGCATTCC |
| 379 | 23S:A30 | CTCTATCGGTCTTGAGACGTATTTAGAATTGGAAGTTGATGCCTCCCACA |
| 380 | 23S:A31 | ATCACCCTCTACGGTTCTAAAATTCCAAATAAAATTCGATTTATCCCACG |
| 381 | 23S:A32 | TCTATACACCACATCTCCCTAATATTACTAAAAGGGATTCAGTTTGTTCT |
| 382 | 23S:A33 | GCCGTTACTAACGACATCGCATATTGCTTTCTTTTCCTCCGCCTACTAAG |
| 383 | 23S:A34 | GGGTTCCCAATCCTACACGGATCAACACAAAAAAAATGTGCTAGGAAGTC |
| 384 | 5S:A1 | ACTACTGGGATCGAAACGAGACCAGGTATAACCCCCATGCTATGACCGCA |
| 385 | MM_16S_P10 | GCGTATGCCTGGAGAATTGGAATTCTTGTTACTCATACTAACAGTGTTGC |
| 386 | MM_16S_P11 | GATTAACCCAATTTTAAGTTTAGGAAGTTGGTGTAAATTATGGAATTAAT |
| 387 | MM_16S_P12 | AGCTTGAACGCTTTCTTTATTGGTGGCTGCTTTTAGGCCTACAATGGTTA |
| 388 | MM_16S_P13 | ATTATTCACTATTAAAGGTTTTTTCCGTTCCAGAAGAGCTGTCCCTCTTT |
| 389 | MM_16S_P14 | CTTACTTTTTGATTTTGTTGTTTTTTAGCAAGTTTAAAATTGAACTTAA |
| 390 | MM_16S_P15 | AACCAGCTATCACCAAGCTCGTTAGGCTTTTCACCTCTACCTAAAAATCT |
| 391 | MM_16S_P7 | AATACTTGTAATGCTAGAGGTGATGTTTTTGGTAAACAGGCGGGGTTCTT |
| 392 | MM_16S_P8 | TTTATCTTTTTGGATCTTTCCTTTAGGCATTCCGGTGTTGGGTTAACAGA |
| 393 | MM_16S_P9 | TTATTTATAGTGTGATTATTGCCTATAGTCTGATTAACTAACAATGGTTA |
| 394 | RN_16S_P4 | AGTGATTGTAGTTGTTTATTCACTATTTAAGGTTTTTTCCTTTTCCTAAA |
| 395 | RN_16S_P5 | TGGCTATATTTTAAGTTTACATTTTGATTTGTTGTTCTGATGGTAAGCTT |
| 396 | RN_16S_P6 | TTTTTTTAATCTTTCCTTAAAGCACGCCTGTGTTGGGCTAACGAGTTAGG |
| 397 | RN_16S_P7 | TGTTGGGTTAGTACCTATGATTCGATAATTGACAATGGTTATCCGGGTTG |

TABLE 1-continued

DNA probe sequences for unwanted RNA depletion

| SEQ ID NO | Probe name | Probe sequence 5'-3' |
|---|---|---|
| 398 | RN_16S_P8 | AGGAGAATTGGTTCTTGTTACTCATATTAACAGTATTTCATCTATGGATC |
| 399 | RN_16S_P9 | TTTGTGATATAGGAATTTATTGAGGTTTGTGGAATTAGTGTGTGTAAGTA |
| 400 | MM_28S_P1 | GCCGGGGAGTGGGTCTTCCGTACGCCACATTTCCCACGCCGCGACGCGCG |
| 401 | MM_28S_P10 | ACCTCGGGCCCCCGGGCGGGGCCCTTCACCTTCATTGCGCCACGGCGGCT |
| 402 | MM_28S_P14 | TCGCGTCCAGAGTCGCCGCCGCCGCCGGCCCCCCGAGTGTCCGGGCCCCC |
| 403 | MM_28S_P15 | CGCTGGTTCCTCCCGCTCCGGAACCCCCGCGGGGTTGGACCCGCCGCCCC |
| 404 | MM_28S_P16 | CGCCGACCCCCGACCCGCCCCCCGACGGGAAGAAGGAGGGGGAAGAGAG |
| 405 | MM_28S_P17 | GGGACGACGGGGCCCCGCGGGGAAGAGGGGAGGGCGGGCCCGGGCGGAAA |
| 406 | MM_28S_P18 | GGCGCCGCGCGGAAAACCGCGGCCCGGGGGGCGGACCCGGCGGGGGAACA |
| 407 | MM_28S_P19 | CCCCCACACGCGCGGGACACGCCCGCCCGCCCCCGCCACGCACCTCGGGA |
| 408 | MM_28S_P2 | CACCCGCTTTGGGCTGCATTCCCAAGCAACCCGACTCCGGGAAGACCCGA |
| 409 | MM_28S_P20 | TGGAGCGAGGCCCCGCGGGGAGGGGACCCGCGCCGGCACCCGCCGGGCTC |
| 410 | MM_28S_P21 | CGAGGCCGGCGTGCCCCGACCCCGACGCGAGGACGGGGCCGGGCGCCGGG |
| 411 | MM_28S_P22 | TCCCCGGAGCGGGTCGCGCCCGCCCGCACGCGCGGGACGGACGCTTGGCG |
| 412 | MM_28S_P23 | TCCACACGAACGTGCGTTCAACGTGACGGGCGAGAGGGCGGCCCCCTTTC |
| 413 | MM_28S_P24 | TCCCAAGACGAACGGCTCTCCGCACCGGACCCCGGTCCCGACGCCCGGCG |
| 414 | MM_28S_P25 | CCGCCGCGGGGACGACGCGGGGACCCCGCCGAGCGGGACGGACGGGGAC |
| 415 | MM_28S_P3 | GCACCGCCACGGTGGAAGTGCGCCCGGCGGCGGCCGGTCGCCGGCCGGGG |
| 416 | MM_28S_P6 | CCCACCGGGCCCCGAGAGAGGCGACGAGGGGGGTGGGAGAGCGGTCGCG |
| 417 | MM_28S_P7 | CCCGGCCCCCACCCCCACGCCCGCCCGGGAGGCGGACGGGGGAGAGGGA |
| 418 | MM_28S_P8 | TATCTGGCTTCCTCGGCCCCGGGATTCGGCGAAAGCGCGGCCGGAGGGCT |
| 419 | MM_28S_P9 | CGCCGCCGACCCCGTGCGCTCGGCTTCGTCGGGAGACGCGTGACCGACGG |
| 420 | RN_28S_P12 | GCGCCCCCCGCACCCGCCCCGTCCCCCCGCGGACGGGGAAGAAGGGAG |
| 421 | RN_28S_P14 | CGAACCCCGGGAACCCCCGACCCCGCGGAGGGGGAAGGGGAGGACGAGG |
| 422 | RN_28S_P16 | CACCCGGGGGGCGACGAGGCGGGGACCCGCCGGACGGGGACGGACGGGG |
| 423 | RN_28S_P17 | GCCAACCGAGGCTCCTTCGGCGCTGCCGTATCGTTCCGCTTGGGCGGATT |
| 424 | RN_28S_P4 | CCCGGGCCCCCGGACCCCCGAGAGGGACGACGGAGGCGACGGGGGGTGGG |
| 425 | RN_28S_P5 | TGGGAGGGGCGGCCCGGCCCCCGCGACCGCCCCCCTTTCCGCCACCCCAC |
| 426 | RN_28S_P6 | GGGAGAGGCCGGGGGGAGAGCGCGGCGACGGGTATCCGGCTCCCTCGGCC |
| 427 | RN_28S_P7 | CGCTGCTGCCGGGGGCTGTAACACTCGGGGCGGGTGGTCCGGCGCCCA |
| 428 | RN_28S_P8 | CGCCGCCGACCCCGTGCGCTCGGCTTCGCTCCCCCCACCCCGAGAAGGG |

In one embodiment, the RNA sample is from a human and the DNA probe set includes probes specific to human unwanted RNA species such as rRNA and mitochondrial mRNA transcripts as described in this disclosure. In another embodiment, a DNA probe set for depleting unwanted RNA from a human RNA sample includes probes specific to human rRNA and mitochondrial mRNA transcripts, and probes specific to Gram positive and Gram negative unwanted RNA transcripts as described in this disclosure. In a further embodiment, a DNA probe set for depleting unwanted RNA from a human RNA sample includes probes specific to an Archaea bacterial species, an example of which is M. smithii as described in this disclosure. As such, in some embodiments, a DNA probe set for depleting rRNA from a human RNA sample comprises only probes directed to human unwanted RNA species or comprises a mixed DNA probe set that targets non-human unwanted RNA transcripts as well. A skilled artisan will understand that the probe set to be used for RNA depletion will depend on the research intentions for the sample, the environment from which the sample was taken, and any other factors that lead into an experimental design for RNA depletion of an RNA sample.

In one embodiment, the RNA sample is from a non-human eukaryote and the DNA probe set includes probes specific to unwanted RNA in that eukaryotic sourced sample. For example, if the RNA sample is from a mouse or rat, the DNA probe set would include probes specific to mouse or rat unwanted RNA species, which may also include DNA probes specific to unwanted Gram positive and Gram negative bacterial RNA species as well, or other bacterial species such as Archaea species.

In some embodiments, the DNA probes do not hybridize to the entire contiguous length of an RNA species to be deleted. Surprisingly, it was found during experimentation that the full length sequence of a RNA species targeted for depletion need not be targeted with a full-length DNA probe, or a probe set that tiles contiguously over the entire RNA sequence; indeed the DNA probes described herein leave gaps such that the DNA:RNA hybrids formed are not contiguous. Surprisingly, gaps of at least 5 nt, 10 nt, 15 nt or 20 nt between DNA:RNA hybrids provided efficient RNA depletion. Further, probe sets that include gaps can hybridize more efficiently to the unwanted RNA, as the DNA probes do not hinder hybridization of adjacent probes as could potentially occur with probes that cover the whole RNA sequence targeted for depletion, or probes that overlap one another.

In addition, probe sets can be supplemented to improve RNA depletion methods for a given species. A method of supplementing a probe set for use in depleting off-target RNA nucleic acid molecules from a nucleic acid sample can comprise: a) contacting a nucleic acid sample comprising at least one RNA or DNA target sequence and at least one off-target RNA molecule from a first species with a probe set comprising at least two DNA probes complementary to discontiguous sequences along the full length of the at least one off-target RNA molecule from a second species, thereby hybridizing the DNA probes to the off-target RNA molecules to form DNA:RNA hybrids, wherein each DNA:RNA hybrid is at least 5 bases apart, or at least 10 bases apart, along a given off-target RNA molecule sequence from any other DNA:RNA hybrid; b) contacting the DNA:RNA hybrids with a ribonuclease that degrades the RNA from the DNA:RNA hybrids, thereby degrading the off-target RNA molecules in the nucleic acid sample to form a degraded mixture; c) separating the degraded RNA from the sample; d) sequencing the remaining RNA from the sample; e) evaluating the remaining RNA sequences for the presence of off-target RNA molecules from the first species, thereby determining gap sequence regions; and f) supplementing the probe set with at least one DNA probe complementary to discontiguous sequences in one or more of the gap sequence regions. In some embodiments, the gap sequence regions comprise at least 50, or at least 60, or at least 70 base pairs. In some embodiments, the first species is a non-human species and the second species is human. In some embodiments, the first species is rat or mouse. Exemplary methods for supplementing a probe set for improved depletion of off-target rRNA nucleic acid molecules in mouse samples are outlined in Example 8 and FIG. 9.

In some embodiments, a first species is a non-human species and a second species is human. In some embodiments, a first species is rat or mouse. In some embodiments, the second species is human, Gram-positive bacteria, Gram-negative bacteria, or a mixture thereof.

Compositions and Kits

In one embodiment, the present disclosure relates to compositions comprising a probe set as described herein. In some embodiments, the composition comprises the probe set and a ribonuclease capable of degrading RNA in a DNA:RNA hybrid, such as RNase H or Hybridase. In some embodiments, the probe set comprises at least two DNA probes complementary to at least one off-target rRNA molecule in the nucleic acid sample, wherein the probes are non-overlapping and are discontiguous relative to the length of the off-target rRNA molecule (e.g., at least 5 or at least 10 bases apart along the full length). In some embodiments, the composition comprises the probe set comprising at least two DNA probes hybridized to at least one off-target RNA molecule, wherein each DNA probe is hybridized at least 5, or at least 10, bases apart along the length of the off-target RNA molecule from any other DNA probe in the probe set. In some embodiments, the composition comprises a nucleic acid destabilizing chemical such as formamide, betaine, DMSO, glycerol, or derivatives or mixtures thereof. In one embodiment, the destabilizing chemical is formamide or a derivative thereof which is present in a concentration of between 10-45% of the hybridization total reaction volume.

In one embodiment, the present disclosure describes a kit comprising a probe set comprising at least two DNA probes complementary to discontiguous sequences along the full length of at least one off-target rRNA molecule (e.g., at least 5 bases apart or at least 10 bases apart along the full length) in a nucleic acid sample, a ribonuclease capable of degrading RNA in a DNA:RNA hybrid. In some embodiments, the probe set comprises any of the DNA probes described herein, or any combination thereof.

In some embodiments, a kit comprises a buffer and nucleic acid purification medium. In some embodiments, the kit comprises one or more of a buffer, a nucleic acid purification medium, and a DNA probe set as described herein. In some embodiments, the probe set comprises two or more sequences of SEQ ID NOs: 1-333. In some embodiments, the probe set comprises two or more sequences of SEQ ID NOs: 1-428. In some embodiments, a probe set comprises two or more, or five or more, or 10 or more, or 25 or more, or 50 or more, or 100 or more, or 150 or more, or 200 or more, or 250 or more, or 300 or more, or 350 or more, or 377 sequences from SEQ ID NOs: 1-377 (human, Gram-positive bacteria, Gram-negative bacteria, and Archaea). In some embodiments, a probe set comprises two or more, or five or more, or 10 or more, or 25 or more, or 50 or more, or 100 or more, or 150 or more, or 200 or more, or 250 or more, or 300 or more, or 350 or more, or 384 sequences from SEQ ID NOs: 1-333 and SEQ ID NOs: 378-428 (human, Gram-positive bacteria, Gram-negative bacteria, mouse, and rat). In some embodiments, a probe set comprises two or more, or five or more, or 10 or more, or 25 or more, or 44 sequences from SEQ ID NOs: 334-377 (Archaea). In some embodiments, a probe set comprises two or more, or five or more, or 10 or more, or 25 or more, or 50 or more, or 51 sequences from SEQ ID NOs: 378-428 (mouse and rat).

In some embodiments, the kit comprises: 1) probe set as described herein; 2) a ribonuclease; 3) a DNase; and 4) RNA purification beads. In some embodiments, the kit comprises an RNA depletion buffer, a probe depletion buffer, and a probe removal buffer.

Analysis of Depleted Samples

The disclosed methods also find utility in analyzing transcriptomes from single or mixed samples. Transcriptomic analysis can be impeded by high relative abundance of ribosomal RNA, for example a sample may comprise ≥85% of rRNA molecules in total RNA from bacterial cells. With such high amounts of rRNA competing for sequencing or other analysis reagents it can be difficult to focus on the more informative parts of a transcriptome which can get lost in the background of unwanted rRNA analysis. The disclosed methods can facilitate rich transcriptome analysis of microbial or eukaryotic isolates, for example, at low inputs of DNA, leading to lower rRNA sequencing reads, enabling lower sequencing costs and enabling metatranscriptomic analysis of low biomass samples. This is exemplified in Example 4, where low input amounts (<80 ng) from mixed samples were evaluated using the RNase H rRNA depletion methods described in this disclosure. The methods described herein can be used in conjunction with a variety of downstream applications, such as creating libraries for nucleic acid sequencing techniques, using the enriched samples in RT-PCR followed by microarray analysis, PCR, qPCR, etc. However, it should be understood that the enriched RNA samples resulting from the RNA depletion methods described here are not limited to any particular downstream application, such as sequencing.

As an example, the RNA depleted samples can be used to create sequencing libraries, such that the libraries created can be attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

Sequencing methodologies that can leverage the RNA depletion workflows and RNA enriched samples include, but are not limited to, cycle sequencing that is accomplished by stepwise addition of reversible terminator nucleotides containing, for example, a cleavable or photobleachable dye. Examples of Illumina instruments that can leverage the methods described herein include HiSeq™, MiSeq™, NextSeq™, NovaSeq™, NextSeg™, and iSeq™ commercial instruments.

Additional sequencing techniques include sequencing by ligation. Such techniques utilize DNA ligase to incorporate oligonucleotides and identify the incorporation of such oligonucleotides.

Further, nanopore sequencing can also use the disclosed RNA depleted samples for library preparation. Nanopore sequencing methods sequence a strand of nucleic acids that pass through a pore wherein change is current through the pore is characteristic of which nucleotide is passing through the pore.

Further, sequencing using real-time monitoring of DNA polymerase activity can utilize the RNA depleted samples.

Additional SBS technologies that can create libraries for sequencing using the RNA depleted samples described herein include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary).

Additional downstream application that can leverage the enriched samples following RNA depletion as described herein include PCR, qPCR, microarray analysis, etc. For example, microarray analysis is a powerful technique for studying gene expression. The enriched samples can be used in microarray analysis by converting the enriched RNA to cDNA following methods known to a skilled artisan (e.g., reverse-transcriptase polymerase chain reaction RT-PCR). The cDNA could then be immobilized on substrates, microarray probes applied and expression analysis determined following any number of microarray analysis methodologies (for example, Agilent, Affymetrix, and Illumina to name a few sell commercial microarray analysis systems). Polymerase chain reaction (PCR) or quantitative PCR (qPCR) could also utilize the enriched sample as a substrate following established techniques (Current Protocols for Molecular Biology).

As such, the RNA depleted samples resulting from the methods described herein can be used to create sequencing libraries, amplification products, and the like which can be utilized for downstream analysis methodologies. The disclosed methods are not limited by any downstream application.

EXAMPLES

The following examples are illustrative only and are not intended to limit the scope of the application. Modifications will be apparent and understood by skilled artisans and are included within the spirit and under the disclosure of this application.

Example 1—Depletion of Unwanted RNA Species from a Sample

In this example total RNA is the target nucleic acid in the sample, and RNA depletion involves four main steps: 1) hybridization, 2) RNase H treatment, 3) DNase treatment, and 4) target RNA clean up.

Hybridization is accomplished by annealing a defined DNA probe set to denatured RNA in a sample. A RNA sample, 10-100 ng, is incubated in a tube with 1 µL of a 1 µM/oligo DNA oligo probe set (probes corresponding to SEQ ID NOs: 1-333, as listed in Table 1), 3 µL of 5× Hybridization buffer (500 mM Tris HCl pH 7.5 and 1000 mM KCl), 2.5 µL of 100% formamide and enough water for a total reaction volume of 15 µL. The hybridization reaction is incubated at 95° C. for 2 min to denature the nucleic acids, slow cooled to 37° C. by decreasing temperature 0.1° C./sec and held at 37° C. No incubation time needed once the reaction reaches 37° C. The total time it takes for denaturation to reach 37° C. is about 15 min.

Following hybridization, the following components are added to the reaction tube for RNase H removal of the unwanted RNA species from the DNA:RNA duplex; 4 µL 5× RNase H buffer (100 mM Tris pH 7.5, 5 mM DTT, 4 0 mM MgCl$_2$) and 1 µL RNase H enzyme. The enzymatic reaction is incubated at 37° C. for 30 min. The reaction tube can be held on ice.

Following the removal of the RNA from the DNA:RNA hybrid, the DNA probes are degraded. To the 20 µL reaction tube, the following components are added: 3 µL 10× Turbo DNase buffer (200 mM Tris pH 7.5, 50 mM CaCl$_2$), 20 mM MgCl$_2$), 1.5 µL Turbo DNase (Thermo Fisher Scientific) and 5.5 µL H$_2$O for a total volume of 30 µL. The enzymatic reaction is incubated at 37° C. for 30 min followed by 75° C. for 15 min. The 75° C. incubation can serve to fragment the target total RNA to desired insert sizes for use in downstream processing, in this example the target insert size is around 200 nt of total RNA. The timing of this incubation step can be adjusted depending on the insert size needed for subsequent reactions, as known to a skilled artisan. Following incubation, the reaction tube can be held on ice.

After hybridization of the probes to the unwanted RNA, removal of the RNA, and removal of the DNA, the target total RNA in the sample can be isolated from the reaction conditions. The reaction tube is taken from 4° C. and allowed to come to room temperature and 60 µL of RNAClean XP beads (Beckman Coulter) are added and the reaction tube is incubated for 5 min. Following incubation, the tube is placed on a magnet for 5 min., after which the supernatant is gently removed and discarded. While still on the magnet, the beads with the attached total RNA are washed twice in 175 µL fresh 80% EtOH. After the second wash, the beads are spun down in a microcentrifuge to pellet the beads at the bottom of the tube, the tube is placed back on the magnet and the EtOH is removed, being careful to remove as much of the residual EtOH as possible without disturbing the beads. The beads are air dried for a few minutes, resuspended in 9.5 µL of ELB buffer (Illumina), allowed to sit a few more minutes at RT and placed back on the magnet to collect the beads. 8.5 µL of the supernatant is transferred to a fresh tube and placed on ice for additional downstream processing, such as created cDNA from the target total RNA.

In another example, 100 ng total RNA is diluted in 11 µL nuclease-free ultrapure water in each well of a 96-well PCR plate. To each well is added 4 µL of DNA probes (SEQ ID NOs: 1-333) in hybridization buffer and the well contents are mixed and optionally centrifuged. The plate is heated at 95° C. for 2 min and then the temperature is reduced at 0.1° C. per second until the temperature reaches 37° C. and then held at 37° C. to hybridize the probes. The plate is centrifuged at 280×g for 10 seconds. To degrade the DNA:RNA hybrids, to each well is added 5 µL of RNase in buffer and the well contents are mixed. The plate is heated at 37° C. for 15 min and then held at 4° C. To each well is added 10 µL of DNase in buffer and the well contents are mixed. The plate is heated at 37° C. for 15 min and then held at 4° C. The sample plate is centrifuged at 280×g for 10 seconds. To each well is added 60 µL RNAClean XP beads and the well contents are mixed. The plate is incubated at room temperature for 5 min. The plate is placed on a magnetic stand until the supernatant is clear (about 5 min). The supernatant in each well is removed and discarded. The beads are washed twice with 80% ethanol. Residual ethanol is removed from each well and the plate is air-dried on the magnetic stand for 1 min. To each well is added 10.5 µL of elution buffer, the well contents are mixed, and the plate is incubated at room temperature for 2 min. The plate is sealed and centrifuged at 280×g for 10 seconds. The plate is placed on a magnetic stand until the supernatant is clear (about 2 min). From each well, 8.5 µL of supernatant is transferred to the corresponding well of a new plate.

Example 2—cDNA Synthesis

Further processing of the RNA from Example 1 could be making a library preparation from the RNA target nucleic acids that can be sequenced for example by NGS. To 8.5 µL of the final reaction from Example 1, 8.5 µL of Elute, Prime High Concentration Random Hexamer Mix buffer (EPH buffer, TruSeq Stranded Total RNA Kit, Illumina) is added for a total volume of 17 µL. The sample is incubated at 65° C. for 2 min to denature the nucleic acids. Following denaturation, the reaction tube can be held on ice. First strand synthesis is performed by adding 8 µL of a reverse transcription enzyme mix (9 µL First Strand Synthesis Mix (FSA, TruSeq Stranded Total RNA Kit, Illumina) and 1 µL Protoscript II RT, (NEB)) to the denatured sample for a total volume of 25 µL. The reaction mix is incubated in a heated lid thermocycler under the following conditions: 25° C. for 5 min, 42° C. for 25 min, 70° C. for 15 min. Once the first strand synthesis reaction is complete the reaction tube can be held on ice.

Second strand cDNA synthesis can be performed by adding 5 µL Resuspension Buffer (RSB, TruSeq Stranded Total RNA Kit, Illumina) and 20 µL Second Strand Marking Mix (SSM buffer, TruSeq Stranded Total RNA Kit, Illumina) to the iced sample. The reaction tube is incubated at 16° C. for 60 min, and the sample may then be held on ice.

Following the cDNA synthesis steps, the cDNA can be cleaned up and separated from reaction components by, for example, adding 90 µL of SPB (Illumina) to the reaction tube and incubating for 5 min at RT. Following incubation, the tube is placed on a magnet for around 8 min to collect the paramagnetic beads and the supernatant is gently removed and discarded. While still on the magnet, the beads are washed twice with 175 µL fresh 80% EtOH. Following the washes, the beads are centrifuged to the bottom of the tube, the tube is place back on the magnet and EtOH is gently removed and discarded. The beads are dried for a few minutes and resuspended in 18.5 µL RSB, mixed well and allowed to incubate at RT for around 5 min before placed back on the magnet. Depending on the downstream application, the desired amount of purified cDNA can be removed to a new tube. In this example, a library prep for downstream sequencing is being made so 17.5 µL of the supernatant is transferred to a new tube which can be kept on ice.

Example 3—Library Preparation for Next Generation Sequencing

One method for preparing a library for sequencing includes A-tailing cDNA fragments, ligating adaptors, amplifying target fragments, and quantifying resultant fragments prior to sequencing.

The tube with 17.5 µL of purified cDNA from Example 2 is used for processing. To the purified cDNA is added 12.5 µL ATL (Illumina) for A-tailing the fragments. The reaction tube is incubated at 37° C. for 30 min followed by incubating at 70° C. for 5 min and the tube is put back on ice. Adaptors are ligated to the A-tailed sample by added in order: 2.5 µL RSB, 2.5 µL Index Adaptors (TruSeq Stranded Total RNA Kit, Illumina) and 2.5 µL of Ligation buffer (Illumina). The reaction tube is incubated at 30° C. for 10 min after which point 5 µL of Stop Ligation buffer (Illumina) is added and the reaction is held on ice.

Once the adaptor ligation reaction is completed, the ligated fragments are separated from the reaction components. To purify the adaptor ligated fragments, 34 µL SPB is added to the reaction tube which is incubated at RT for around 5 min. The tube is then placed on a magnet for capturing the paramagnetic beads and the beads are washed twice with 175 µL 80% EtOH, the EtOH being gently removed after the second wash. Following a 3 min air dry of the beads, the beads are resuspended in 52 µL RSB, the slurry in mixed, allowed to sit at RT for an additional 5 min, and placed back on the magnet. The supernatant (50 µL) is transferred to a fresh tube for a second round of bead cleanup.

For the second round, 40 µL SPB is added to the 50 µL sample and the process described above is repeated except the final purified fragments are resuspended in 21 µL of RSB and 20 µL of the final purified sample is transferred to a new reaction tube for subsequent amplification which increases the amount of target sequence for optimized sequencing results.

To the 20 µL of purified adaptor ligated sample, 5 µL of PCR primer cocktail (PPC, TruSeq Stranded Total RNA Kit, Illumina) and 25 µL PPM (TruSeq Stranded Total RNA Kit, Illumina) are added and the following amplification program in a heated lid thermocycler is performed: 98° C. for 30 sec followed by the cycled program 98° C. at 10 sec, 60° C. at 30 sec, 72° C. at 30 sec. The number of amplification cycles is dependent on the amount of RNA input at the beginning of the whole process. For example, for 100 ng RNA, approximately 12-13 cycles can be adequate, for 10 ng 15-16 cycles, and for 1 ng 17-18 cycles may be needed. The number of amplification cycles is typically optimized for any preparation as known to a skilled artisan.

The amplicons can be purified away from reaction conditions by adding 50 µL SPB to the reaction tube, incubate at RT, centrifuge the tube to pellet the beads and magnetically capture the beads. The supernatant can be discarded and the beads washed as previously stated followed by resuspension of the washed beads in 26 µL RSB, magnetic bead capture and transfer of the supernatant containing the DNA library for sequencing to a fresh tube. The library is typically quantified and analyzed prior to sequencing, for example by measuring an aliquot using the Qubit™ High Sensitivity kit (Thermo Fisher Scientific) and/or running an aliquot on a Bioanalyzer (Agilent). A skilled artisan will appreciate the many ways in which nucleic acids in a sample can be quantitated.

The resulting library preparation can then be used for next generation sequencing, microarray analysis or other downstream applications. For applications such as sequencing, the library preparation methodology is determined by the sequencing instrument being used and the companion library preparation method defined for that sequencing instrument. In this example, the library preparation method is characteristic of library creation when sequencing on Illumina sequencing instruments. A skilled artisan will understand that library preparation methods may vary depending in sequencing instrumentation, as such the present examples are exemplary only and the present RNA depletion methods are not limited to any particular library preparation workflow. Indeed, the present methods provide a RNA depleted sample that can input into any downstream applications that would benefit from a RNA sample depleted of unwanted RNA species.

Example 4—Microbial Transcriptome Analysis

In this example, microbial isolates, a mixed sample of bacterial species, and a standard cell mix were obtained from ATCC for testing.

| Sample type | Microbial species tested |
|---|---|
| Microbial isolates | E. coli, B. subtilis, S. Epidermidis, E. cloacae and B. cereus |
| ATCC-MSA2002 20 strain mix | A. baumannii, A. odontolyhticus, B. cereus, B. vulgatus, B. adolescentis, C. beijerinckii, C. acnes, D. radiodurans, E. faecalis, E. coli, H. pylori, L. gasseri., N. meningitidis, P. gingivalis, P. aeruginosa, R. sphaeroides, S. aureus, S. epidermidis, S. agalactiae, S. mutans |
| ATCC MSA2006 Human gut mix | B. tragilis, B. vulgatus, B. adolescentis, C. difficile, E. faecalis, L. plantarum, E. cloacae, E. coli, H. pylori, S. enterica, y. enterococolitica, F. nucleatum |

Total RNA can be extracted using the RNeasy Power Microbiome Kit (Qiagen) following manufacturer's protocol and evaluated for integrity and quantified by Bioanalyzer RNA Electrophoresis (Agilent). 10-250 ng of total RNA from each sample can be used for rRNA depletion following either the RiboZero methodology (Illumina, following manufacturer's protocol) or the methods disclosed herein using RNase H enzymatic degradation of unwanted rRNA. Ribo-depleted and non-ribo depleted RNA (control) samples can be prepared for sequencing using the TruSeq Stranded Total RNA Sample prep kit (Illumina) following manufacturer's instructions. Libraries can be pooled and sequenced, for example, on a MiSeq or NextSeq sequencing instrument (Illumina) for 2×76 paired end reads.

Sequence filtering, alignment, and transcript coverage can be performed using the online BaseSpace Sequencing Hub (BSSH) and the following exemplary workflows, for example: 1) Partition rRNA Sequences App (parse rRNA sequences to denote as abundant sequences in analysis), 2) RNA Custom Genome Builder App (create STAR-compatible microbial transcriptome), and 3) RNA-Seq Alignment App (STAR-alignment and salmon-transcript quantification). To quantify rRNA from multiple strains within the microbial samples rRNA sequences can be retrieved from NCBI annotated genomes and used as inputs to the BSSH workflow.

Figure 5:
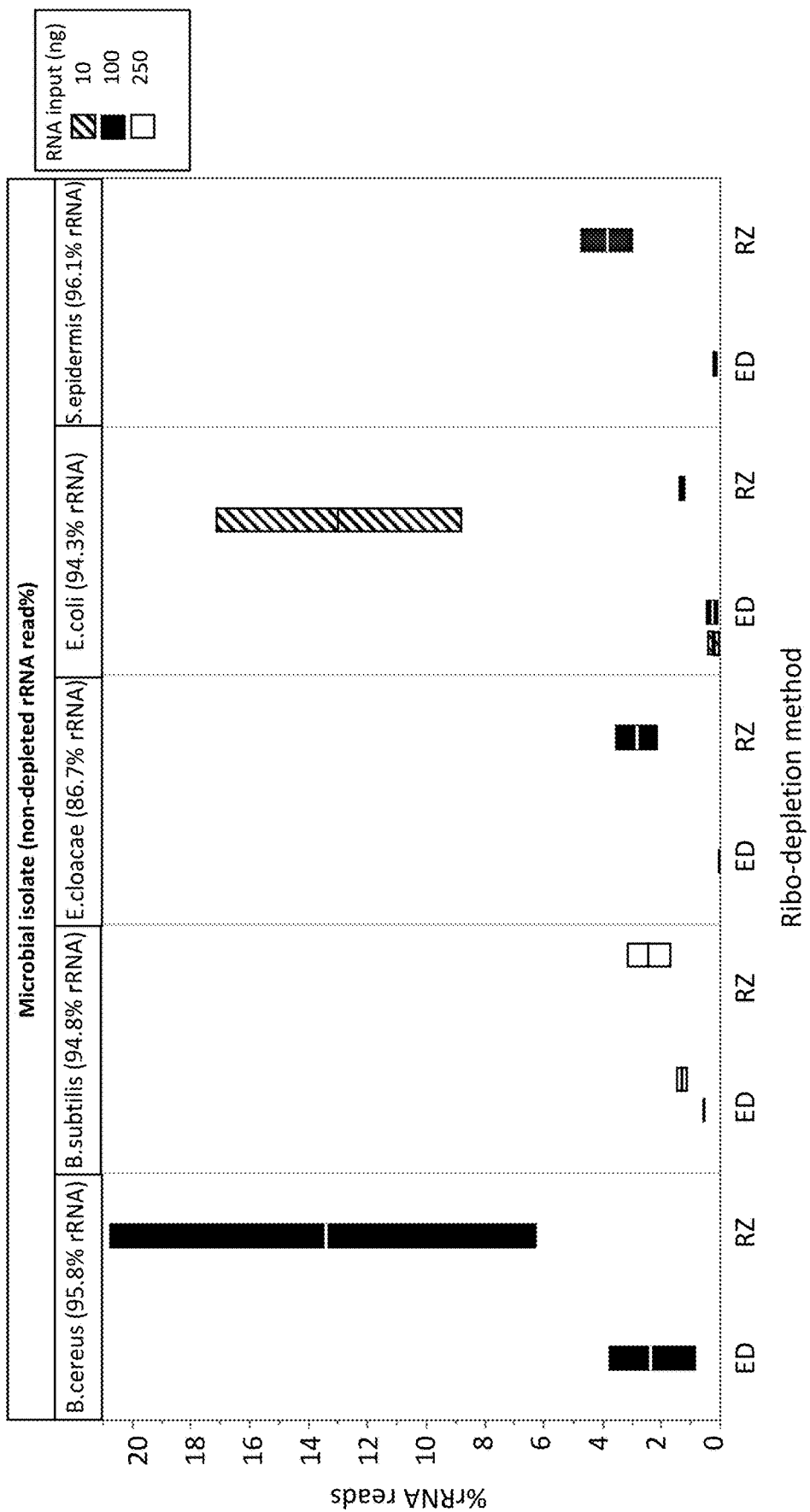
FIG. 5 shows exemplary data from removal of rRNA from different microbial species using low sample inputs comparing RiboZero® and RNase H enzymatic removal rRNA depletion methodologies. All sample read-depths were normalized. The X axis shows the rRNA depletion method (RZ=RiboZero or ED=RNase H enzymatic depletion method) and the Y axis shows the % rRNA reads.

The transcriptomes of the microbial isolates, microbial mixtures and control samples were sequenced and % rRNA reads compared. The RNase H enzymatic method disclosed herein is highly effective in depleting unwanted rRNA in the tested species (<5% rRNA reads). Ribosomal RNA depletion is most significant for the E. coli low input sample (10 ng) using the RNase H method comparative to the established RiboZero method; <0.5% vs 13% average rRNA reads, respectively (FIG. 5).

Figure 6:
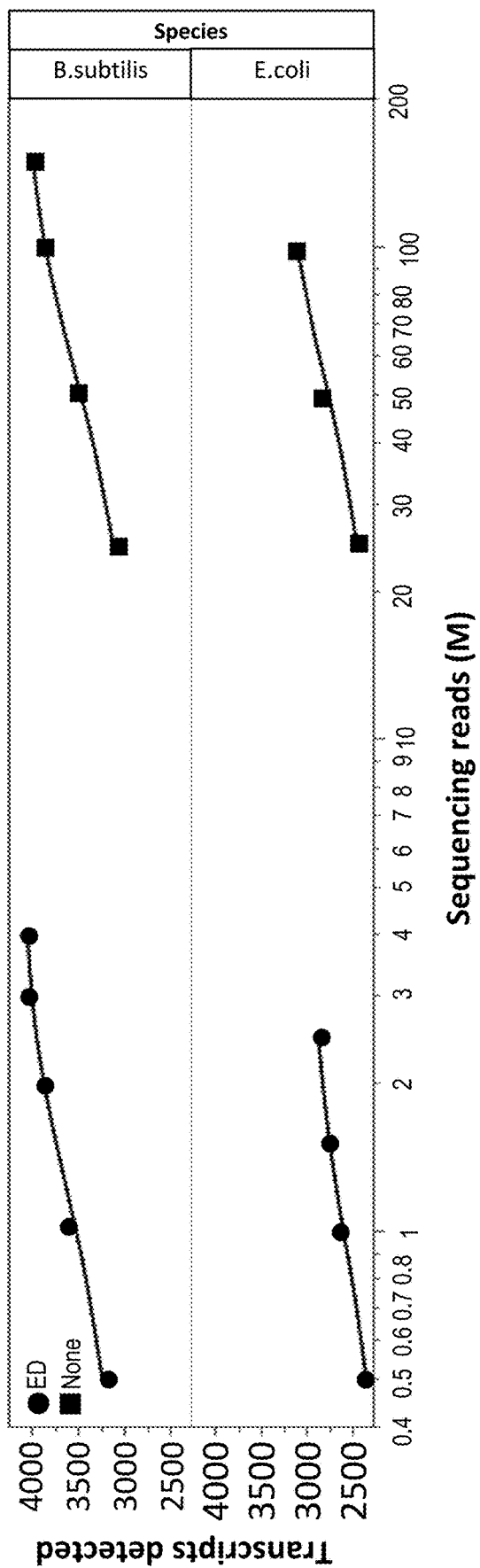
FIG. 6 shows exemplary transcript detection data at various read depths for B. subtilis and E. coli following RNase H rRNA depletion (ED) on the left side of the graph compared to no rRNA depletion (None) on the right side of the graph. The X axis shows the sequencing reads (M) and the Y axis shows the number of transcripts detected.

Data was used to access the enrichment of biologically important RNA reads when the RNase H rRNA depletion method was used and compared to no rRNA depletion. FIG. 6 demonstrates the results of an assessment where, in general, a 20-50× reduction in read depth was seen for a B. subtilis or E. coli sample if the sample was rRNA depleted prior to library preparation and sequencing using the RNase H methods compared to no rRNA depletion.

Figure 7A:
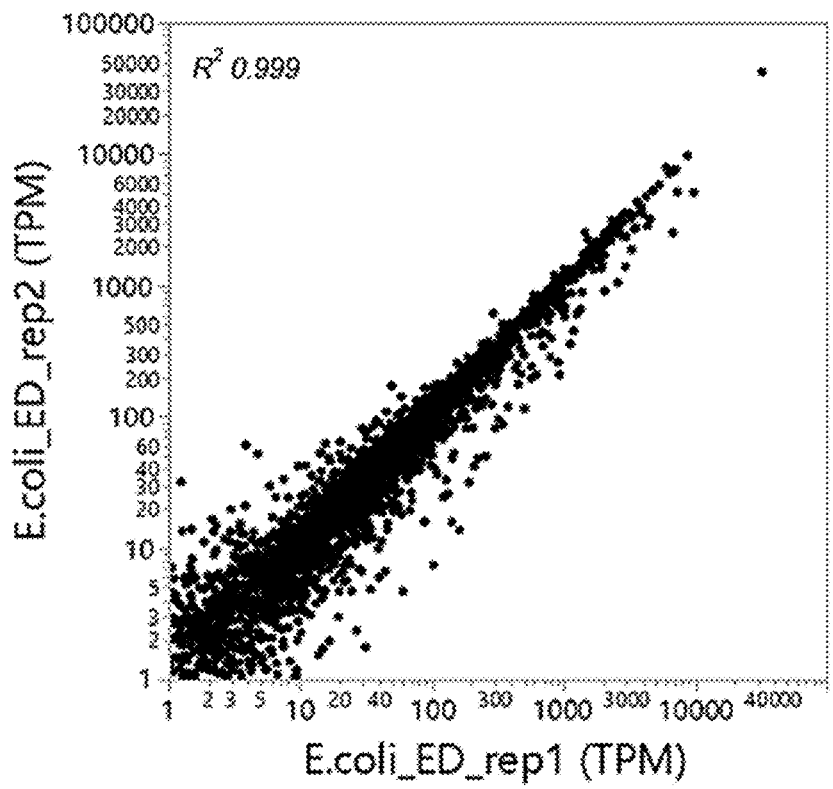
FIGS. 7A-7B show exemplary graphs for gene expression pairwise linear regression data demonstrating the reproducibility of the disclosed methods for rRNA depletion. Panel 7A exemplifies two E. coli replicate gene expression levels and Panel 7B exemplifies two B. subtilis replicate gene expression levels. Both bacterial types demonstrate high correlation between gene expression level replicates following RNase H rRNA depletion.
Figure 7B:
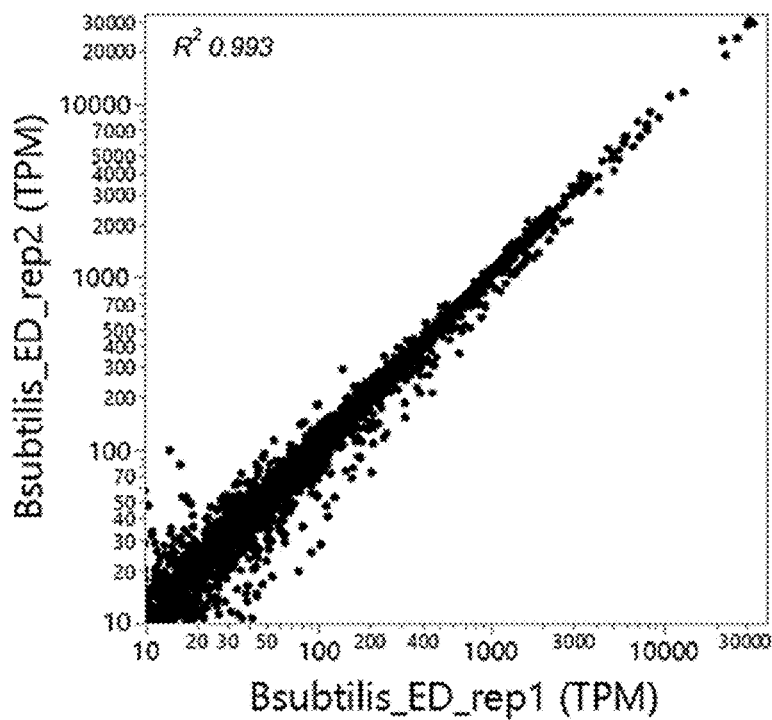

Data collected was evaluated to determine the reproducibility of the experimental microbial transcriptome sequencing efforts. Pairwise linear regression of gene expression levels was determined between the RNase H rRNA depleted replicates for *E. coli* and *B. subtilis* as example systems. High correlation ($R^2 > 0.99$) indicated the ability of the RNase H rRNA depletion method to reproducibly remove rRNA from samples (FIG. 7).

Figure 8:
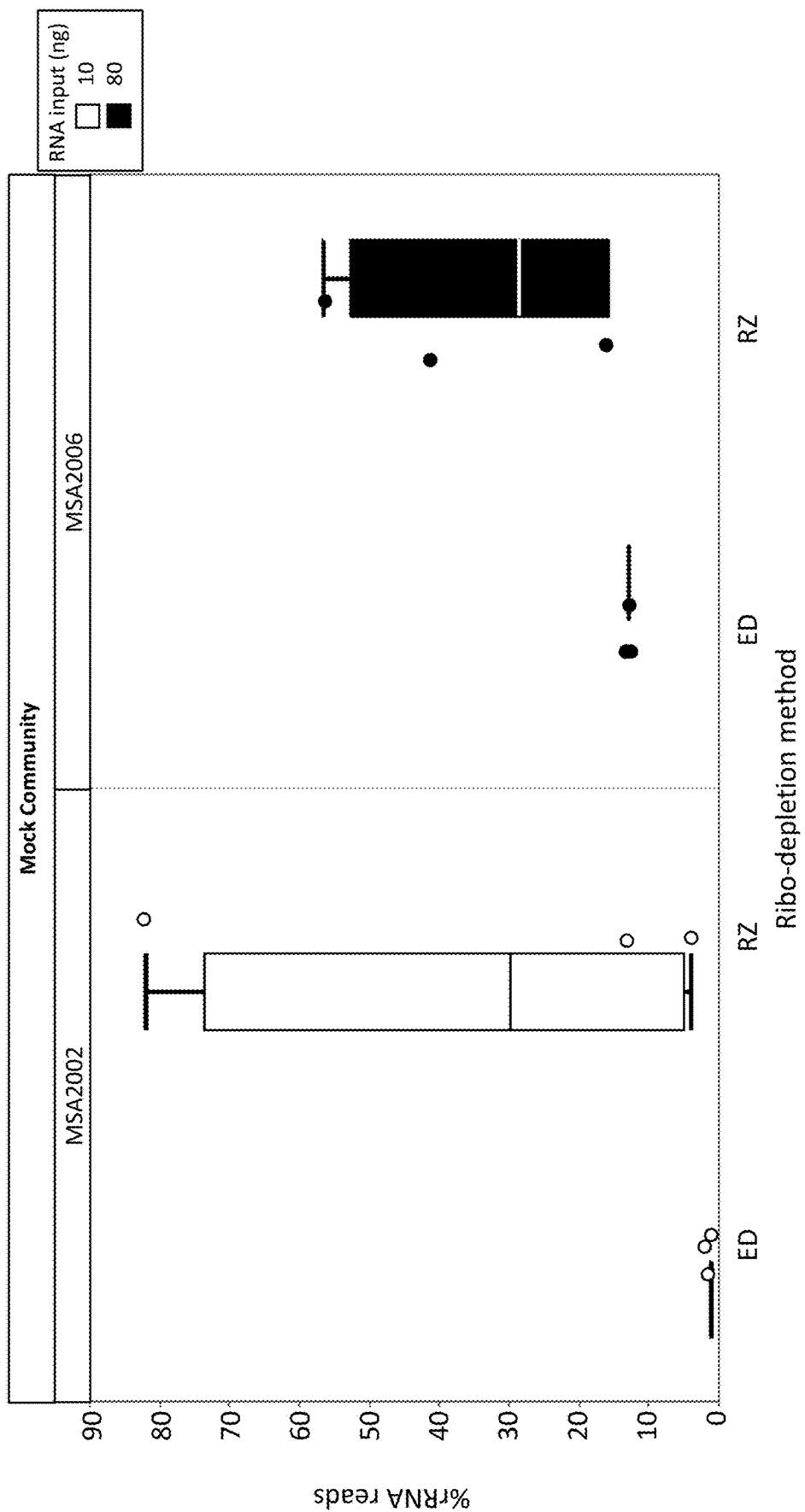
FIG. 8 shows exemplary triplicate rRNA read data for a 20 strain (MSA-2002, left side) and a 12 strain (MSA-2006, right side) mixed sample. The mixed sample triplicates were rRNA depleted by the RiboZero method (RZ) or the RNase H (ED) depletion method described herein. RNA input for the MSA2002 samples was 10 ng while that for the MSA2006 was 80 ng. The X axis shows the rRNA depletion method and the Y axis shows the % rRNA reads.

For evaluating whether the RNase H enzymatic rRNA depletion method might be useful for rRNA depletion of mixed samples, FIG. 8 demonstrates exemplary data for the mixed samples of 20 strain MSA2002 and human gut MSA2006 in triplicate. Low input samples of 10 mg total RNA from MSA2002 or 80 ng total RNA from MSA2006 was used for rRNA depletion methods. For the 20 strain MSA2002 samples, the RNase H rRNA depletion method reduced rRNA reads by 83% or <2% of sequence reads while the RiboZero method of rRNA depletion resulted in a more variable and higher rRNA abundance compared to non-depleted samples. For the 12 strain MSA2006 samples, the same outcome was seen where RNase H method reduced rRNA reads by approximately 95% to <13% of the sequencing reads comparative to non-depleted samples, the RiboZero method yielded more variable results.

As such, it was determined that in experiments for evaluating samples, either mixed or otherwise, the RNase H rRNA depletion method provides a robust and effective workflow for reducing unwanted rRNA in samples for high quality microbial whole transcriptome research. The RNase H rRNA depletion method was also very effective and compatible with low input samples.

Example 5—Effect of Formamide on RNA Depletion

Figure 2A:
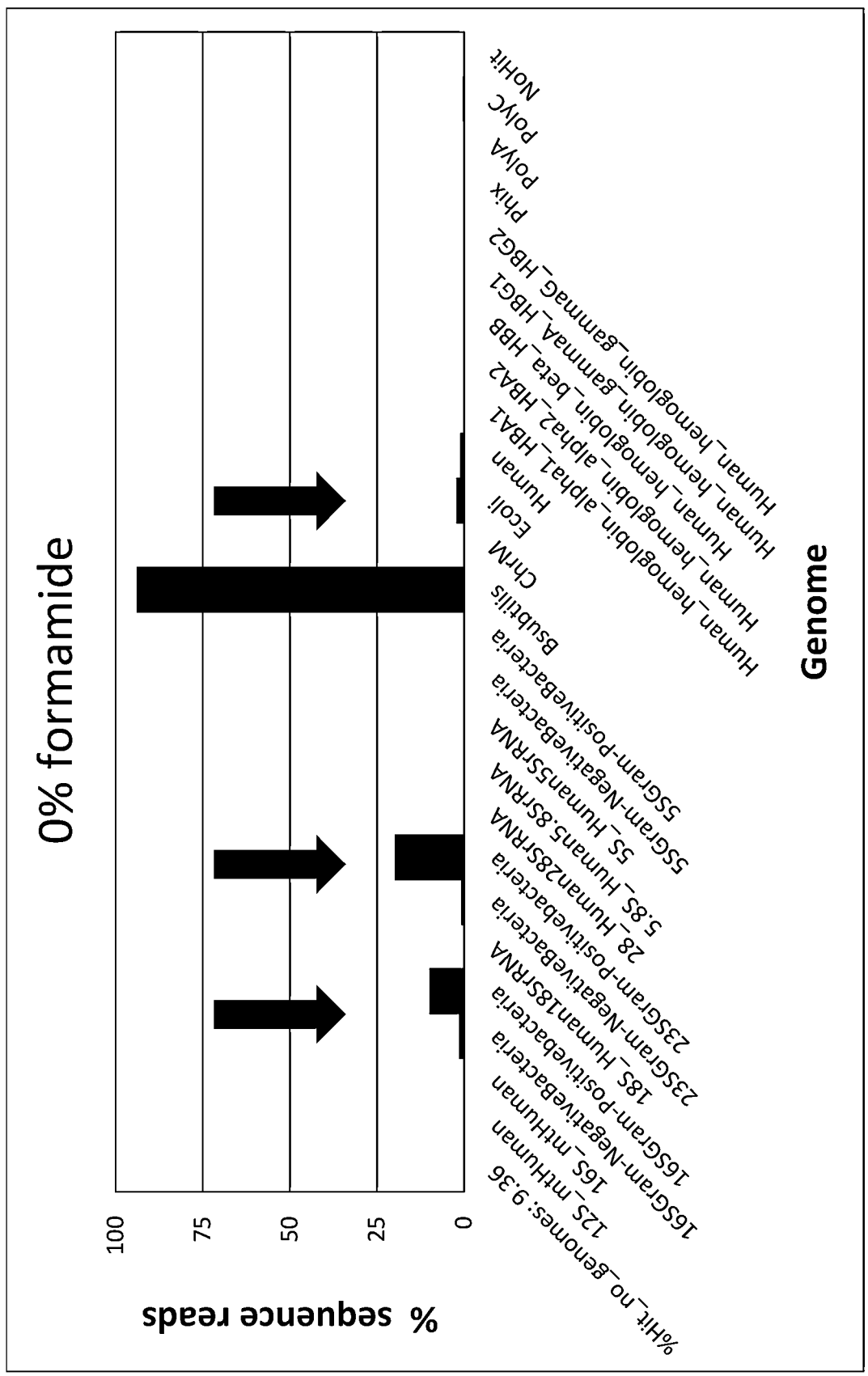
FIGS. 2A-2C show exemplary data for rRNA depletion from a sample of B. subtilis when formamide is added to the rRNA depletion workflow (2A) 0% formamide, (2B) 25% formamide, (2C) 45% formamide. In each panel, the X axis lists the detected rRNA species and the Y axis shows percent depletion through percent sequence reads.
Figure 2B:
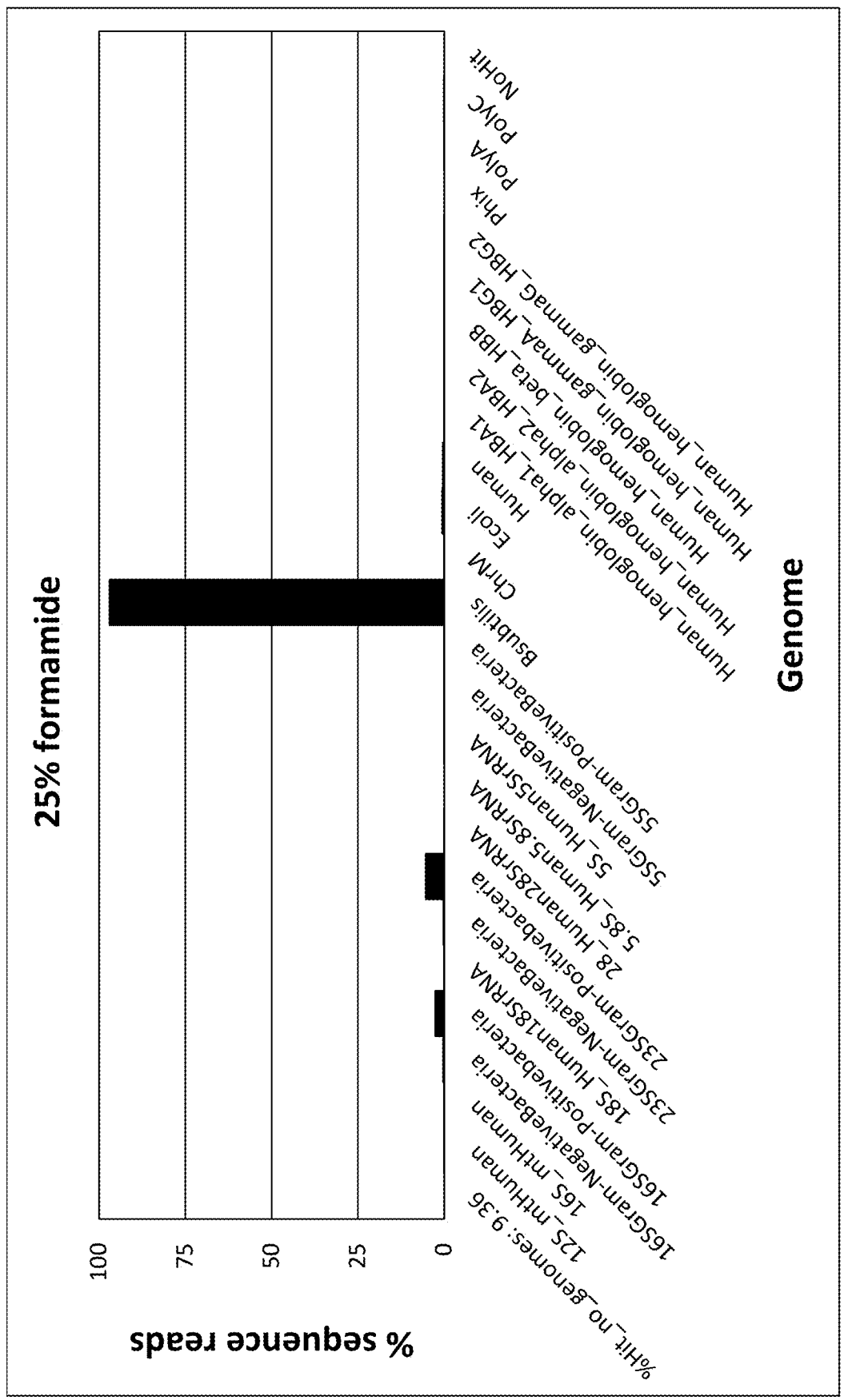
Figure 2C:
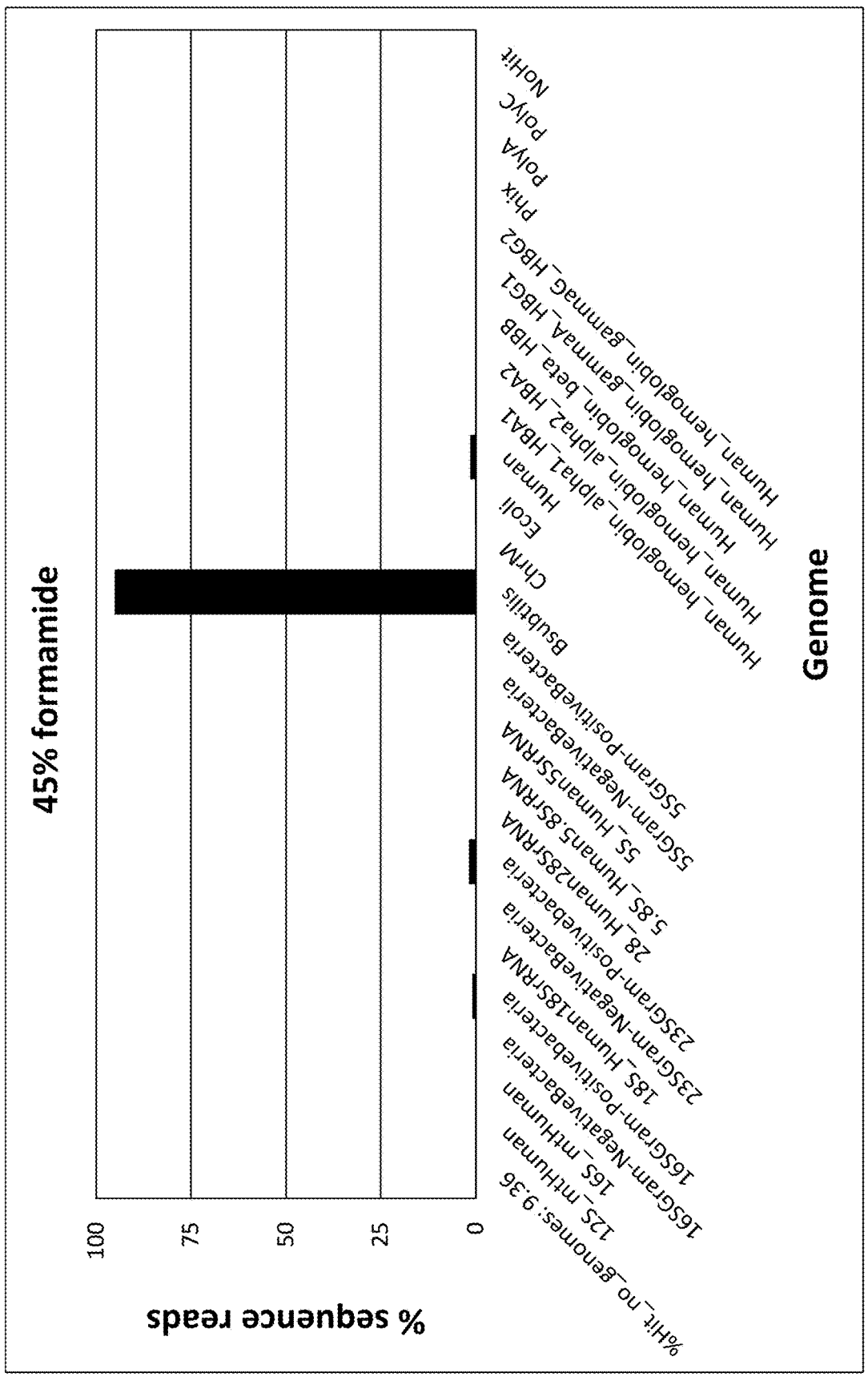

FIG. 2 shows exemplary data where an RNA sample has been depleted of unwanted RNA species. The RNA sample was depleted of unwanted RNA using the methods described herein, while evaluating the effects of formamide concentration on unwanted RNA depletion. In this example, the DNA probes targeted depletion of unwanted rRNA species from Gram positive bacteria (23S, 16S, 5S), Gram negative bacteria (23S, 16S, 5S including), human mitochondria (16S, 12S), human rRNAs (28S, 18S, 5.8S, 5S), human hemoglobin mRNAs (HBA-A1, HBA-A2, HBB, HBG1, HBG2) while the target RNA species is total RNA from *B. subtilis*. As the concentration of formamide increases the percentage of unwanted RNA species reads significantly decreases. For example, no formamide during RNA depletion resulted in off target RNA reads for Gram positive 23S and 16S and Gram negative (including *E. coli*) bacteria 23S and 16S, including *E. coli* specific sequences. The addition of 25% formamide to the hybridization reaction resulted in undetectable off target reads for Gram negative 23S and 16S (with significant reduction in off targets reads specific to *E. coli*) and significantly reduced off target reads for the Gram positive 23S and 16S. The addition of formamide to 45% of the hybridization reaction saw additional significant decreases in off target reads for the Gram positive undesired rRNA 23S and 16S as well as a further drop in off target *E. coli* reads. As such, the addition of formamide to the RNA depletion hybridization reaction is shown to increase the amount of Gram positive and Gram negative undesired RNAs depleted as evidenced by the reduction in off target reads for those species. In general, it was found that the addition of formamide improves depletion of the unwanted rRNA transcripts. When using *B. subtilis* RNA as the target RNA for analysis, for example, assaying for *E. coli* and human rRNA sequences can provide a measure of potential contamination.

Example 6—Variation of Input Starting Material

Experiments were performed to identify the impact of input starting material on RNA depletion and subsequent downstream analysis, such as shown in FIG. 3 where RNA depleted and enriched RNA samples from human brain (HBR) and a universal human RNA (UHR) were used to create libraries for sequencing on the Illumina NextSeq™ 500 or 550 sequencing instrument. Following RNA depletion using 100 ng, 10 ng or 1 ng of input samples, sequencing libraries were prepared as exemplified in Examples 1-3. Sequencing was performed as recommended by the NextSeq™ user guide following by data analysis using two BaseSpace (Illumina) applications, RNASeq Alignment application and the RNAExpress application. Data analysis for *B. subtilis* and *E. coli* presence was also performed using a modified tool Fastqscreen (https://www.bioinformatics.babraham.ac.uk/projects/fastq_screen/). The data shows that the RNA depletion remains constant for both HBR and UHR regardless of amount of input of the RNA sample and the % total alignment for the target RNA, while decreasing with decreasing input amounts, still shows that actionable and useful sequence data can be gathered even when using 1 ng of input sample. Further, in a comparative experiment the current method for RNA depletion leads to fewer % abundance of non-target reads at all input levels (100 ng~3%, 25 ng~4%, 10 ng~3% and 1 ng~3%) when compared to data when using RiboZero rRNA depletion kit (Epicentre) for RNA depletion (100 ng~3%; 25 ng~5%, 10 ng~8% and 1 ng~35%) or NEBNext rRNA depletion methods (NEB) (100 ng~8%, 25 ng~8%, 10 ng~9% and 1 ng~30%).

Example 7—RNA Depletion of Mouse and Rat RNA Samples

To demonstrate that the RNA depletion methods can be useful for non-human RNA samples both mouse and rat RNA samples were used for RNA depletion methods. For FIG. 4, either mouse or rat RNA samples were depleted of unwanted RNA using equivalent methods and DNA probes as for human RNA samples. Formamide was again varied for each rodent species, including no formamide, 25% formamide or 45% formamide in the hybridization reaction. While total % aligned reads is not affected with the increase in formamide, there may be a trend toward an increase in detection of non-target reads as formamide increases. As such, the addition of formamide to the hybridization reaction maybe useful in some sample types, as it can improve detection of some transcripts so its addition should be optimized.

Example 8—Preparation of Supplemental Mouse Probes

Within the pool of 333 DNA probes described above for enzymatic removal of unwanted sequences (SEQ ID NOs: 1-333), the DNA oligonucleotides for eukaryotic rRNA depletion were designed based upon the major human rRNA transcripts, namely 5S, 5.8S, 18S, and 28S, as well as the two mitochondrial rRNA sequences, 12S and 16S. When tested on human total RNA, this 333-DNA probe pool was very effective at removing rRNA reads. However, when tested with mouse (*Mus musculus*) or rat (*Rattus norvegicus*) total RNA samples, depletion was less robust, suggesting that the probes did not hybridize and remove some regions of rodent rRNA sequences efficiently because these mouse and rat regions were divergent from human sequences.

Figure 9:
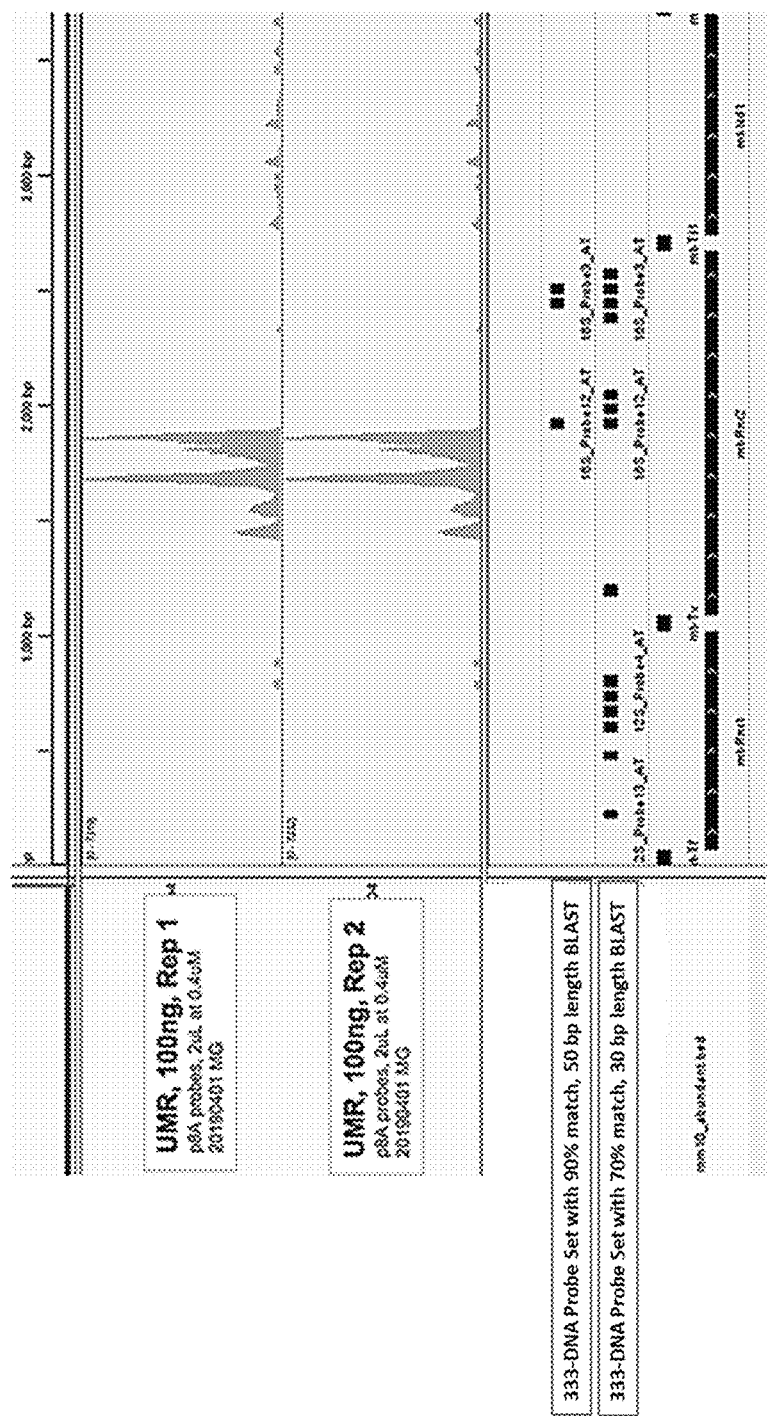
FIG. 9 shows sequencing read coverage of the mouse mitochondrial 12S (mt-Rnr1 and 16S (mt-Rnr2) rRNA loci (bottom of the figure) and the effect of the 333 DNA probe set (SEQ ID NOs: 1-333) on depleting mouse 16S rRNA from universal mouse reference RNA (UMR) samples. Squares indicate location of 90% match over 50 base length or 70% match over 30 base pair length with the 333 DNA probe set. In the absence of additional mouse and rat probes, gaps without probe coverage correspond to peaks in residual or undepleted rRNA for the two replicates (Rep 1 and Rep2) shown at the top of the figure.

The fastq files containing the total sequencing reads obtained from the 333-DNA probe experiment were aligned to mouse and rat ribosomal RNA sequences and to the 333 DNA probe sequences. The alignment results showed that probe coverage across all the ribosomal RNA sequences was generally good, but there were some regions where probe sequences did not align as well to rodent rRNAs. More specifically, the majority of the mouse and rat rRNA reads that did not align to the probe pool map belonged to either the 28S or 16S rodent rRNA transcripts (Table 2). The alignments were done with Bowtie2 (See Langmead and Salzberg, *Nature Methods* 2012, 9:357-359), version 2.1.0 with its default settings. Most of the ribosomal RNA that did not get depleted with the 333 DNA probe enzymatic method were from the same regions that lacked probe alignment (FIG. 9).

TABLE 2

| Mouse/Rat Genbank sequences used for the study | | |
| --- | --- | --- |
| Genome | 16S | 28S |
| *Mus musculus* | NC_005089.1: 1094-2675 | NR_003279.1 |
| *Rattus norvegicus* | NC_001665.2: 1094-2664 | NR_046246.1 |

To deplete these regions more effectively, additional probes were designed to cover the regions identified above for mouse and rat ribosomal RNA sequences. To minimize the number of additional probes and probe redundancies, additional probes were designed against the gaps in mouse rRNA sequences, then these data were informatically pooled together with the 333 DNA probe set to identify any remaining gaps in rat rRNA coverage by aligning the combined pool to rat rRNA transcripts. This sequential process yielded a total of 44 additional oligonucleotide probes, to provide a supplemental pool of 377 probes. Sequencing experiments as described above were repeated with the 377 DNA probe set. In both mouse and rat samples, addition of the 44 new probes resulted in a decrease in the percentage of rRNA reads from the libraries compared to the 333-DNA probe set, showing increased depletion efficiency (Table 3).

TABLE 3

| Percent ribosomal RNA in sequencing reads with 333- and 377-Probe Sets | | |
| --- | --- | --- |
| RNase H Probe Set | Mouse Sample | Rat Sample |
| 333 DNA Probe Set | 9.5% | 5.3% |
| 377 DNA Probe Set | 7.0% | 3.7% |

Supplementation of the 333 DNA probe pool with additional probes against certain rodent sequences improved rRNA depletion in the tested rodent samples. Exemplary probes against mouse 16S include SEQ ID NOs: 385 to 393. Exemplary probes against mouse 28S include SEQ ID NOs: 400 to 419. Exemplary probes against rat 16S include SEQ ID NOs: 394 to 399. Exemplary probes against rat 28S include SEQ ID NOs: 420 to 428.

The invention claimed is:

1. A method for depleting off-target RNA molecules from a nucleic acid sample comprising:
   a. contacting a nucleic acid sample comprising at least one target RNA or DNA sequence and at least one off-target RNA molecule with a probe set comprising at least 40 DNA probes complementary to discontiguous sequences along the full length of the at least one off-target RNA molecule, thereby hybridizing the at least 40 DNA probes to the off-target RNA molecules to form DNA:RNA hybrids, wherein each DNA:RNA hybrid is at least 5 bases apart, or at least 10 bases apart, along a given off-target RNA molecule sequence from any other DNA:RNA hybrid, and each of the at least 40 DNA probes is 40 to 60 bases in length; and
   b. contacting the DNA:RNA hybrids with a ribonuclease that degrades the RNA from the DNA:RNA hybrids, thereby degrading the off-target RNA molecules in the nucleic acid sample to form a degraded mixture, wherein the ribonuclease is hybridase.

2. The method of claim 1, further comprising:
   a. degrading any remaining DNA probes by contacting the degraded mixture with a DNase I to form a DNA degraded mixture; and
   b. separating the degraded RNA from the degraded mixture or the DNA degraded mixture.

3. The method of claim 1, wherein the contacting with the probe set comprises treating the nucleic acid sample with formamide wherein the formamide is present during the contacting with the probe set at a concentration of from about 10 to 45% by volume.

4. The method of claim 1, wherein the contacting with the probe set comprises applying heat above the melting temperature of the at least one DNA:RNA hybrid.

5. The method of claim 1, wherein the nucleic acid sample is from a human or from a non-human eukaryote, bacterium, virus, plant, soil, or a mixture thereof, optionally wherein the non-human eukaryote is a rat, mouse, or non-human primate.

6. The method of claim 1, wherein the off-target RNA is rRNA and/or globin mRNA.

7. The method of claim 1, wherein the probe set comprises at least two DNA probes that hybridize to at least one off-target RNA molecule selected from:
   a. 28S, 18S, 5.8S, 5S, 16S, and/or 12S from humans;
   b. HBA-A1, HBA-A2, HBB, HBG1, and HBG2 from hemoglobin, and 23S, 16S, and 5S from Gram positive or Gram negative bacteria; and/or c. rat 16S, rat 28S, mouse 16S, and mouse 28S, and combinations thereof.

8. The method of claim 1, wherein the probe set comprises DNA probes to a particular off-target RNA molecule that are complementary to about 80 to 85% of the sequence of the off-target RNA molecule,
optionally wherein the DNA probes comprise:
   a. two or more sequences selected from SEQ ID NOs: 1-333; or
   b. two or more sequences selected from SEQ ID NOs: 1-428; or
   c. two or more sequences selected from SEQ ID NOs: 1-377; or
   d. two or more sequences selected from SEQ ID NOs: 1-333 and SEQ ID NOs: 378-428; or
   e. two or more sequences selected from SEQ ID NOs: 334-377; or
   f. two or more sequences selected from SEQ ID NOs: 378-428;
or a combination thereof.

9. A composition comprising
   a. a probe set comprising at least 40 DNA probes complementary to discontiguous sequences along the full length of at least one off-target RNA molecule in a nucleic acid sample, each DNA probe is hybridized at least 5, or at least 10, bases apart along the full length of the at least one off-target RNA molecule from any other DNA probe in the probe set, and each DNA probe is 40 to 60 bases in length; and
   b. a ribonuclease capable of degrading RNA in a DNA:RNA hybrid, wherein the ribonuclease is a hybridase.

10. The composition of claim 9, further comprising DNase I for degrading any remaining DNA probes.

11. The composition of claim 9, further comprising formamide wherein the formamide is present at about 10 to 45% by volume when the DNA probes come in contact with the nucleic acid sample.

12. The composition of claim 9, wherein the off-target RNA is rRNA and/or globin mRNA.

13. The composition of claim 9, wherein the probe set comprises at least two DNA probes that hybridize to at least one off-target RNA molecule selected from:
   a. 28S, 18S, 5.8S, 5S, 16S, and/or 12S from humans;
   b. HBA-A1, HBA-A2, HBB, HBG1, and HBG2 from hemoglobin, and 23S, 16S, and 5S from Gram positive or Gram negative bacteria; and/or
   c. rat 16S, rat 28S, mouse 16S, and mouse 28S, and combinations thereof.

14. The composition of claim 9, wherein the probe set comprises DNA probes comprising:
   a. two or more sequences selected from SEQ ID NOs: 1-333; or
   b. two or more sequences selected from SEQ ID NOs: 1-428; or
   c. two or more sequences selected from SEQ ID NOs: 1-377; or
   d. two or more sequences selected from SEQ ID NOs: 1-333 and SEQ ID NOs: 378-428; or
   e. two or more sequences selected from SEQ ID NOs: 334-377; or
   f. two or more sequences selected from SEQ ID NOs: 378-428;
   g. or a combination thereof.

15. A kit comprising:
   a. a probe set comprising at least 40 DNA probes complementary to discontiguous sequences at least 5, or at least 10, bases apart along the full length of at least one off-target RNA molecule in a nucleic acid sample, and each DNA probe is 40 to 60 bases in length;
   b. a ribonuclease capable of degrading RNA in a DNA:RNA hybrid, wherein the ribonuclease is hybridase; and
   c. DNase I capable of degrading any remaining DNA probes; and
   d. formamide wherein the formamide is present during the contacting with the probe set at a concentration of from about 10 to 45% by volume.

16. The kit of claim 15, wherein the off-target RNA is rRNA and/or globin mRNA.

17. The kit of claim 15, wherein the probe set comprises at least two DNA probes that hybridize to at least one off-target RNA molecule selected from:
   a. 28S, 18S, 5.8S, 5S, 16S, and/or 12S from humans;
   b. HBA-A1, HBA-A2, HBB, HBG1, and HBG2 from hemoglobin, and 23S, 16S, and 5S from Gram positive or Gram negative bacteria; and/or
   c. rat 16S, rat 28S, mouse 16S, and mouse 28S, and combinations thereof.

18. The kit of claim 15, wherein the probe set comprises DNA probes to a particular off-target RNA molecule that are complementary to about 80 to 85% of the sequence of the off-target RNA molecule,
optionally wherein the DNA probes comprise:
   a. two or more-sequences selected from SEQ ID NOs: 1-333; or
   b. two or more sequences selected from SEQ ID NOs: 1-428; or
   c. two or more sequences selected from SEQ ID NOs: 1-377; or
   d. two or more sequences selected from SEQ ID NOs: 1-333 and SEQ ID NOs: 378-428; or
   e. two or more sequences selected from SEQ ID NOs: 334-377; or
   f. two or more sequences selected from SEQ ID NOs: 378-428;
or a combination thereof.

19. The kit of claim 15, further comprising:
   a. a probe set comprising SEQ ID NOs: 1-333; and
   b. RNA purification beads.

20. A method of supplementing a probe set for use in depleting off-target RNA nucleic acid molecules from a nucleic acid sample comprising:
   a. contacting a nucleic acid sample comprising at least one RNA or DNA target sequence and at least one off-target RNA molecule from a first species with a probe set comprising at least 40 DNA probes complementary to discontiguous sequences along the full length of the at least one off-target RNA molecule from a second species, thereby hybridizing the at least two DNA probes to the off-target RNA molecules to form DNA:RNA hybrids, wherein
      i. each DNA:RNA hybrid is at least 5 bases apart, or at least 10 base apart, along a given off-target RNA molecule sequence from any other DNA:RNA hybrid; and
      ii. each DNA probe is 40 to 60 bases in length;
   b. contacting the DNA:RNA hybrids with hybridase that degrades the RNA from the DNA:RNA hybrids, thereby degrading the off-target RNA molecules in the nucleic acid sample to form a degraded mixture;
   c. separating the degraded RNA from the degraded mixture;
   d. sequencing the remaining RNA from the sample;

e. evaluating the remaining RNA sequences for the presence of off-target RNA molecules from the first species, thereby determining gap sequence regions; and
f. supplementing the probe set with additional DNA probes complementary to discontiguous sequences in one or more of the gap sequence regions.

21. The method of claim 20, wherein the composition of claim 9 is used to supply the hybridase and the probe set comprising the DNA probes complementary to discontiguous sequences along the full length of the at least one off-target RNA molecule of a human.

22. The method of claim 20, wherein the method is used to identify DNA probes that hybridize to one or more off-target RNA molecules from rat and/or mouse, optionally selected from rat 16S, rat 28S, mouse 16S, and mouse 28S, and combinations thereof.

* * * * *

UNITED STATES PATENT AND TRADEMARK OFFICE
CERTIFICATE OF CORRECTION

PATENT NO. : 11,976,271 B2
APPLICATION NO. : 17/812683
DATED : May 7, 2024
INVENTOR(S) : Scott Kuersten, Frederick Hyde and Asako Tetsubayashi It is certified that error appears in the above-identified patent and that said Letters Patent is hereby corrected as shown below:

In the Claims

In Column 154, Line 57, Claim 20, replace "base" with --bases--.

Signed and Sealed this
Thirteenth Day of August, 2024

Katherine Kelly Vidal
*Director of the United States Patent and Trademark Office*